US012741948B2

(12) United States Patent
Liu et al.

(10) Patent No.: US 12,741,948 B2
(45) Date of Patent: Sep. 22, 2026

(54) BENZOTHIAZOLE AND QUINOLINE DERIVATIVES AND THEIR USE

(71) Applicant: Shanghai Yao Yuan Biotechnology Co., Ltd., Shanghai (CN)

(72) Inventors: Danyang Liu, Shanghai (CN); Cong Xu, Shanghai (CN); Lawrence S. Melvin, Jr., Shanghai (CN); Xiong Wei, Shanghai (CN); Tongruei Raymond Li, Shanghai (CN); Jieqing Fan, Shanghai (CN); Yanfang Pan, Shanghai (CN); Huaixin Dang, Shanghai (CN); Henri Lichenstein, Guilford, CT (US); Tian Xu, Shanghai (CN)

(73) Assignee: Shanghai Yao Yuan Biotechnology Co., Ltd., Shanghai (CN)

(*) Notice: Subject to any disclaimer, the term of this patent is extended or adjusted under 35 U.S.C. 154(b) by 628 days.

(21) Appl. No.: 18/246,565

(22) PCT Filed: Sep. 23, 2021

(86) PCT No.: PCT/CN2021/119802
§ 371 (c)(1),
(2) Date: Mar. 24, 2023

(87) PCT Pub. No.: WO2022/063153
PCT Pub. Date: Mar. 31, 2022

(65) Prior Publication Data

US 2024/0116885 A1 Apr. 11, 2024

(30) Foreign Application Priority Data

Sep. 24, 2020 (WO) ................ PCT/CN2020/117437

(51) Int. Cl.

| | |
|---|---|
| ***C07D 417/12*** | (2006.01) |
| ***A61K 31/496*** | (2006.01) |
| ***A61P 31/00*** | (2006.01) |
| ***A61P 37/06*** | (2006.01) |
| ***C07D 215/38*** | (2006.01) |
| ***C07D 241/44*** | (2006.01) |
| ***C07D 277/82*** | (2006.01) |
| ***C07D 401/12*** | (2006.01) |
| ***C07D 487/08*** | (2006.01) |

(52) U.S. Cl.
CPC ............ *C07D 277/82* (2013.01); *A61P 31/00* (2018.01); *A61P 37/06* (2018.01); *C07D 215/38* (2013.01); *C07D 241/44* (2013.01); *C07D 401/12* (2013.01); *C07D 417/12* (2013.01); *C07D 487/08* (2013.01)

(58) Field of Classification Search
CPC .. C07D 417/12; C07D 417/10; C07D 277/82; A61K 31/496; A61K 31/428
USPC .............. 544/367; 548/161; 514/254.02, 367
See application file for complete search history.

(56) References Cited

U.S. PATENT DOCUMENTS

| | | | |
|---|---|---|---|
| 3,591,600 | A | 7/1971 | Fancher |
| 6,410,533 | B1 | 6/2002 | Hirth et al. |
| 2024/0109853 | A1 | 4/2024 | Liu et al. |
| 2024/0216362 | A1 | 7/2024 | Wei et al. |
| 2024/0226094 | A1 | 7/2024 | Wei et al. |
| 2025/0163008 | A1 | 5/2025 | Liu et al. |
| 2025/0241908 | A1 | 7/2025 | Dang et al. |

FOREIGN PATENT DOCUMENTS

| | | | | |
|---|---|---|---|---|
| CN | 86102102 | A | 1/1987 | |
| CN | 101830855 | A | 9/2010 | |
| CN | 103006645 | A | 4/2013 | |
| CN | 108373448 | A | 8/2018 | |
| KR | 20160124373 | A | 10/2016 | |
| RU | 2017139515 | A | 5/2019 | |
| WO | WO-2005037845 | A1 * | 4/2005 | ........... C07D 513/04 |

(Continued)

OTHER PUBLICATIONS

Corbo et al.: Antiproliferative activity evaluation of a series of N-1,3-benzothiazol-2-ylbenzamides as novel apoptosis inducers. Journal of Chemistry, vol. 2016, pp. 1-5, 2016.*

(Continued)

*Primary Examiner* — Charanjit Aulakh
(74) *Attorney, Agent, or Firm* — Mintz Levin Cohn Ferris Glovsky and Popeo, P.C.

(57) ABSTRACT

Provided are compounds of Formula (I) or (II) and related compositions and methods for their use as inhibitors of alpha-kinase 1 (ALPK1).

(I)

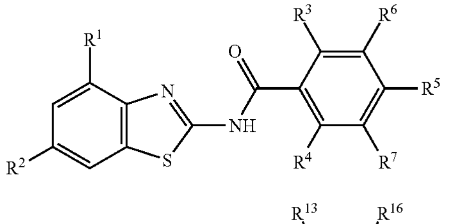

(II)

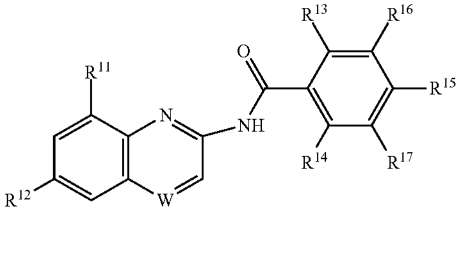

7 Claims, 5 Drawing Sheets

(56) References Cited

FOREIGN PATENT DOCUMENTS

| | | | |
|---|---|---|---|
| WO | 2008057862 | A2 | 5/2008 |
| WO | 2009002933 | A1 | 12/2008 |
| WO | 2013131018 | A1 | 9/2013 |
| WO | WO-2017223514 | A1 | 12/2017 |
| WO | 2019007362 | A1 | 1/2019 |
| WO | 2019046668 | A1 | 3/2019 |
| WO | 2020176863 | A1 | 9/2020 |
| WO | 2022063152 | A1 | 3/2022 |
| WO | 2022063153 | A1 | 3/2022 |
| WO | 2022222888 | A1 | 10/2022 |
| WO | 2022222890 | A1 | 10/2022 |

OTHER PUBLICATIONS

Armenise et al.: Synthesis and antifungal activity against strains of candida albicans of 6-fluoro-4(5 or 7)-chloro-2-(difluorobenzoyl) aminobenzothiazoles.J. of Heterocyc. Chem., vol. 41, pp. 771-775, 2004.*

Deng et al. (Feb. 28, 2018) "Copper(II)-mediated, Carbon Degradation-based Amidation of Phenylacetic Acids Toward N-substituted Benzamides", Organic and Biomolecular Chemistry, 16(9):1552-1556.

Oliver et al. (Sep.-Oct. 1976) "Insect Growth Regulators. Analogues of TH-6038 and TH-6040", Journal of Agricultural and Food Chemistry, 24(5):1065-1068.

Park et al. (Jan. 1, 2017) "Chemoselective Acylation of 2-amino-8-quinolinol in the Generation of C2-amides or C8-esters", RSC Advances, 7(67):41955-41961.

Berge et al. (1977) "Pharmaceutical Salts", Journal of Pharmaceutical Sciences, 66(1):1-19.

Chen et al. (Jan. 2019) "ALPK1 Expression is Associated with Lymph Node Metastasis and Tumor Growth in Oral Squamous Cell Carcinoma Patients", The American Journal of Pathology, 189(1):190-199.

Lee et al. (May 12, 2016) "ALPK1 Phosphorylates Myosin IIA Modulating TNF-Alpha Trafficking in Gout Flares", Scientific Reports, 6(1):25740 (12 pages).

Milivojevic et al. (Feb. 21, 2017) "ALPK1 controls TIFA/TRAF6-Dependent Innate Immunity Against Heptose-1,7-Bisphosphate of Gram-Negative Bacteria", PLOS Pathogens, e1006224, 13(2):28 pages.

Rashid et al. (2019) "ALPK1 Hotspot Mutation as a Driver of Human Spiradenoma and Spiradenocarcinoma", Nature Communications, 10(1):2213 (10 pages).

Ryazanov et al. (Jan. 28, 1999) "Alpha-kinases: A New Class of Protein Kinases with a Novel Catalytic Domain", Current Biology, 9(2):R43-R45.

Ryazanov et al. (May 13, 1997) "Identification of a New Class of Protein Kinases Represented by Eukaryotic Elongation Factor-2 Kinase", Proceedings of the National Academy of Sciences, 94(10):4884-4889.

Sangiorgi et al. (2019) "Rare Missense Variants in the ALPK1 Gene May Predispose to Periodic Fever, Aphthous Stomatitis, Pharyngitis and Adenitis (PFAPA) Syndrome", European Journal of Human Genetics, 27:1361-1368.

Williams et al. (Sep. 2019) "ALPK1 Missense Pathogenic Variant in Five Families Leads to ROSAH Syndrome, an Ocular Multisystem Autosomal Dominant Disorder", Genetics in Medicine, 21(9):2103-2115.

Zhou (2018) "Alpha-Kinase 1 is a Cytosolic Innate Immune Receptor for Bacterial ADP-Heptose", Nature, 561:23 pages.

Zimmermann et al. (Sep. 5, 2017) "ALPK1- and TIFA-Dependent Innate Immune Response Triggered by the Helicobacter pylori Type IV Secretion System", Cell Reports, 20(10):2384-2395.

Corbo, Filomena et al., "Antiproliferative Activity Evaluation of a Series of N-1, 3-Benzothiazol-2-ylbenzamides as Novel Apoptosis Inducers," Journal of Chemistry Dec. 31, 2016 (Dec. 31, 2016). vol. 2016, Article 4267564.

International Search Report and the Written Opinion, mailed Dec. 23, 2021, International Patent Application No. PCT/CN2021/119802, filed Sep. 23, 2021.

(Jan. 20, 2014) RN 1525230-02-7, STN Registry, 1 page.

(2017) ACS RN 2162783-43-7 STN Registry, 5 pages.

(2020) ACS RN 2484862-72-6 STN Registry, 6 pages.

(2005) ACS RN 850402-11-8 STN Registry, 5 pages.

(Sep. 1, 2008) Chemical Abstracts Registry No. 1045395-82-1, indexed in the Registry file on STN CAS Online, 4 pages.

(Sep. 1, 2008) Chemical Abstracts Registry No. 1045399-69-6, indexed in the Registry file on STN CAS Online, 4 pages.

Extended European Search Report received in European Patent Application No. 21871521.7, mailed on Oct. 10, 2024, 12 pages.

First Office Action received in Saudi Arabia Patent Application No. 523440146, mailed on Feb. 28, 2024, 5 pages.

Office Action received in Japanese Patent Application No. 2023-518941, mailed on May 2, 2025, 10 pages.

Office Action received in Russian Patent Application No. 2023110054, mailed on Dec. 17, 2024, 69 pages.

Office Action received in Saudi Arabia Patent Application No. 523440146, mailed on Oct. 29, 2024, 9 pages.

(Sep. 8, 2001) Registry RN 1045399-69-6 and RN 1045395-82-1, 1 page.

(May 13, 2005) RN: 2484862-72-6, STN Regestry, 3 pages.

RN: 2637370-96-6, STN Registry, Apr. 23, 2021 and RN: 2144340-55-4, STN Registry, Nov. 20, 2017, 1 page.

Aghekyan et al. (2004) "Synthesis of 4-[1-(3,4-dimethoxyphenyl)cyclopentyl]- and 4-[4-(3,4-dimethoxyphenyl)-4-tetrahydropyran-4-yl]-2-aminothiazoles", Hayastani Kimiakan Handes, 57(3):85-89 (10 pages).

Bezençon et al. (Dec. 14, 2017) "Discovery of a Potent, Selective T-type Calcium Channel Blocker as a Drug Candidate for the Treatment of Generalized Epilepsies", Journal of Medicinal Chemistry, 60(23):9769-9789 (65 pages).

(Jun. 3, 2002) Database Registry, "CAS Registry No. 424798-58-3", Chemical Abstracts Services, 1 page.

Inoue et al. (2012) "Synthesis and SAR study of new thiazole derivatives as vascular adhesion protein-1 (VAP-1) inhibitors for the treatment of diabetic macular edema", Bioorganic & Medicinal Chemistry, 21(5):1219-1233 (47 pages.).

Kummerer Klaus (Nov. 2010) "Pharmaceuticals in the Environment", Annual Review of Environment and Resources, (35):57-75.

Park et al. (2005) "Non-peptidic small molecule inhibitors of XIAP", Bioorganic & Medicinal Chemistry Letters, 15(3):771-775.

International Search Report & Written Opinion received in PCT Application No. PCT/CN2021/119801, mailed on Dec. 21, 2021, 12 Pages.

Straub Christopher S. (2011) "Targeting IAPs as An Approach to Anti-Cancer Therapy", Current Topics in Medicinal Chemistry, 11(3):291-316.

* cited by examiner

BENZOTHIAZOLE AND QUINOLINE DERIVATIVES AND THEIR USE

CROSS-REFERENCE TO RELATED APPLICATIONS

This application is a national stage entry, filed under 35 U.S.C. § 371, of International Application No. PCT/CN2021/119802, filed on Sep. 23, 2021, which claims the benefit of International Application No. PCT/CN2020/117437, filed on Sep. 24, 2020, the entire contents of which are hereby incorporated herein by reference in their entireties and for all purposes.

FIELD OF THE INVENTION

The present invention relates to benzothiazole and quinoline derivatives having activity as inhibitors of alpha protein kinase 1 (ALPK1) and methods for their use in therapy.

BACKGROUND

Alpha-kinases display little sequence similarity to conventional protein kinases. A total of six alpha kinase members have been identified. These include alpha-protein kinase 1 (ALPK1), ALPK2, ALPK3, elongated factor-2 kinase (eEF2K), and transient receptor potential cation channel M6 and M7 (TRPM6 and TRPM7). See Ryazanov et al., *Curr Biol* 9:R43-45 (1999) and Ryazanov et al., *Proc Natl Acad Sci USA* 94:4884-4889 (1997).

ALPK1 is an intracytoplasmic serine threonine protein kinase that plays an important role in activating the innate immune response to bacteria via TRAF-interacting protein with forkhead-associated domain (TIFA) dependent proinflammatory nuclear factor-kappa-B (NFkB) signaling. See Zimmermann et al. *Cell Rep.* 20:2384-2395 (2017); Milivojevic et al., *PLoS Pathog.* 13:E1006224-E1006224 (2017); and Zhou et al., *Nature* 561:122-126 (2018).

Inappropriate activation of ALPK1 signaling has been implicated in diseases and disorders associated with excessive or inappropriate inflammation. For example, ALPK1 has been implicated in monosodium urate monohydrate (MSU)-induced inflammation and gout. Lee et al., *Sci. Rep.* 6:25740-25740(2016). Elevated ALPK1 expression has also been associated with lymph node metastasis and tumor growth in oral squamous cell carcinoma. Chen et al., *Am J Pathol* 189:190-199 (2019). In addition, genetic mutations in ALPK1 have been associated with spiroandenoma, spiroandenocarcinoma, "Retinal dystrophy, Optic nerve edema, Splenomegaly, Anhidrosis and migraine Headache" ("ROSAH") syndrome, and "Periodic Fever, Aphthous Stomatitis, Pharyngitis, and Adenitis" ("PFAPA") syndrome. See e.g., Rashid et al., *Nature Communications* (2019); Williams et al., *Genetics in Medicine* 21:2103-2115 (2019); and Sangiorgi et al. *Eur. J. Human Genetics* (2019).

SUMMARY OF THE DISCLOSURE

The disclosure provides compounds of Formula I and II, and subembodiments of Formula I and II described herein, that are inhibitors of ALPK1 kinase activity, and related compositions and methods.

In some aspects, provided herein are compounds of Formula (I) having the structure of (I)

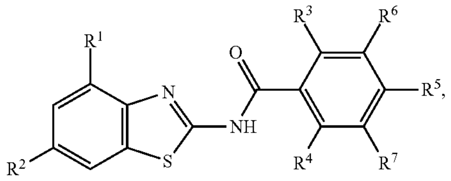

or a salt thereof, wherein $R^1$, $R^2$, $R^3$, $R^4$, $R^5$, $R^6$, and $R^7$ are as defined herein.

In some embodiments, compounds of Formula (I) are represented by Formula (I-A), (I-A)

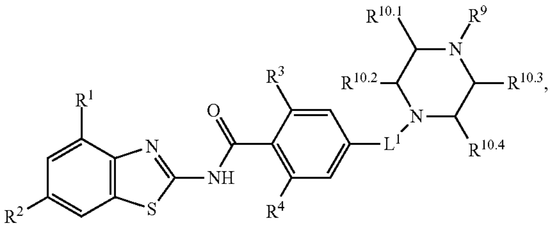

wherein $R^1$, $R^2$, $R^3$, $R^4$, $L^1$, $R^9$, $R^{10.1}$, $R^{10.2}$, $R^{10.3}$ and $R^{10.4}$ are as defined herein.

In some embodiments, compounds of Formula (I) are represented by Formula (I-B), (I-B)

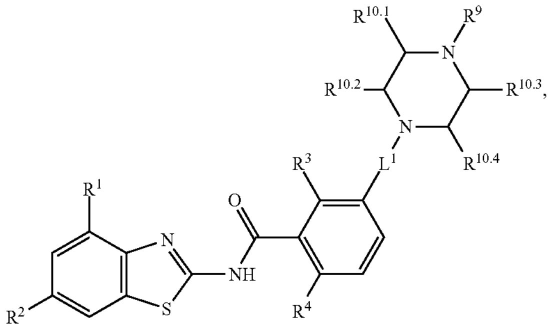

wherein $R^1$, $R^2$, $R^3$, $R^4$, $L^1$, $R^9$, $R^{10.1}$, $R^{10.2}$, $R^{10.3}$ and $R^{10.4}$ are as defined herein.

In some embodiments, compounds of Formula (I) are represented by Formula (I-C), (I-C)

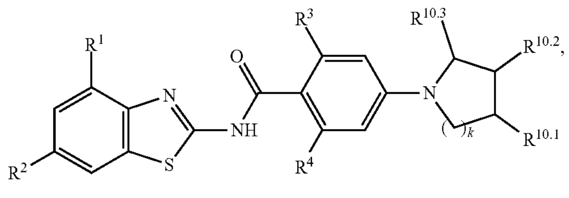

wherein $R^1$, $R^2$, $R^3$, $R^4$, k, $R^9$, $R^{10.1}$, $R^{10.2}$, and $R^{10.3}$ are as defined herein.

In some embodiments, compounds of Formula (I) are represented by Formula (I-D), (I-D)

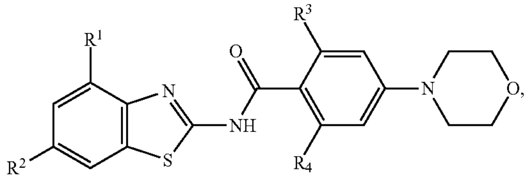

wherein $R^1$, $R^2$, $R^3$, and $R^4$ are as described above.

In some aspects, provided herein are compounds Formula (II) having the structure of:

(II)

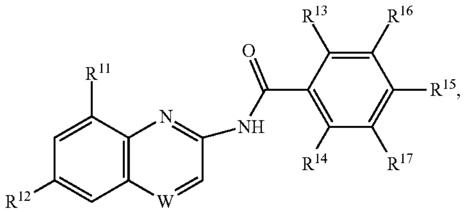

or a salt thereof, wherein $R^{11}$, $R^{12}$, $R^{13}$, $R^{14}$, $R^1$, $R^{16}$, and $R^{17}$ are as defined herein.

In some embodiments, compounds of Formula (II) are represented by Formula (II-A) or (II-B), (II-A)

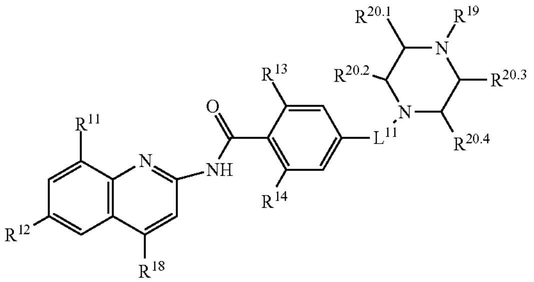

or (II-B)

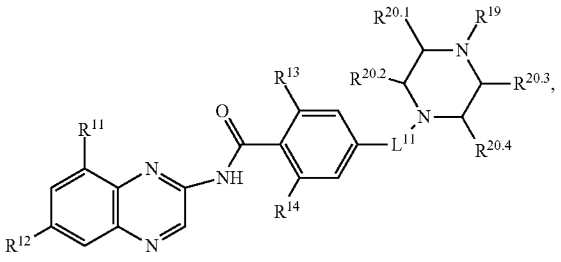

wherein $R^{11}$, $R^{12}$, $R^{13}$, $R^{14}$, $L^{11}$, $R^{19}$, $R^{20.1}$, $R^{20.2}$, $R^{20.3}$ and $R^{20.4}$ are as defined herein.

In some embodiments, compounds of Formula (II) are represented by Formula (II-C) or (II-D), (II-C)

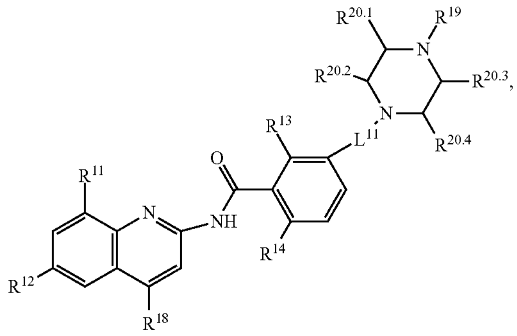

or (II-D)

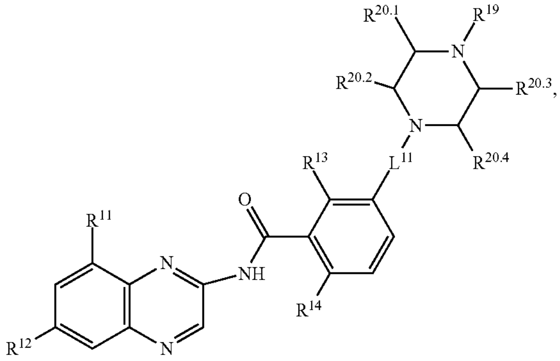

wherein $R^{11}$, $R^{12}$, $R^{13}$, $R^{14}$, $L^{11}$, $R^{19}$, $R^{20.1}$, $R^{20.2}$, $R^{20.3}$ and $R^{20.4}$ are as defined herein.

In some embodiments, compounds of Formula (II) are represented by Formula (II-E) or (II-F), (II-E)

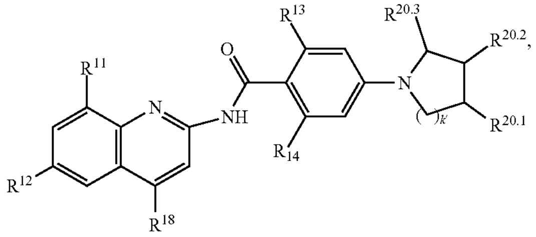

or (II-F)

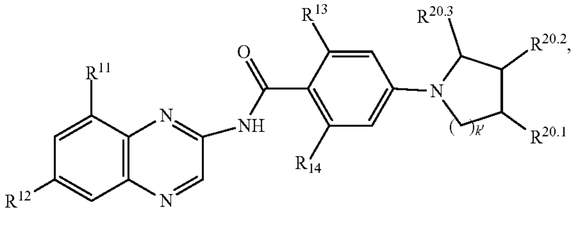

$R^{11}$, $R^{12}$, $R^{13}$, $R^{14}$, $R^{20.1}$, $R^{20.2}$, and $R^{20.3}$ are as defined herein.

In embodiments, the disclosure provides a pharmaceutical composition comprising a compound of Formula (I) or (II), or a subembodiment thereof, as described herein, or a pharmaceutically acceptable salt thereof.

In embodiments, the disclosure provides a method for inhibiting ALPK1 kinase activity in a cell or tissue of a subject in need of such therapy, the method comprising administering to the subject a compound of Formula (I) or (II), or a subembodiment thereof, as described herein.

In embodiments, the disclosure provides a method for inhibiting or reducing inflammation in a target tissue of a subject in need of such treatment, the method comprising administering to the subject a compound of Formula (I) or (II), or a subembodiment thereof, as described herein.

In embodiments, the disclosure provides a method for treating a disease, disorder, or condition characterized by excessive or inappropriate ALPK1-dependent proinflammatory signaling in a subject in need of such therapy, the method comprising administering to the subject a compound of Formula (I) or (II), or a subembodiment thereof, as described herein.

In embodiments, the disease, disorder, or condition is selected from systemic lupus erythematosus (SLE), sepsis, a cancer, spiroandenoma, spiroandenocarcinoma, "Retinal dystrophy, Optic nerve edema, Splenomegaly, Anhidrosis and migraine Headache" ("ROSAH") syndrome, and "Periodic Fever, Aphthous Stomatitis, Pharyngitis, and Adenitis" ("PFAPA") syndrome.

In embodiments, the cancer is selected from lung cancer, colon cancer, and oral squamous cancer.

In embodiments, the disease or disorder is selected from ROSAH and PFAPA.

In embodiments, the disease or disorder is systemic lupus erythematosus (SLE).

In embodiments, the disease or disorder is sepsis.

In embodiments, the disease or disorder is spiradenoma or spiroandenocarcinoma.

In embodiments, the subject in need of such therapy or treatment is a subject carrying one or more genetic mutations in ALPK1. In embodiments, at least one mutation is an ALPK1 activating mutation.

DETAILED DESCRIPTION

Figure 1:
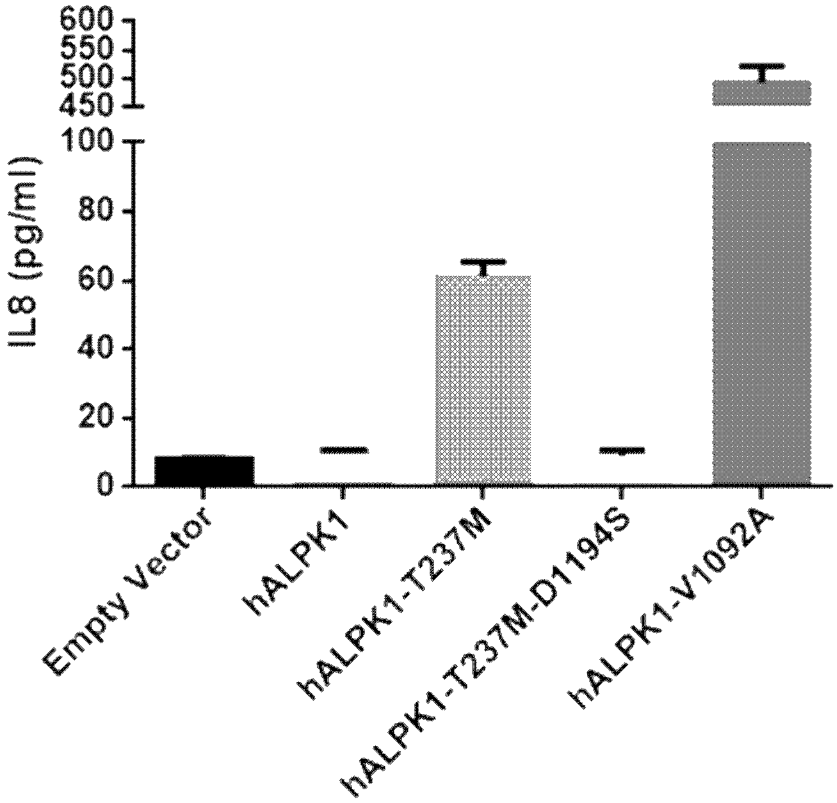
FIG. 1: Bar graph showing IL-8 secretion (pg/ml) in HEK293 cells transiently transfected with empty vector or expression vectors encoding human ALPK1 (hALPK1), an activating mutation in hALPK1 (T237M or V1092A) or an activating mutation combined with a kinase dead mutation in ALPK1 (hALPK1-T237M-D1194S).

The disclosure provides compounds that are inhibitors of ALPK1, compositions comprising same, and methods for their use in therapy.

The term "ALPK1" is used herein to refer interchangeably to isoform 1 (Q96QP1-1) or the alternative splice variant isoform 2 (Q96QP1-2) of the human sequence identified by UniProtKB-Q96QP1 (ALPK1_HUMAN).

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like.

An unsaturated alkyl group, "alkenyl" or "alkynyl", is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. In some embodiments, an alkenyl group has 1 double bond. Alkenyl groups can be substituted or unsubstituted.

As used herein, "alkynyl" refers to a straight chain or branched hydrocarbon having at least 2 carbon atoms and at least one triple bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkynyl groups can have any suitable number of triple bonds, including, but not limited to, 1, 2, 3, 4, 5 or more. In some embodiments, an alkynyl group has 1 triple bond. Alkynyl groups can be substituted or unsubstituted.

As used herein, the term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)n$-, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted. In some embodiments, alkylene groups are substituted with 1-2 substituents. As a non-limiting example, suitable substituents include halogen and hydroxyl.

An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

As used herein, the term "alkoxy" or "alkoxyl" refers to an alkyl group having an oxygen atom that connects the alkyl group to the point of attachment: alkyl-O—. As for alkyl group, alkoxyl groups can have any suitable number of carbon atoms, such as C1-6. Alkoxyl groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be substituted or unsubstituted.

As used herein, the term "alkenyloxy" or "alkenyloxyl" refers to an alkenyl group, as defined above, having an oxygen atom that connects the alkenyl group to the point of attachment: alkenyl-O—. Alkenyloxyl groups can have any suitable number of carbon atoms, such as C1-6. Alkenyloxyl groups can be further substituted with a variety of substituents described within. Alkenyloxyl groups can be substituted or unsubstituted.

As used herein, the term "aminoalkyl" means a linear monovalent hydrocarbon radical of one to six carbon atoms or a branched monovalent hydrocarbon radical of three to six carbons substituted with —NR'R" where R' and R" are independently hydrogen, alkyl, haloalkyl, or hydroxyalkyl, each as defined herein, e.g., aminomethyl, aminoethyl, methylaminomethyl, and the like.

As used herein, the term "hydroxyalkyl" refers to an alkyl radical wherein at least one of the hydrogen atoms of the alkyl radical is replaced by OH. Examples of hydroxyalkyl include, but are not limited to, hydroxy-methyl, 2-hydroxy-ethyl, 2-hydroxy-propyl, 3-hydroxy-propyl and 4-hydroxy-butyl.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—$S(O)_2$—$CH_3$, —CH═CH—O—$CH_3$, —$Si(CH_3)_3$, —$CH_2$—CH═N—$OCH_3$, —CH═CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—$Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)2R'— represents both —C(O)2R'— and —R'C(O)2-. As described above, heteroalkyl groups, as used herein, include those groups that are attached to the remainder of the molecule through a heteroatom, such as —C(O)R', —C(O)NR', —NR'R", —OR', —SR', and/or —SO2R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

As used herein, "saturated or unsaturated" refers to a cyclic system where two of the atoms in the group may be bound to one another by a single bond, a double bond, or a triple bond. Saturated moieties are those having only single bonds, where moieties having multiple bonds (e.g., at least one double bond or at least one triple bond are referred to as unsaturated.

As used herein, "cycloalkyl" refers to a saturated ring assembly containing from 3 to 10 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$. Cycloalkyl rings can be saturated or unsaturated, when unsaturated cycloalkyl rings can have one or two double bonds. Cycloalkyl rings include, for example, cyclopropyl, cyclobutyl, cyclopentyl, cyclohexyl, and cyclooctyl. Cycloalkyl groups can be substituted or unsubstituted. In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. As used herein, the term"heterocyclyl", "heterocyclic", or "heterocycloalkyl" refers to a heterocyclic group that is saturated or partially saturated and is a monocyclic or a polycyclic ring; which has 3 to 16, most preferably 5 to 10 and most preferably 1 or 4 ring atoms; wherein one or more, preferably one to four, especially one or two ring atoms are a heteroatom selected from oxygen, nitrogen and sulfur (the remaining ring atoms therefore being carbon). The term heterocyclyl excludes heteroaryl. The heterocyclic group can be attached to the rest of the molecule through a heteroatom, selected from oxygen, nitrogen and sulfur, or a carbon atom. The heterocyclyl can include fused or bridged rings as well as spirocyclic rings. Examples of heterocyclyl include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

As used herein, "spiroheterocyclyl" refers to a specific bicyclic heterocyclic group wherein the 2 ring systems are connected through a single carbon atom. For example, the term"spiroheterocyclyl" can refer to a 6-10 spiro heterocyclyl. Examples of include, but not limited to, 6,9-diazaspiro[4.5]decane, 2-oxa-6,9-diazaspiro[4.5]decane, 2-Oxa-6-azaspiro[3.4]octane, 6-azaspiro[3.4]octane, 2,6-diazaspiro[3.4]octane, 1,6-diazaspiro[3.4]octane, 2,8-diazaspiro[4.5]decane, 2,7-diazaspiro[4.4]nonane, 1-thia-8-azaspiro[4.5]decane 1,1-dioxide, 1-oxa-7-azaspiro[4.4]nonane and 1-oxa-9-azaspiro[5.5]undecane.

As used herein, "bridged heterocyclyl" refers to a $C_{3-6}$ cycloalkyl ring or a 3- to 6-membered heterocyclyl ring, as defined above, where two non-adjacent ring vertices ("bridgehead atoms") of the cycloalkyl ring or the heterocyclyl ring are linked to form an additional cyclic moiety (a "bridge"). The bridge comprises 1 to 4 ring vertices, not including the bridgehead atoms. Examples include, but not limited to, 2,5-diazabicyclo[2.2.1]heptane, 3,6-diazabicyclo[3.1.1]heptane, 3,8-diazabicyclo[3.2.1]octane, 2,5-diazabicyclo[2.2.2]octane, 3,9-diazabicyclo[3.3.1]nonane, 2-thia-5-azabicyclo[2.2.1]heptane 2,2-dioxide, 2-azabicyclo[2.2.1]hept-5-ene, 3-oxa-8-azabicyclo[3.2.1]octane, 3-oxa-6-azabicyclo[3.1.1]heptane, 6-oxa-3-azabicyclo[3.1.1]heptane and 2-oxa-5-azabicyclo[2.2.1]heptane.

The term "bicyclic heterocyclyl" refers to a heterocyclic group as defined above where the two ring systems are connected through two adjacent ring vertices (e.g., a fused ring system). Typical "bicyclic heterocyclyl" rings include 6 to 11 ring members having 1 to 4 heteroatom ring vertices selected from N, O, and S (the remaining ring atoms therefore being carbon). Examples include, but not limited to, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydroisobenzofuranyl, dihydrobenzothienyl, dihydrobenzothiopyranyl, dihydrobenzothiopyranyl sulfone, indolinyl, indolyl, isochromanyl, isoindolinyl, isoquinolinyl, isothiazolidinyl, naphthyridinyl, pyrazolopyridinyl, quinazolinyl, quinolinyl, quinoxalinyl, tetrahydroisoquinolinyl, tetrahydroquinolinyl.

As used herein, the term "halogen" or "halo" refers to fluorine, chlorine, bromine and iodine.

Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

As used herein, the term "haloalkoxyl" or "haloalkoxy" refers to an alkoxyl group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens.

As used herein, the term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Additional heteroatoms can also be useful, including, but not limited to, B, Al, Si and P. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 9 ring members and from 1 to 4 heteroatoms, or from 5 to 9 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), purine. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The term "heteroaryl" also includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

When needed, any definition herein may be used in combination with any other definition to describe a composite structural group. By convention, the trailing element of any such definition is that which attaches to the parent moiety. For example, the composite group cycloalkoxyl means that a cycloalkyl group is attached to the parent molecule through an oxyl group.

The symbol " " denotes the point of attachment of a chemical moiety to the remainder of a molecule or chemical formula.

The term "oxo" as used herein, means an oxygen atom connected to the point of attachment by a double bond (═O).

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")═NR"", —NR—C(NR'R")═NR'", —S(O)R', —S$(O)_2$R', —S$(O)_2$NR'R", —NR$SO_2$R', —NR'NR"R'", —ONR'R", —NR'C(O)NR"NR'"R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")═NR"", —NR—C(NR'R")═NR'", —S(O)R', —S$(O)_2$R', —S$(O)_2$NR'R", —NR$SO_2$R', —NR'NR"R'", —ONR'R", —NR'C(O)NR"NR'"R"", —CN, —$NO_2$, —R', —$N_3$, —$CH(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)$_p$—(CRR')$_q$-U-, wherein T and U are independently —NR—, —O—, —CRR'—, or a single bond, and each p and q is independently an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHN$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from the groups in (i).

Certain compounds of the present disclosure possess asymmetric carbon atoms (optical centers) or double bonds; the racemates, diastereomer, geometric isomers, regioisomers and individual isomers (e.g., separate enantiomers) are all intended to be encompassed within the scope of the present disclosure. In some embodiments, the compounds of the present disclosure are a particular enantiomer, anomer, or diastereomer substantially free of other forms.

As used herein, the term "substantially free" refers to an amount of 10% or less of another isomeric form, preferably 8%, 5%, 4%, 3%, 2%, 1%, 0.5%, or less of another form. In some embodiments, the isomer is a stereoisomer.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^1$ and $R^{13}$) are allowed to contact such that the leaving groups are sufficiently proximal to react, interact or physically touch. In embodiments, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

The term "solution" is used in accordance and refers to a liquid mixture in which the minor component (e.g., a solute or compound) is uniformly distributed within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "bind" and "bound" as used herein is used in accordance with its plain and ordinary meaning and refers to the association between atoms or molecules. The association can be direct or indirect. For example, bound atoms or molecules may be direct, e.g., by covalent bond or linker (e.g. a first linker or second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "capable of binding" as used herein refers to a moiety (e.g. a compound as described herein) that is able to measurably bind to a target (e.g., a NF-κB, a Toll-like receptor protein). In embodiments, where a moiety is capable of binding a target, the moiety is capable of binding with a $K_d$ of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

The term "$EC_{50}$" or "half maximal effective concentration" as used herein refers to the concentration of a molecule (e.g., drug, small molecule, antibody, antagonist, or specific inhibitor) capable of inducing a response which is halfway between the baseline response (e.g., no treatment or effect) and the maximum response after a specified exposure time. In embodiments, the $EC_{50}$ is the concentration of a molecule (e.g., antibody, chimeric antigen receptor or bispecific antibody) that produces 50% of the maximal possible effect of that molecule.

The term "$IC_{50}$" or "half maximal inhibitory concentration" as used herein refers to the concentration of a molecule (e.g., drug, small molecule, antibody, antagonist, or specific inhibitor) capable of inhibiting a specific biological process or biochemical activity of a response which is halfway between the baseline response (e.g. no inhibition) and the maximum response after a specified exposure time. In embodiments, the $IC_{50}$ is the concentration of a molecule (e.g., drug, small molecule, antibody, antagonist, or specific inhibitor) that produces 50% of the maximal possible inhibition of that molecule.

An “inhibitor” refers to a compound (e.g. compounds described herein) that reduces activity when compared to a control, such as absence of the compound or a compound with known inactivity.

As defined herein, the term “activation”, “activate”, “activating”, “activator” and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms “agonist,” “activator,” “upregulator,” etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term “inhibition”, “inhibit”, “inhibiting” and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms “inhibitor,” “repressor” or “antagonist” or “downregulator” interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term “associated” or “associated with” in the context of a substance or substance activity or function associated with a disease (e.g. a protein associated disease, a cancer (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease.

In this disclosure, “comprises,” “comprising,” “containing” and “having” and the like can have the meaning ascribed to them in U.S. Patent law and can mean “includes,” “including,” and the like. “Consisting essentially of or “consists essentially” likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Compounds

Provided herein are, inter alia, compounds having a structure of Formula (I) or Formula (II), or a salt (e.g., a pharmaceutically acceptable salt) thereof.

In an aspect, a compound has a structure of:

(I)

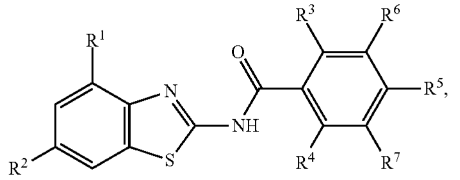

or a salt thereof, wherein:

$R^1$ is hydrogen, halogen, —$CX_3$, —$CHX_2$, —$CH_2X$, —$OCX_3$, —$OCH_2X$, —$OCHX_2$, —$OR^{1A}$, substituted or unsubstituted $C_1$-$C_6$ alkyl, substituted or unsubstituted 2 to 6 membered heteroalkyl, or substituted or unsubstituted $C_3$-$C_6$ cycloalkyl;

$R^2$ is hydrogen or halogen;

Each $R^3$ and $R^4$ is independently halogen, —$OR^{3A}$, or unsubstituted $C_1$-$C_6$ alkyl;

$R^5$ is hydrogen, —$NR^{5B}R^{5C}$, —$(CH_2)_{n5}NR^{5B}R^{5C}$, —$C(O)NR^{5B}R^{5C}$, —$O(CH_2)_{m5}OR^{5A}$, —$C(O)OR^{5A}$, —$OR^{5A}$, —CN, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 5 to 6 membered heterocycloalkyl, substituted or unsubstituted $C_6$-$C_{12}$ aryl, or substituted or unsubstituted 5 to 6 membered heteroaryl;

$R^6$ is hydrogen, —$NR^{6B}R^{6C}$, —$(CH_2)_{n6}NR^{6B}R^{6C}$, —$C(O)NR^{6B}R^{6C}$, —$O(CH_2)_{m6}OR^{6A}$, —$C(O)OR^{6A}$, —$OR^{6A}$, —CN, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 5 to 6 membered heterocycloalkyl, substituted or unsubstituted $C_6$-$C_{12}$ aryl, or substituted or unsubstituted 5 to 6 membered heteroaryl;

$R^7$ is hydrogen, $—NR^{7B}R^{7C}$, $—(CH_2)_{n7}NR^{7B}R^{7C}$, $—C(O)NR^{7B}R^{7C}$, $—O(CH_2)_{m7}OR^{7A}$, $—C(O)OR^{7A}$, $—OR^{7A}$, —CN, substituted or unsubstituted $C_1$-$C_7$ alkyl, substituted or unsubstituted 2 to 7 membered heteroalkyl, substituted or unsubstituted $C_3$-$C_6$ cycloalkyl, substituted or unsubstituted 5 to 6 membered heterocycloalkyl, substituted or unsubstituted $C_6$-$C_{12}$ aryl, or substituted or unsubstituted 5 to 6 membered heteroaryl;

X is independently —F, —Cl, —Br or —I;

Each n5, n6, and n7 is independently an integer of 1 to 4;

Each m5, m6, and m7 is independently an integer of 1 to 4; and

Each $R^{1A}$, $R^{3A}$, $R^{5A}$, $R^{5B}$, $R^{5C}$, $R^{6A}$, $R^{6B}$, $R^{6C}$, $R^{7A}$, $R^{7B}$, and $R^{7C}$ are independently hydrogen, substituted or unsubstituted $C_1$-$C_4$ alkyl, or substituted or unsubstituted 2 to 4 membered heteroalkyl, or $R^{5B}$ and $R^{5C}$ together with atoms attached thereto are optionally joined to form a substituted or unsubstituted 5 to 6 membered heterocycloalkyl, or substituted or unsubstituted heteroaryl; $R^{6B}$ and $R^{6C}$ together with atoms attached thereto are optionally joined to form a substituted or unsubstituted 5 to 6 membered heterocycloalkyl, or substituted or unsubstituted heteroaryl; or $R^{7B}$ and $R^{7C}$ together with atoms attached thereto are optionally joined to form a substituted or unsubstituted 5 to 6 membered heterocycloalkyl or substituted or unsubstituted heteroaryl.

In some embodiments, $R^2$ is hydrogen or halogen. In some embodiments, $R^2$ is hydrogen. In some embodiments, $R^2$ is —F, —Cl, or Br.

In some embodiments, each $R^3$ and $R^4$ is independently halogen, or unsubstituted $C_1$-$C_4$ alkyl. In some embodiments, $R^3$ is halogen, or unsubstituted $C_1$-$C_4$ alkyl. In some embodiments, $R^4$ is halogen, or unsubstituted $C_1$-$C_4$ alkyl. In some embodiments, each $R^3$ and $R^4$ is independently —F, —Cl, or methyl. In some embodiments, $R^3$ is —F, —Cl, or methyl. In some embodiments, $R^4$ is —F, —Cl, or methyl.

In some embodiments, $R^6$ and $R^7$ are hydrogen. In some embodiments, $R^{5B}$ and $R^{5C}$ together with atoms attached thereto are joined to form a substituted or unsubstituted piperazinyl. In some embodiments, $R^6$ and $R^7$ are hydrogen; and $R^{5B}$ and $R^{5C}$ together with atoms attached thereto are joined to form a substituted or unsubstituted piperazinyl.

In some embodiments, the compound has a structure of:

(I-A)

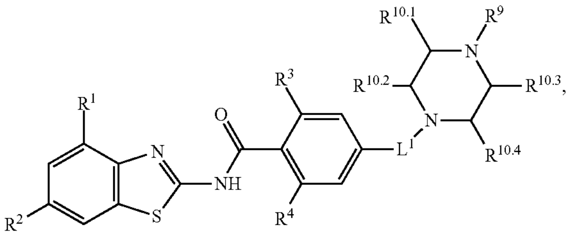

wherein:

$L^1$ is a bond, —C(O)—, or $—(CH_2)_{n5}$;

$R^9$ is hydrogen, $—(CH_2)_mOH$, $—(CH_2)_m(C_6H_5)$, $—C(O)NR^{9B}R^{9C}$, substituted or unsubstituted $C_1$-$C_6$ alkyl, or substituted or unsubstituted 2 to 6 membered heteroalkyl;

Each $R^{10.1}$, $R^{10.2}$, $R^{10.3}$ and $R^{10.4}$ is independently hydrogen, $—OR^{10A}$, $—C(O)OR^{10A}$, $—NR^{10B}R^{10C}$, $—(CH_2)_mOH$, substituted or unsubstituted $C_1$-$C_6$ alkyl, substituted or unsubstituted 2 to 6 membered heteroalkyl, or substituted or unsubstituted $C_3$-$C_6$ cycloalkyl, or one or more of $R^{10.1}$, $R^{10.2}$, $R^{10.3}$, and $R^{10.4}$ are optionally joined to each other or to atoms of the piperazinyl ring to form a substituted or unsubstituted heterocycloalkyl;

Each m is independently an integer of 1 to 4; and

Each $R^{9B}$, $R^{9C}$, $R^{10A}$, $R^{10B}$ and $R^{10C}$ are independently hydrogen, substituted or unsubstituted $C_1$-$C_4$ alkyl, substituted or unsubstituted 2 to 4 membered heteroalkyl, substituted or unsubstituted 5 to 6 membered heterocycloalkyl, or substituted or unsubstituted 5 to 6 membered heteroaryl.

In Formula (I-A), $R^1$, $R^2$, $R^3$, and $R^4$ are as described above.

In some embodiments, $L^1$ is a bond, —C(O)—, methylene, or ethylene. In some embodiments, $L^1$ is a bond. In some embodiments, $L^1$ is —C(O)—. In some embodiments, $L^1$ is methylene. In some embodiments, $L^1$ is ethylene.

In some embodiments, $R^9$ is hydrogen, unsubstituted $C_1$-$C_4$ alkyl, or $—C(O)NR^{9B}R^{9C}$. $R^{9B}$ and $R^{9C}$ are independently hydrogen, substituted or unsubstituted $C_1$-$C_4$ alkyl, substituted or unsubstituted 2 to 4 membered heteroalkyl, substituted or unsubstituted 5 to 6 membered heterocycloalkyl, or substituted or unsubstituted 5 to 6 membered heteroaryl. In some embodiments, $R^{9B}$ and $R^{9C}$ are independently hydrogen, or unsubstituted $C_1$-$C_4$ alkyl.

In some embodiments, $L^1$ is a bond, —C(O)—, methylene, or ethylene; and $R^9$ is hydrogen, unsubstituted $C_1$-$C_4$ alkyl, or $—C(O)NR^{9B}R^{9C}$.

In some embodiments, $L^1$ is a bond. In some embodiments, $R^9$ is hydrogen, methyl, ethyl, propyl, $—C(O)NH_2$,

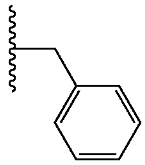
, or
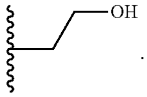
.

In some embodiments, $L^1$ is a bond; and $R^9$ is hydrogen, methyl, ethyl, propyl, $—C(O)NH_2$,

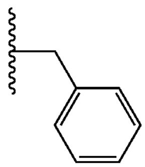
, or
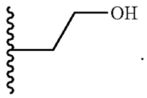
.

In some embodiments, each $R^{10.1}$, $R^{10.2}$, $R^{10.3}$, and $R^{10.4}$ is independently hydrogen, oxo, or unsubstituted $C_1$-$C_4$ alkyl, —C(O)OH, or $—CH_2OH$. In some embodiments, $R^{10.1}$ is hydrogen, oxo, or unsubstituted $C_1$-$C_4$ alkyl, —C(O)OH, or $—CH_2OH$. In some embodiments, $R^{10.2}$ is independently hydrogen, oxo, or unsubstituted $C_1$-$C_4$ alkyl, —C(O)OH, or $—CH_2OH$. In some embodiments, $R^{10.3}$ is independently hydrogen, oxo, or unsubstituted $C_1$-$C_4$ alkyl, —C(O)OH, or —$CH_2$OH. In some embodiments, $R^{10.4}$ is independently hydrogen, oxo, or unsubstituted $C_1$-$C_4$ alkyl, —C(O)OH, or —$CH_2$OH.

In some embodiments, $L^1$ is a bond; and $R^{10.1}$, $R^{10.2}$, $R^{10.3}$ and $R^{10.4}$ are hydrogen. In some embodiments, the compound is:

(I-A-1)

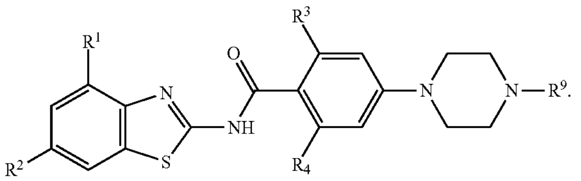

$R^1$, $R^2$, $R^3$, and $R^4$ are as described above.

In some embodiments, $R^1$ is hydrogen, halogen, unsubstituted $C_1$-$C_4$ alkyl, unsubstituted $C_3$-$C_6$ cycloalkyl, —$OCX_3$, —$OCH_2X$, —$OCHX_2$, or —$OR^{1A}$; and $R^{1A}$ is hydrogen or unsubstituted $C_1$-$C_4$ alkyl. In some embodiments, $R^1$ is hydrogen, methyl, ethyl, —C≡CH, —C≡CH—$CH_3$, —OH, —$OCH_3$, —$OCHF_2$, —$OCH_2F$, —$OCF_3$, —F, —Cl, or —Br. In embodiments, $R^2$ is hydrogen. In embodiments, $R^2$ is —F, —Cl, or —Br.

In some embodiments, $R^9$ is hydrogen, unsubstituted $C_1$-$C_4$ alkyl, or —C(O)$NR^{9B}R^{9C}$. In some embodiments, $R^9$ is hydrogen, methyl, ethyl, propyl, or —C(O)$NH_2$.

For example, the compound of formula (I-A-1) is:

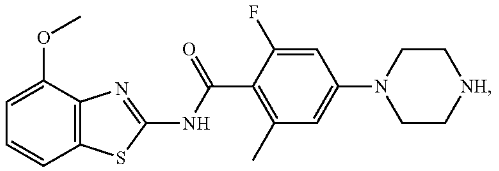

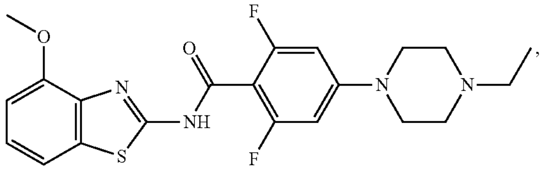

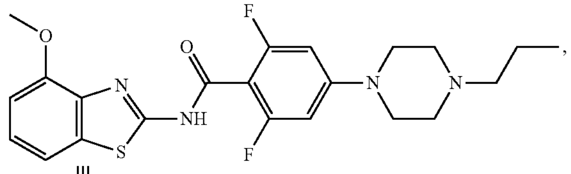

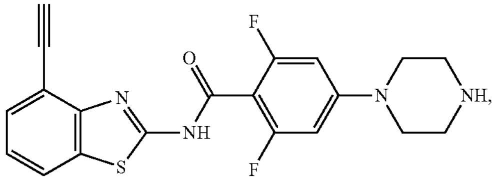

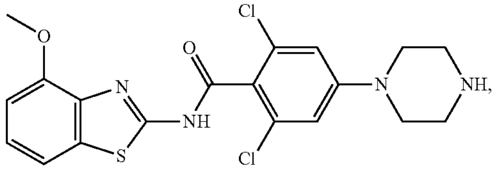

-continued

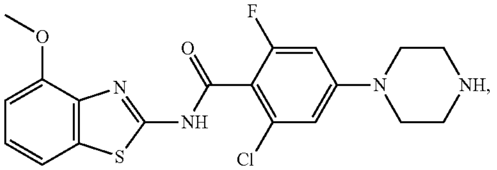

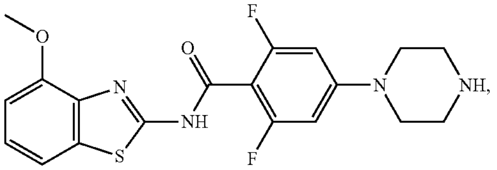

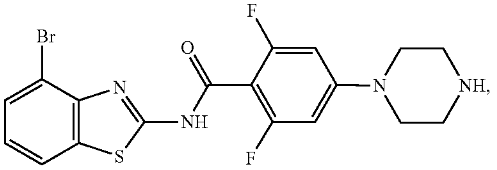

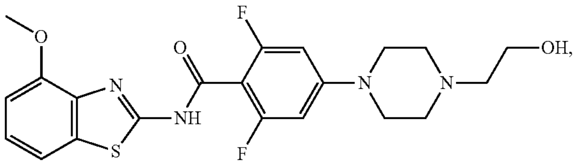

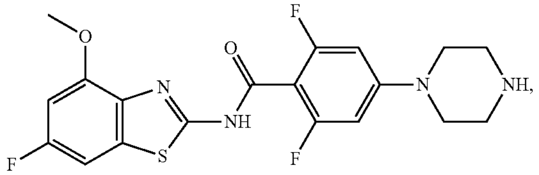

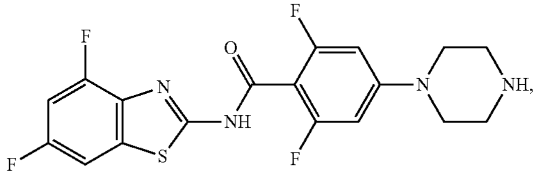

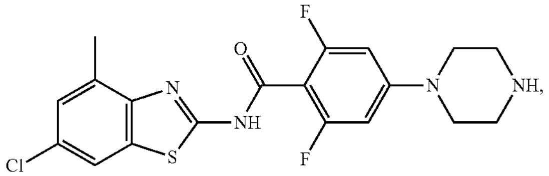

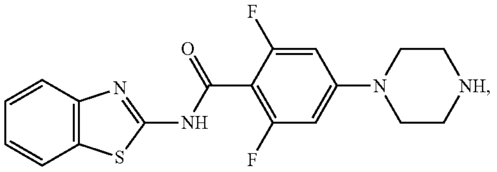

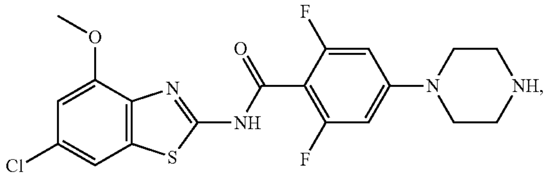

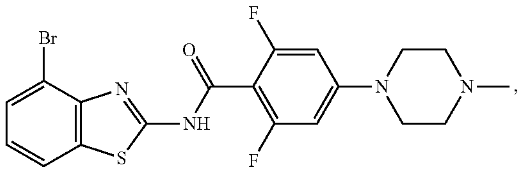

-continued

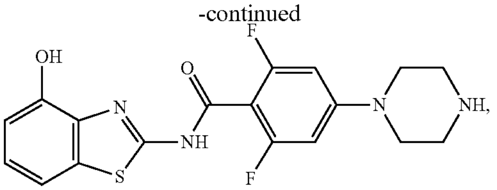

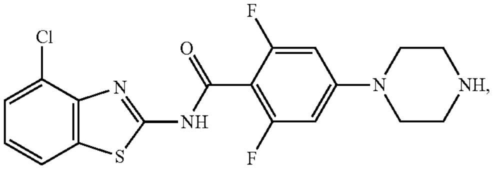

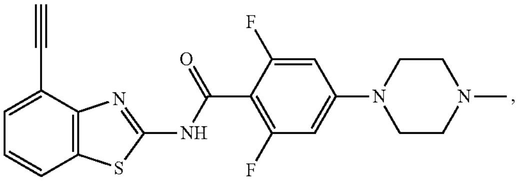

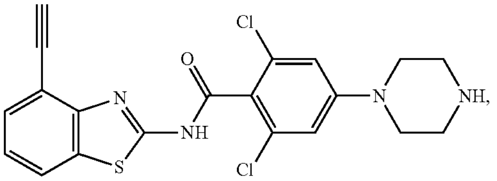

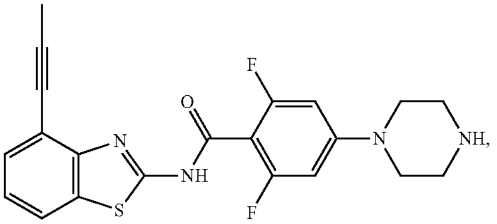

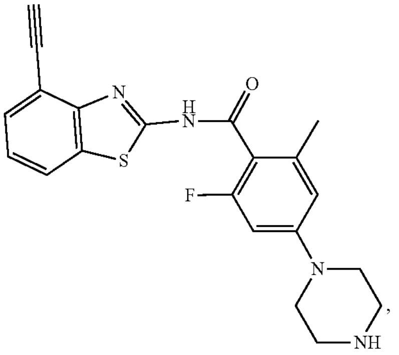

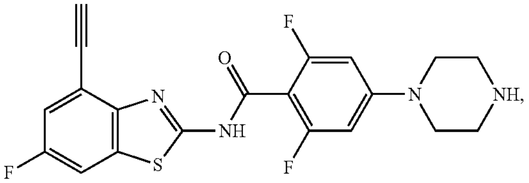

or

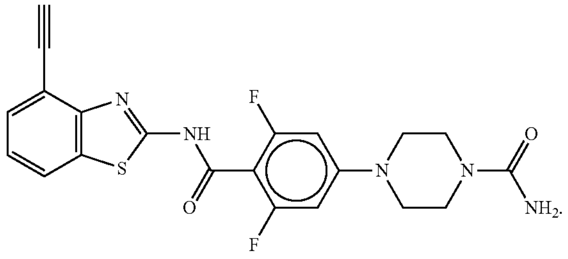

In some embodiments, the compound is (I-A-1a)

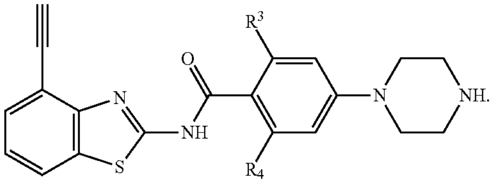

In some embodiments, in formula (I-A-1a), each $R^3$ and $R^4$ are independently is —F, —Cl, —Br, or methyl. In some embodiments, the compound of formula (I-A-1a) is

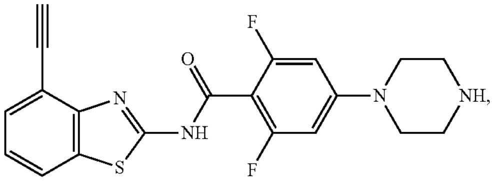

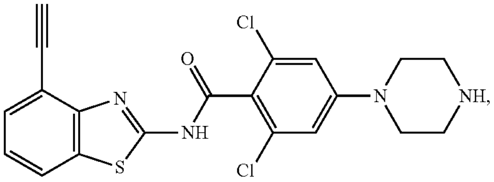

or

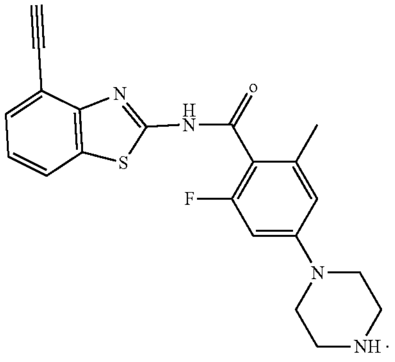

In some embodiments, $L^1$ is a bond; $R^9$ is hydrogen; and at least one of $R^{10.1}$, $R^{10.2}$, $R^{10.3}$ and $R^{10.4}$ is not hydrogen. In some embodiments, $L^1$ is a bond; and one of $R^{10.1}$, $R^{10.2}$, $R^{10.3}$ and $R^{10.4}$ is not hydrogen.

In some embodiments, $R^{10.1}$ or $R^{10.3}$ is methyl. In some embodiments, $R^{10.2}$ or $R^{10.4}$ is methyl. In some embodiments, $R^{10.1}$ or $R^{10.3}$ is oxo. In some embodiments, $R^{10.2}$ or $R^{10.4}$ is oxo. In some embodiments, $R^{10.1}$ or $R^{10.3}$ is —C(O)OH. In some embodiments, $R^{10.2}$ or $R^{10.4}$ is —C(O)OH. In some embodiments, $R^{10.1}$ or $R^{10.3}$ is —$CH_2OH$. In some embodiments, $R^{10.2}$ or $R^{10.4}$ is —$CH_2OH$. For example, the compound of Formula (I-A) is:

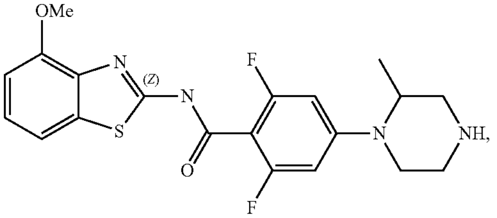

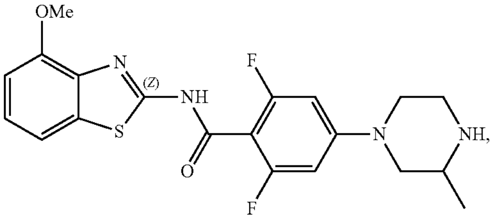

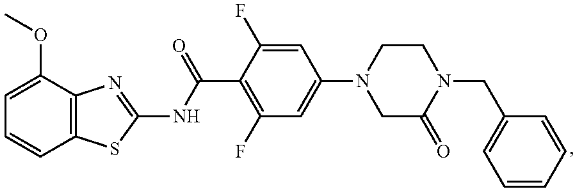

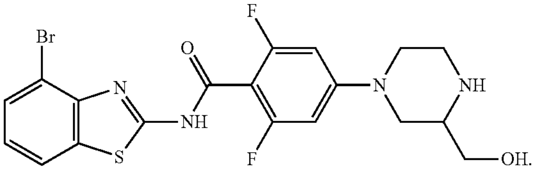

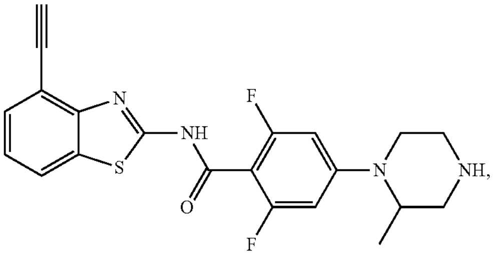

or

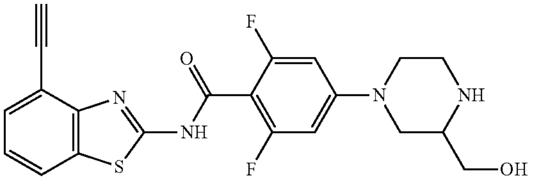

In some embodiments, $L^1$ is —C(O)— and $R^9$ is hydrogen. In some embodiments, the compound is:

(I-A-2)

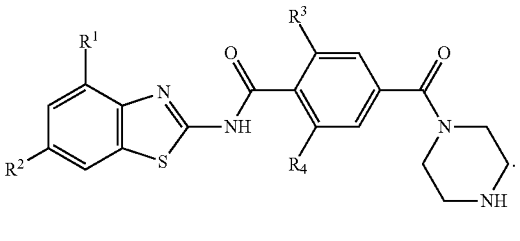

$R^1$, $R^2$, $R^3$, and $R^4$ are as described above. For example, the compound of Formula (I-A-2) is

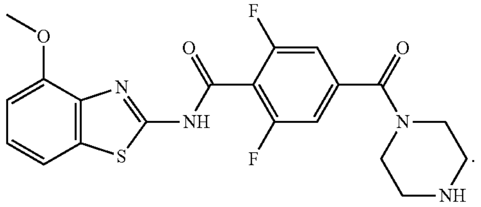 [SMILES: COc1cccc2sc(NC(=O)c3c(F)cc(C(=O)N4CCNCC4)cc3F)nc12]

In some embodiments, one or more of $R^{10.1}$, $R^{10.2}$, $R^{10.3}$, and $R^{10.4}$ are joined to each other or to atoms of the piperazinyl ring to form a substituted or unsubstituted heterocycloalkyl. For example, one or more of $R^{10.1}$, $R^{10.2}$, $R^{10.3}$, and $R^{10.4}$ are joined to each other or to atoms of the piperazinyl ring to form a substituted or unsubstituted 2,5-diazabicyclo[2.2.1]heptane, 3,6-diazabicyclo[3.1.1]heptane, 3,8-diazabicyclo[3.2.1]octane, 2,5-diazabicyclo[2.2.2]octane, 3,9-diazabicyclo[3.3.1]nonane, 2-thia-5-azabicyclo[2.2.1]heptane 2,2-dioxide, 2-azabicyclo[2.2.1]hept-5-ene, 3-oxa-8-azabicyclo[3.2.1]octane, 3-oxa-6-azabicyclo[3.1.1]heptane, 6-oxa-3-azabicyclo[3.1.1]heptane and 2-oxa-5-azabicyclo[2.2.1]heptane.

In some embodiments, $R^{10.1}$ or $R^{10.3}$ is joined to atoms of the piperazinyl ring to form 4 to 6 membered heterocycloalkyl including the nitrogen atom of the piperazinyl ring. In some embodiments, $R^{10.1}$ or $R^{10.3}$ is joined to atoms of the piperazinyl ring to form $R^5$ of

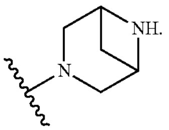 [SMILES: *N1CC2CC(C1)N2]

For example, the compound is

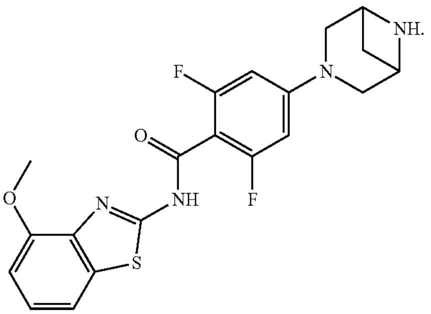 [SMILES: COc1cccc2sc(NC(=O)c3c(F)cc(N4CC5CC(C4)N5)cc3F)nc12]

In some embodiments, $R^5$ and $R^7$ are is hydrogen. In some embodiments, $R^{6B}$ and $R^{6C}$ together with atoms attached thereto are joined to form a substituted or unsubstituted piperazinyl. In some embodiments, $R^5$ and $R^7$ are is hydrogen; and $R^{6B}$ and $R^{6C}$ together with atoms attached thereto are joined to form a substituted or unsubstituted piperazinyl.

In some embodiments, $L^1$ is methylene or ethylene. In some embodiments, the compound has a structure of:

(I-A-3)

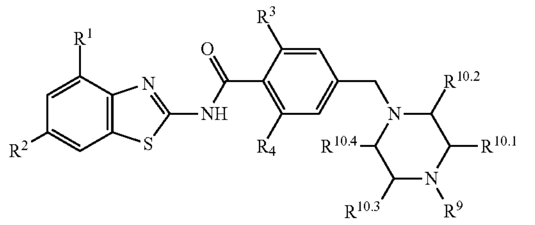

or (I-A-4)

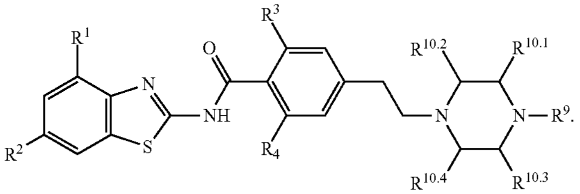

$R^1$, $R^2$, $R^3$, $R^4$, $R^9$, $R^{10.1}$, $R^{10.2}$, $R^{10.3}$, and $R^{10.4}$ are as described above.

In some embodiments, $R^{10.1}$, $R^{10.2}$, $R^{10.3}$, and $R^{10.4}$ are hydrogen. In some embodiments, $R^9$ is hydrogen, or unsubstituted $C_1$-$C_4$ alkyl. In some embodiments, $R^9$ is hydrogen. In some embodiments, $R^9$ is unsubstituted $C_1$-$C_4$ alkyl. In embodiments, $R^9$ is —C(O)$NR^{9B}R^{9C}$. For example, the compound of Formula (I-A-3) or (I-A-4) is

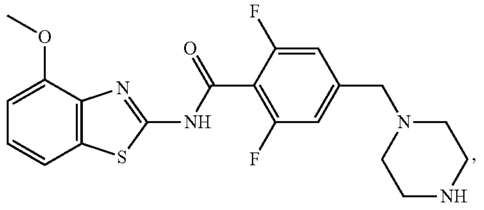

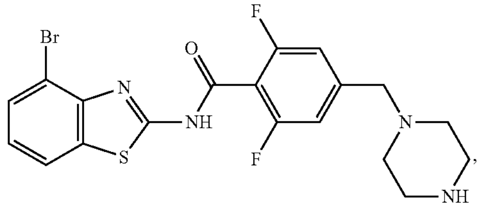

or

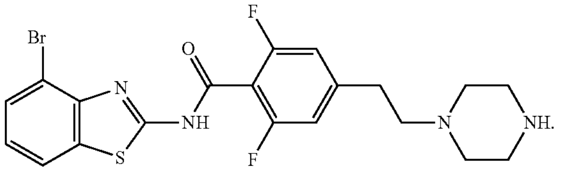

In some embodiments, the compound as a structure of:

(I-B)

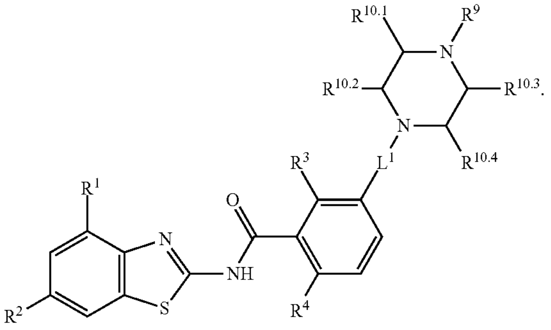

$R^1$, $R^2$, $R^3$, $R^4$, $L^1$, $R^9$, $R^{10.1}$, $R^{10.2}$, $R^{10.3}$, and $R^{10.4}$ are as described above.

In some embodiments, $R^9$ is hydrogen. In some embodiments, $R^9$, $R^{10.1}$, $R^{10.2}$, $R^{10.3}$ and $R^{10.4}$ are hydrogen. In some embodiments, the compound has the structure of:

(I-B-1)

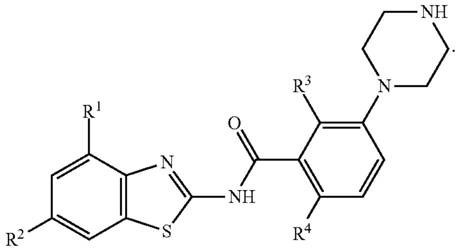

$R^1$, $R^2$, $R^3$, and $R^4$ are as described above. For example, the compound of Formula (I-B-1) is

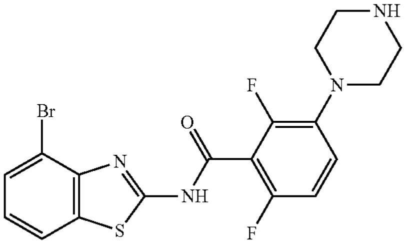

or

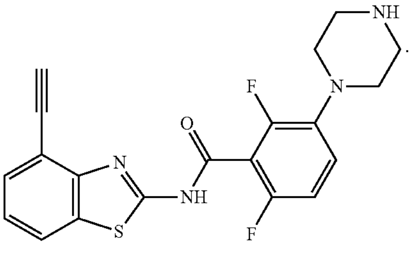

In some embodiments, in Formula (I-B), $R^9$ is methyl, ethyl, propyl, —C(O)$NH_2$,

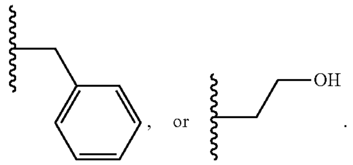

In some embodiments, $R^5$ and $R^6$ are is hydrogen. In some embodiments, $R^{7B}$ and $R^{7C}$ together with atoms attached thereto are joined to form a substituted or unsubstituted piperazinyl. In some embodiments, $R^5$ and $R^6$ are is hydrogen; and $R^{7B}$ and $R^{7C}$ together with atoms attached thereto are joined to form a substituted or unsubstituted piperazinyl.

In some embodiments, the compound has a structure of:

(I-B')

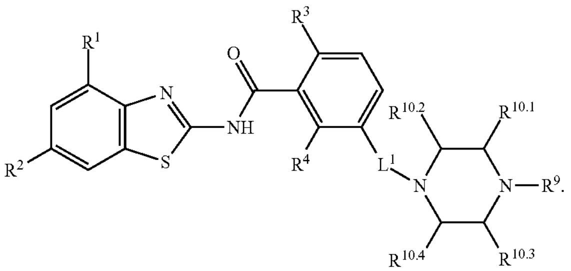

$R^1$, $R^2$, $R^3$, $R^4$, $L^1$, $R^9$, $R^{10.1}$, $R^{10.2}$, $R^{10.3}$, and $R^{10.4}$ are as described above.

In some embodiments, $R^6$ and $R^7$ are hydrogen, and $R^5$ is substituted or unsubstituted heterocycloalkyl (e.g., piperidyl, pyrrolidinyl, or morpholinyl), or substituted or unsubstituted heteroaryl (e.g., pyridyl, or pyrimidinyl). In some embodiments, $R^6$ and $R^7$ are hydrogen, $R^5$ is —$NR^{5B}R^{5C}$ and $R^{5B}$ and $R^{5C}$ together with atoms attached thereto are joined to form a substituted or unsubstituted 5 to 6 membered heterocycloalkyl, or substituted or unsubstituted heteroaryl.

In some embodiments, the compound has a structure of:

(I-C)

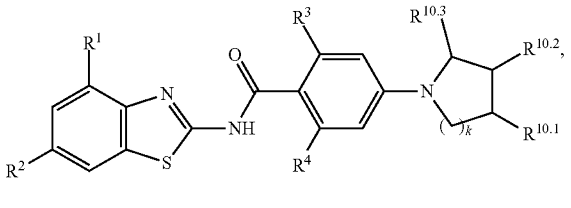

wherein:

k is 1 or 2;

Each $R^{10.1}$, $R^{10.2}$, and $R^{10.3}$ is independently hydrogen, —$OR^{10A}$, —C(O)$OR^{10A}$, —$NR^{10B}R^{10C}$, —$(CH_2)_m$OH, substituted or unsubstituted $C_1$-$C_6$ alkyl, substituted or unsubstituted 2 to 6 membered heteroalkyl, or substituted or unsubstituted $C_3$-$C_6$ cycloalkyl, or one or more of $R^{10.1}$, $R^{10.2}$, and $R^{10.3}$ are optionally joined to each other or to atoms of the heterocyclic ring to form a substituted or unsubstituted heterocycloalkyl;

m is an integer of 1 to 4; and

Each $R^{10A}$, $R^{10B}$ and $R^{10C}$ are independently hydrogen, or unsubstituted $C_1$-$C_6$ alkyl.

In the Formula (I-C), $R^1$, $R^2$, $R^3$, and $R^4$ are as described above.

In some embodiments, each $R^{10.1}$, $R^{10.2}$, and $R^{10.3}$ is independently hydrogen, —C(O)OH, —C(O)$OCH_3$, —$NH_2$, —OH, or —($CH_2$)OH. In some embodiments, $R^{10.1}$ is independently hydrogen, —C(O)OH, —C(O)$OCH_3$, —$NH_2$, —OH, or —($CH_2$)OH. In some embodiments, $R^{10.2}$ is independently hydrogen, —C(O)OH, —C(O)$OCH_3$, —$NH_2$, —OH, or —($CH_2$)OH. In some embodiments, $R^{10.3}$ is independently hydrogen, —C(O)OH, —C(O)$OCH_3$, —$NH_2$, —OH, or —($CH_2$)OH. In some embodiments, $R^{10.1}$ is hydrogen. In some embodiments, $R^{10.2}$ is hydrogen. In some embodiments, $R^{10.3}$ is hydrogen.

In some embodiments, $R^{10.1}$ is independently hydrogen, —C(O)OH, —C(O)$OCH_3$, —$NH_2$, —OH, or —($CH_2$)OH, and $R^{10.2}$ and $R^{10.3}$ are hydrogen. In some embodiments, $R^{10.2}$ is independently hydrogen, —C(O)OH, —C(O)$OCH_3$, —$NH_2$, —OH, or —($CH_2$)OH, and $R^{10.1}$ and $R^{10.3}$ are hydrogen. In some embodiments, $R^{10.3}$ is independently hydrogen, —C(O)OH, —C(O)$OCH_3$, —$NH_2$, —OH, or —($CH_2$)OH, and $R^{10.1}$ and $R^{10.3}$ are hydrogen.

In some embodiments, the compound has the structure of:

(I-C-1)

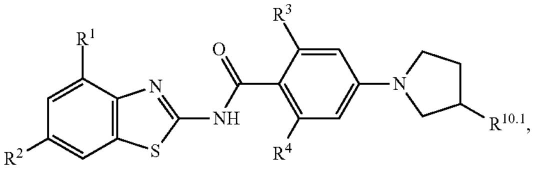

or (I-C-2)

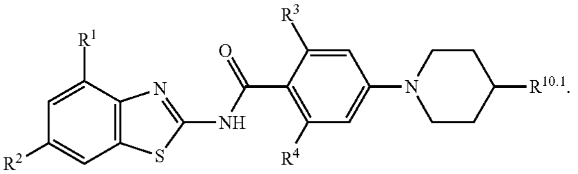

$R^1$, $R^2$, $R^3$, $R^4$, and $R^{10.1}$ are as described above.

In some embodiments, $R^1$ is —$OCH_3$. In some embodiments, $R^{10.1}$ is independently hydrogen, —C(O)OH, —C(O)$OCH_3$, —$NH_2$, —OH, or —($CH_2$)OH. For example, the compound of Formula (I-C-1) or (I-C-2) is

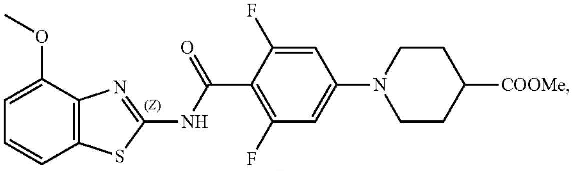

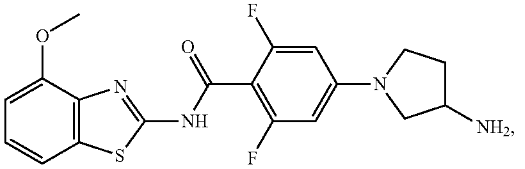

-continued

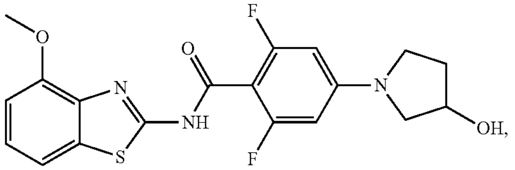

or

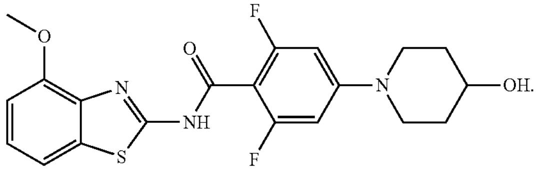

In some embodiments, $R^6$ and $R^7$ are hydrogen, and $R^5$ is substituted or unsubstituted morpholinyl. In some embodiments, $R^6$ and $R^7$ are hydrogen, $R^5$ is $-NR^{5B}R^{5C}$ and $R^{5B}$ and $R^{5C}$ together with atoms attached thereto are joined to form a substituted or unsubstituted morpholinyl.

In some embodiments, the compound has the structure of:

(I-D)

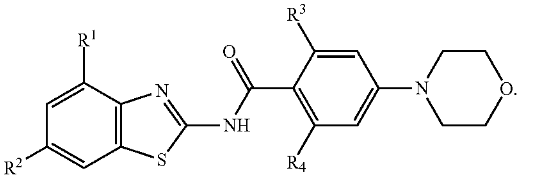

$R^1$, $R^2$, $R^3$, and $R^4$ are as described above.

In some embodiments, $R^9$ is hydrogen. For example, the compound is

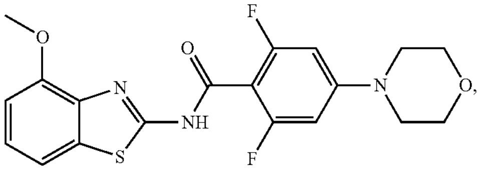

or

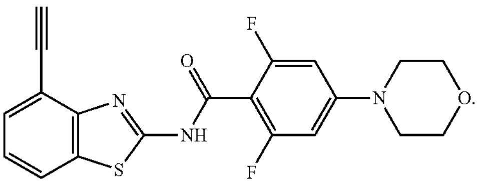

In some embodiments, $R^6$ and $R^7$ are hydrogen, and $R^5$ is substituted or unsubstituted morpholinyl. In some embodiments, $R^5$ is unsubstituted morpholinyl. In some embodiments, $R^6$ and $R^7$ are hydrogen, $R^5$ is $-NR^{5B}R^{5C}$ and $R^{5B}$ and $R^{5C}$ together with atoms attached thereto are joined to form a substituted or unsubstituted morpholinyl. In some embodiments, $R^{5B}$ and $R^{5C}$ together with atoms attached thereto are joined to form unsubstituted morpholinyl. For example, the compound is

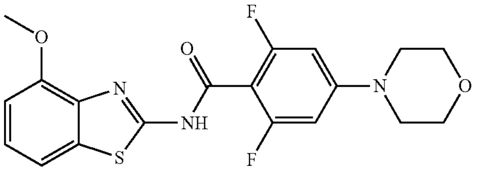

or

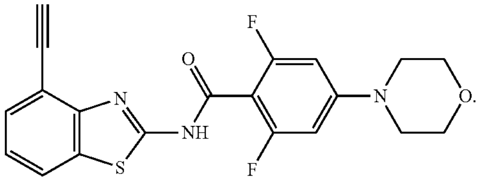

In some embodiments, $R^6$ and $R^7$ are hydrogen, and $R^5$ is substituted or unsubstituted aryl. In some embodiments, $R^5$ is substituted or unsubstituted phenyl. For example, the compound is

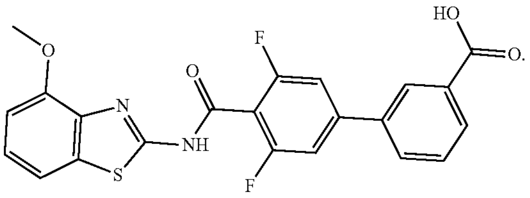 [SMILES: COc1cccc2sc(NC(=O)c3c(F)cc(-c4cccc(C(=O)O)c4)cc3F)nc12]

In some embodiments, $R^6$ and $R^7$ are hydrogen, and $R^5$ is $-O(CH_2)_mOH$, or $-NHR^{5C}$, $R^{5C}$ is $-(CH_2)_mOH$, $-(CH_2)_mNH_2$, $-(CH_2)_mNHCH_3$, and $-(CH_2)_mN(CH_3)_2$, and each m is independently an integer of 1 to 4. In some embodiments, m is 1 or 2. In some embodiments, $R^5$ is

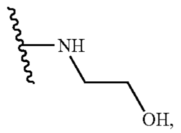

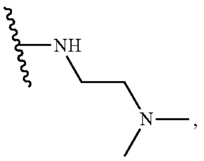

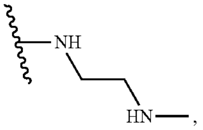

or

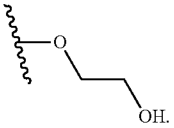

For example, the compound is

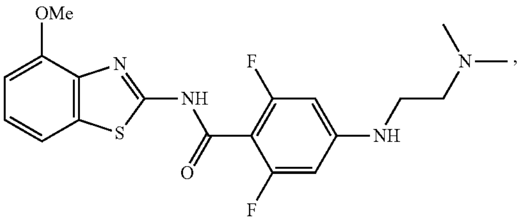

-continued

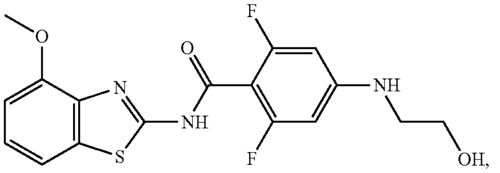

or

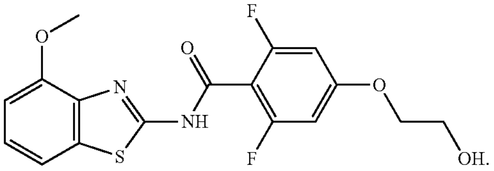

In some embodiments, $R^5$, $R^6$ and $R^7$ are hydrogen and $R^1$ is cyclopropyl, or —Br. For example, the compound is

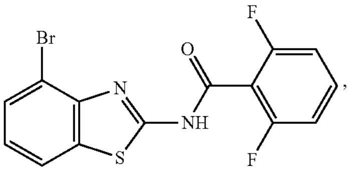

or

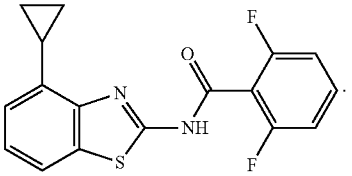

When $R^2$, $R^5$, $R^6$, and $R^7$ are hydrogen and $R^3$ and $R^4$ are —F, then $R^1$ is not —$OCH_3$. In some embodiments, when $R^5$, $R^6$, and $R^7$ are hydrogen and $R^3$ and $R^4$ are —F, then $R^1$ is not —$OCH_3$.

In some embodiments, the compound of Formula (I) or a subembodiment is

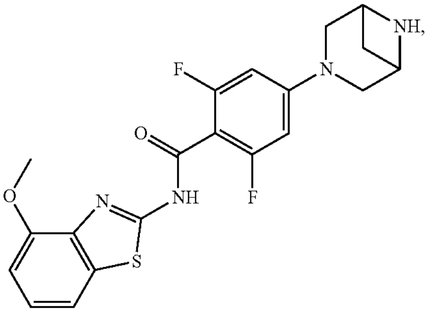

-continued

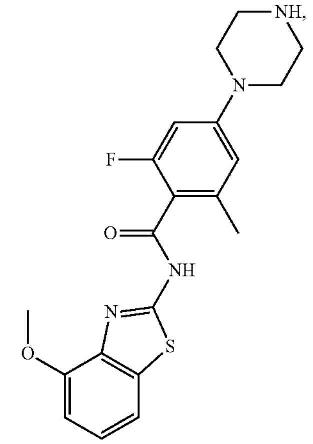

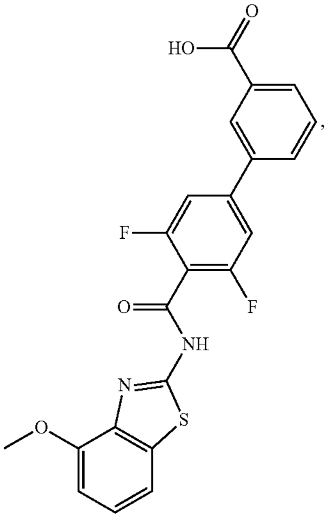

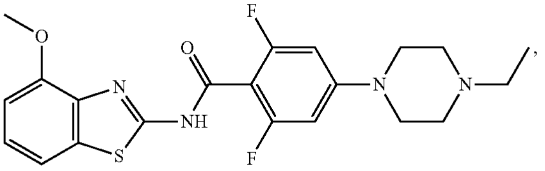

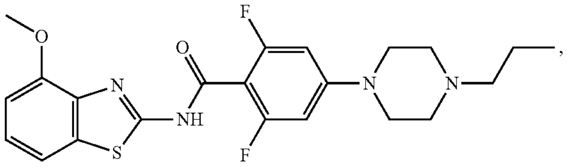

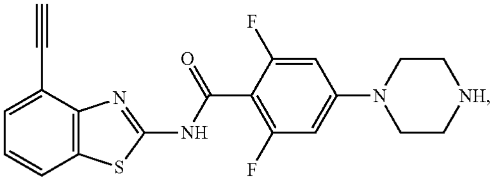

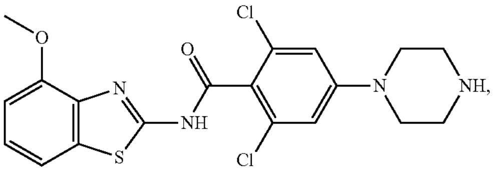

-continued
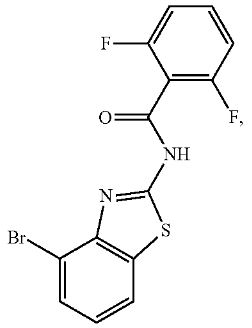
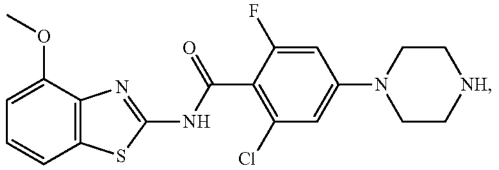
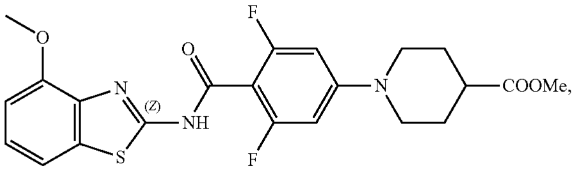
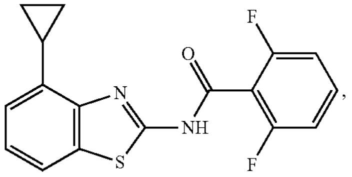
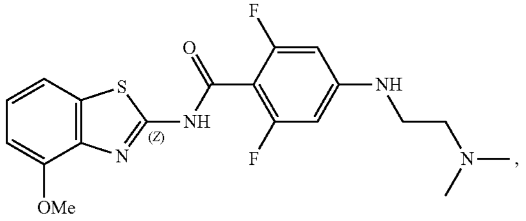
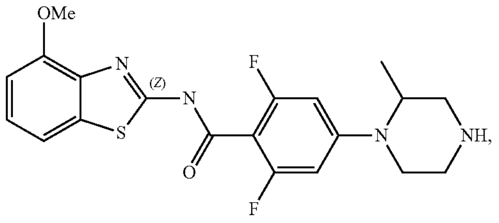
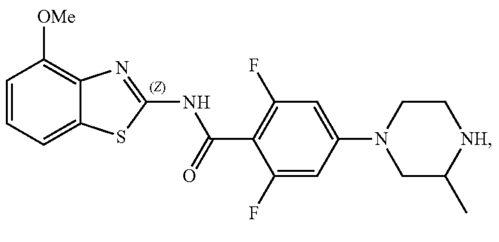
-continued
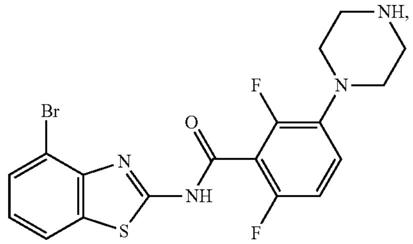
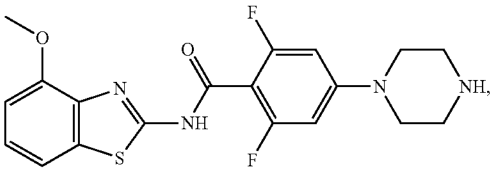
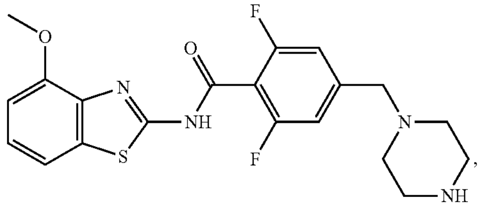
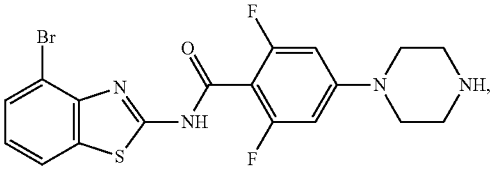
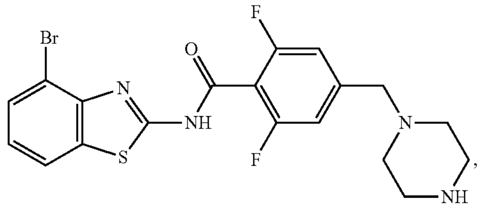
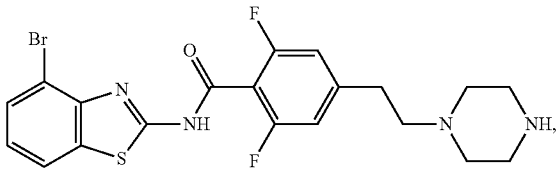
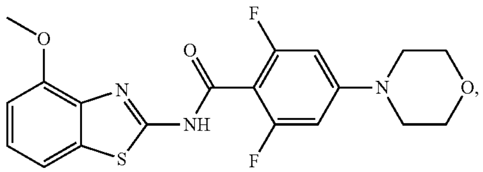
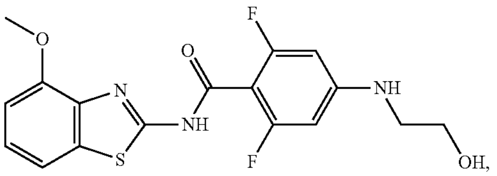
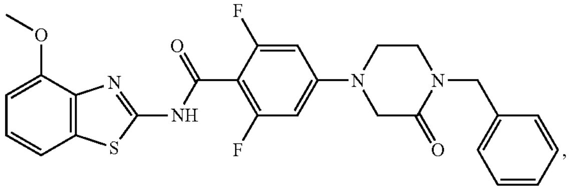

-continued
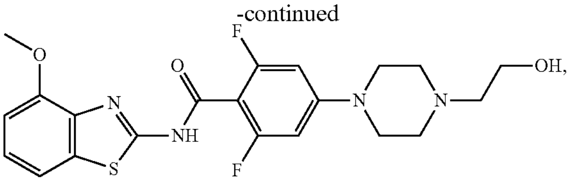
,
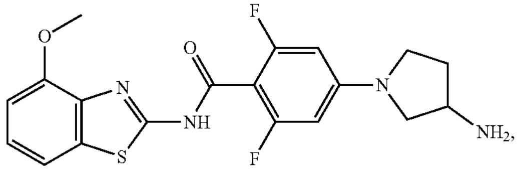
,
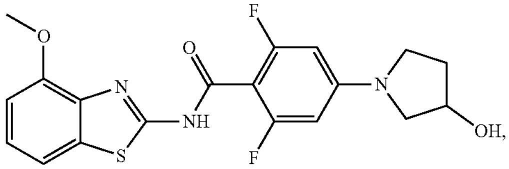
,
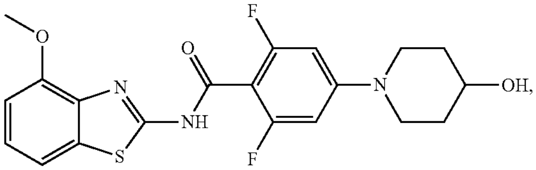
,
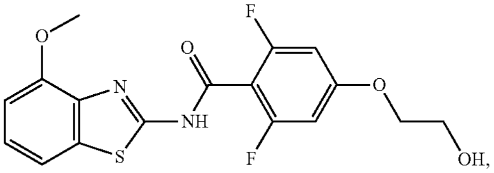
,
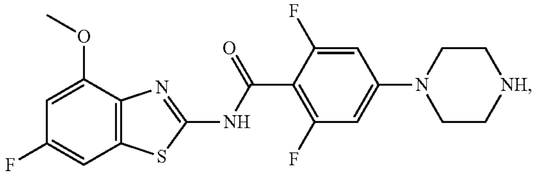
,
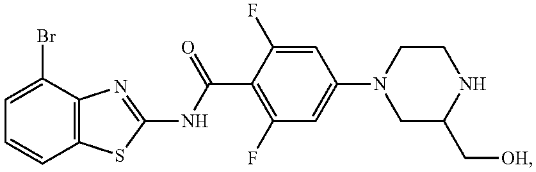
,
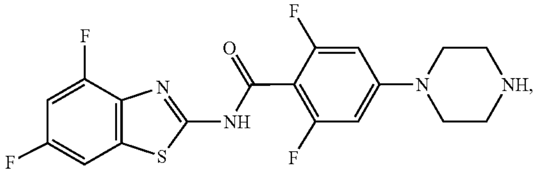
,
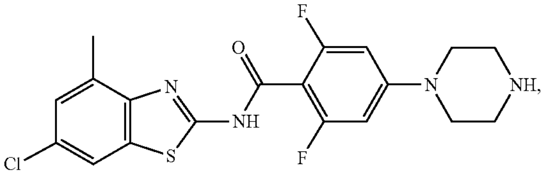
,
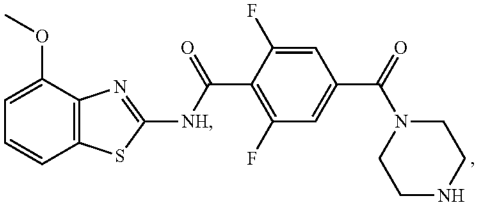
,
-continued
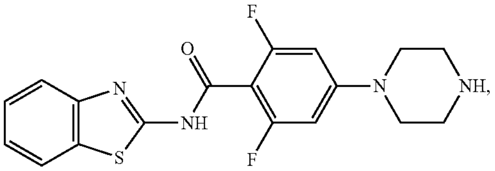
,
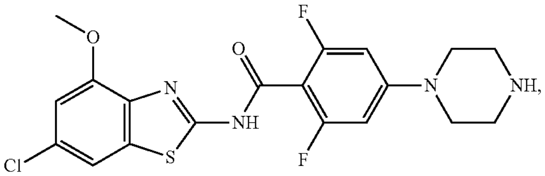
,
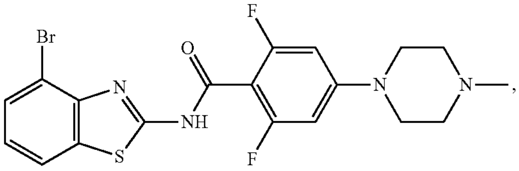
,
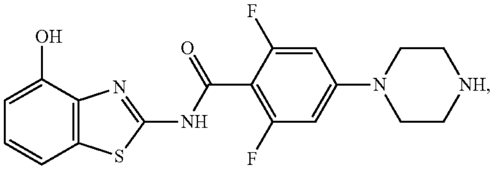
,
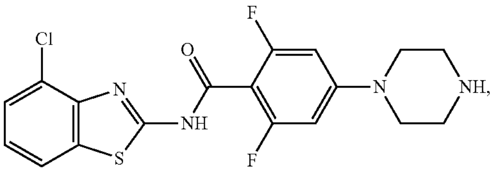
,
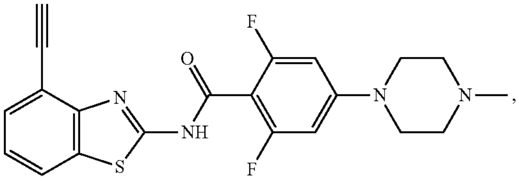
,
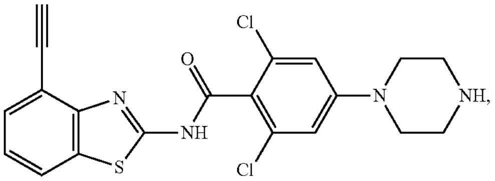
,
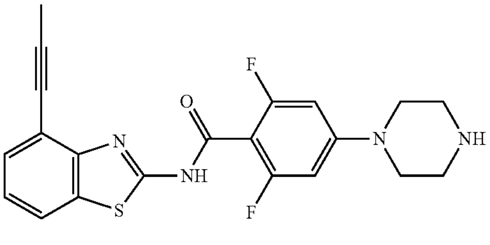
or -continued

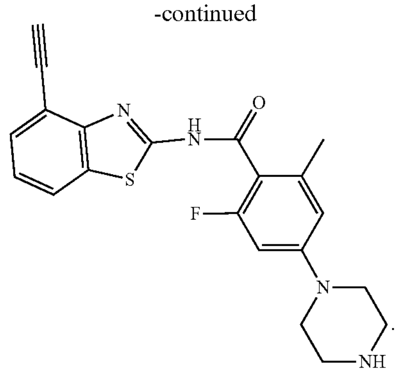

In some embodiments, the compound is

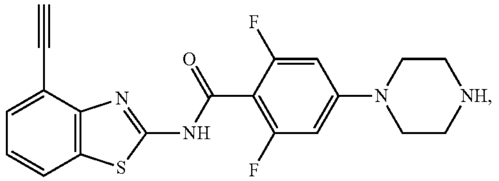

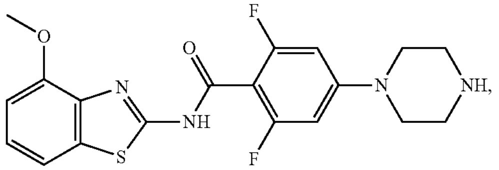

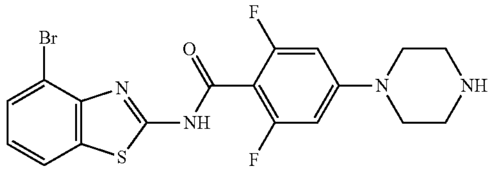

or

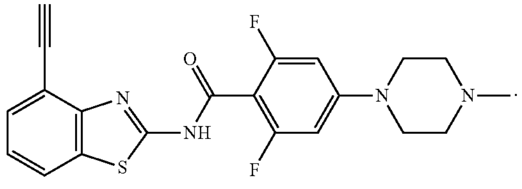

In an aspect, a compound has a structure of:

(II)

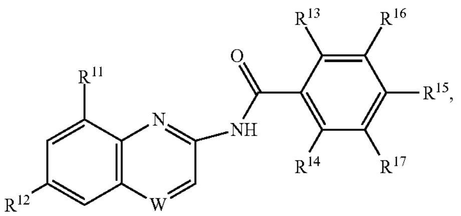

or a salt thereof, wherein:

W is —$CR^{18}$═ or —N═;

$R^{11}$ is hydrogen, halogen, —$CX'_3$, —$CHX'_2$, —$CH_2X'$, —$OCX'_3$, —$OCH_2X'$, —$OCHX'_2$, —$OR^{11A}$, substituted or unsubstituted $C_1$-$C_6$ alkyl, substituted or unsubstituted 2 to 6 membered heteroalkyl, substituted or unsubstituted $C_3$-$C_6$ cycloalkyl;

Each $R^{12}$, $R^{13}$, and $R^{14}$ is independently hydrogen, halogen, —$OR^{12A}$ or unsubstituted $C_1$-$C_6$ alkyl;

$R^{15}$ is hydrogen, —$NR^{15B}R^{15C}$, —$(CH_2)_{n15}NR^{15B}R^{15C}$, —C(O)$NR^{15B}R^{15C}$, —$O(CH_2)_{m15}OR^{15A}$, —$OR^{15A}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 5 to 6 membered heterocycloalkyl, substituted or unsubstituted $C_6$-$C_{12}$ aryl, or substituted or unsubstituted 5 to 6 membered heteroaryl;

$R^{16}$ is hydrogen, —$NR^{16B}R^{16C}$, —$(CH_2)_{n16}NR^{16B}R^{16C}$, —C(O)$NR^{16B}R^{16C}$, —$O(CH_2)_{m16}OR^{16A}$, —$OR^{16A}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 5 to 6 membered heterocycloalkyl, substituted or unsubstituted $C_6$-$C_{12}$ aryl, or substituted or unsubstituted 5 to 6 membered heteroaryl;

$R^{17}$ is hydrogen, —$NR^{17B}R^{17C}$, —$(CH_2)_{n17}NR^{17B}R^{17C}$, —C(O)$NR^{17B}R^{17C}$, —$O(CH_2)_{m17}OR^{17A}$, —$OR^{17A}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 5 to 6 membered heterocycloalkyl, substituted or unsubstituted $C_6$-$C_{12}$ aryl, or substituted or unsubstituted 5 to 6 membered heteroaryl;

$R^{18}$ is hydrogen, or unsubstituted $C_1$-$C_6$ alkyl;

X' is independently —F, —Cl, —Br or —I;

Each n15, n16, and n17 is independently an integer of 1 to 4;

Each m15, m16, and m17 is independently an integer of 1 to 4;

Each $R^{11A}$, $R^{12A}$, $R^{15A}$, $R^{15B}$, $R^{15C}$, $R^{16A}$, $R^{16B}$, $R^{16C}$, $R^{17A}$, $R^{17B}$, and $R^{17C}$ are independently hydrogen, substituted or unsubstituted $C_1$-$C_4$ alkyl, or substituted or unsubstituted 2 to 4 membered heteroalkyl, or $R^{15B}$ and $R^{15C}$ together with atoms attached thereto are optionally joined to form a substituted or unsubstituted 5 to 6 membered heterocycloalkyl. or substituted or unsubstituted heteroaryl; $R^{16B}$ and $R^{16C}$ together with atoms attached thereto are optionally joined to form a substituted or unsubstituted 5 to 6 membered heterocycloalkyl, or substituted or unsubstituted heteroaryl; or $R^{17B}$ and $R^{17C}$ together with atoms attached thereto are optionally joined to form a substituted or unsubstituted 5 to 6 membered heterocycloalkyl, or substituted or unsubstituted heteroaryl.

In some embodiments, W is —N═. In some embodiments, W is —$CR^{18}$═. In some embodiments, $R^{18}$ is hydrogen, or methyl.

In some embodiments, $R^{11}$ is hydrogen, halogen, unsubstituted $C_2$-$C_4$ alkynyl, unsubstituted $C_1$-$C_4$ alkyl, unsubstituted $C_3$-$C_6$ alkyl, —$OCX'_3$, —$OCH_2X'$, —$OCHX'_2$, or —$OR^{11A}$; and $R^{11A}$ is hydrogen or unsubstituted $C_1$-$C_4$ alkyl. In some embodiments, $R^{11}$ is hydrogen. In some embodiments, $R^{11}$ is —$OCH_3$. In some embodiments, In some embodiments, $R^{11}$ is —Br.

In some embodiments, $R^{12}$ is hydrogen, halogen, or —$OR^{12A}$. In some embodiments, $R^{12}$ is hydrogen. In some embodiments, $R^{12}$ is —F, —Cl, or Br. In some embodiments, $R^{12}$ is —$OR^{12A}$ and $R^{12A}$ is hydrogen or unsubstituted $C_1$-$C_4$ alkyl. In some embodiments, $R^{12A}$ is methyl. In some embodiments, $R^{12}$ is —$OCH_3$.

In some embodiments, each $R^{13}$ and $R^{14}$ is independently hydrogen, halogen, or unsubstituted $C_1$-$C_4$ alkyl. In some embodiments, $R^{13}$ is hydrogen, halogen, or unsubstituted $C_1$-$C_4$ alkyl. In some embodiments, $R^{14}$ is hydrogen, halogen, or unsubstituted $C_1$-$C_4$ alkyl. In some embodiments, each $R^{13}$ and $R^{14}$ is independently hydrogen, —F, —Cl, or methyl. In some embodiments, $R^{14}$ is hydrogen, —F, —Cl, or methyl. In some embodiments, $R^{14}$ is hydrogen, —F, —Cl, or methyl. In some embodiments, $R^{13}$ and $R^{14}$ are —F.

In some embodiments, $R^{16}$ and $R^{17}$ are hydrogen. In some embodiments, $R^{15B}$ and Rise together with atoms attached thereto are joined to form a substituted or unsubstituted piperazinyl. In some embodiments, $R^{16}$ and $R^{17}$ are hydrogen; and $R^{15B}$ and $R^{15C}$ together with atoms attached thereto are joined to form a substituted or unsubstituted piperazinyl.

In some embodiments, the compound has a structure of:

(II-A)

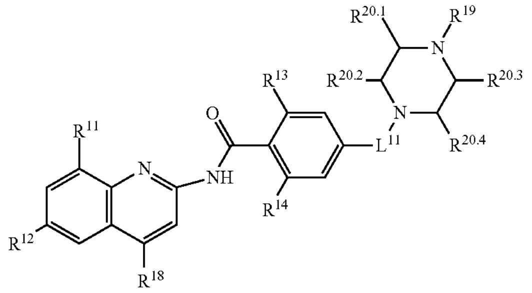

or (II-B)

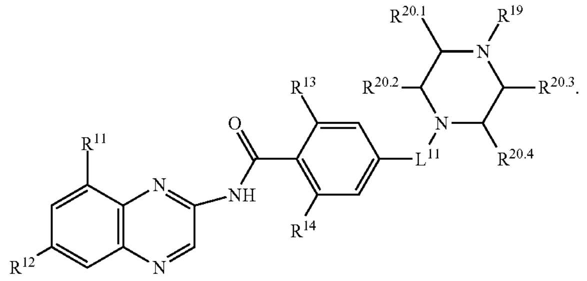

wherein:

$L^{11}$ is a bond, or $—(CH_2)_{n15}$;

$R^{19}$ is hydrogen, substituted or unsubstituted $C_1$-$C_6$ alkyl, or substituted or unsubstituted 2 to 6 membered heteroalkyl;

Each $R^{20.1}$, $R^{20.2}$, $R^{20.3}$ and $R^{20.4}$ is independently hydrogen, $—OR^{20A}$, $—C(O)OR^{20A}$, $—NR^{20B}R^{20C}$, $—(CH_2)_{m'}OH$, substituted or unsubstituted $C_1$-$C_6$ alkyl, substituted or unsubstituted 2 to 6 membered heteroalkyl, or substituted or unsubstituted $C_3$-$C_6$ cycloalkyl, or one or more of $R^{20.1}$, $R^{20.2}$, $R^{20.3}$, and $R^{20.4}$ are optionally joined to each other or to atoms of the piperazinyl ring to form a substituted or unsubstituted heterocycloalkyl;

q is an integer of 0 to 8.

Each m' is independently an integer of 1 to 4; and

Each $R^{19A}$, $R^{20B}$ and $R^{20C}$ are independently hydrogen, or substituted or unsubstituted $C_1$-$C_6$ alkyl.

In Formula (II-A) or (II-B), $R^{11}$, $R^{12}$, $R^{13}$, $R^{14}$, and $R^{18}$ are as described above.

In some embodiments, $R^{15}$ and $R^{17}$ are hydrogen. In some embodiments, $R^{16B}$ and $R^{16C}$ together with atoms attached thereto are joined to form a substituted or unsubstituted piperazinyl. In some embodiments, $R^{15}$ and $R^{17}$ are hydrogen; and $R^{16B}$ and $R^{16C}$ together with atoms attached thereto are joined to form a substituted or unsubstituted piperazinyl.

In some embodiments, the compound has a structure of:

(II-C)

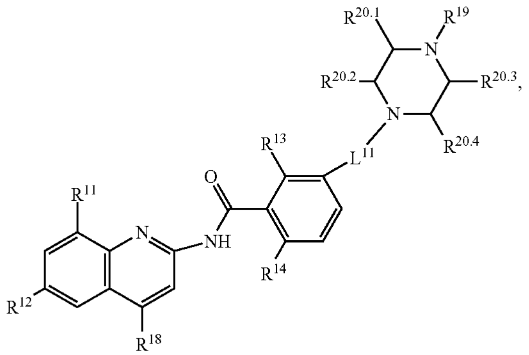

or (II-D)

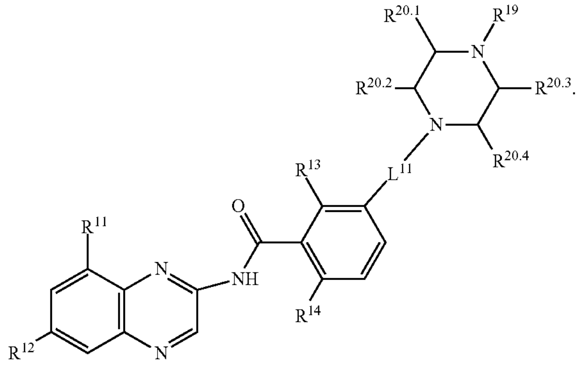

$R^{11}$, $R^{12}$, $R^{13}$, $R^{14}$, $L^{11}$, $R^{18}$, $R^{19}$, $R^{20.1}$, $R^{20.2}$, $R^{20.3}$, and $R^{20.4}$ are as described above.

In some embodiments, $R^{15}$ and $R^{16}$ are hydrogen. In some embodiments, $R^{17B}$ and $R^{17C}$ together with atoms attached thereto are joined to form a substituted or unsubstituted piperazinyl. In some embodiments, $R^{15}$ and $R^{16}$ are hydrogen; and $R^{17B}$ and $R^{17C}$ together with atoms attached thereto are joined to form a substituted or unsubstituted piperazinyl.

In some embodiments, the compound has a structure of:

(II-C')

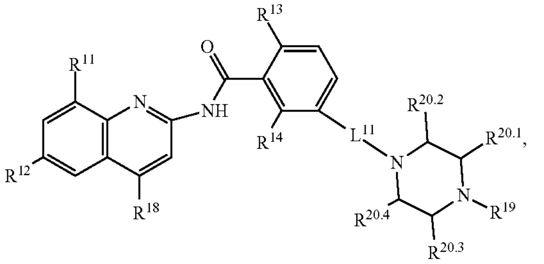

or

-continued (II-D')

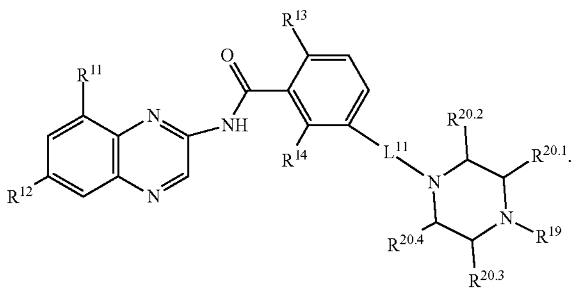

$R^{11}$, $R^{12}$, $R^{13}$, $R^{14}$, $L^{11}$, $R^{18}$, $R^{19}$, $R^{20.1}$, $R^{20.2}$, $R^{20.3}$, and $R^{20.4}$ are as described above.

In some embodiments, $L^{11}$ is a bond. In some embodiments, the compound has a structure of:

(II-A-1)

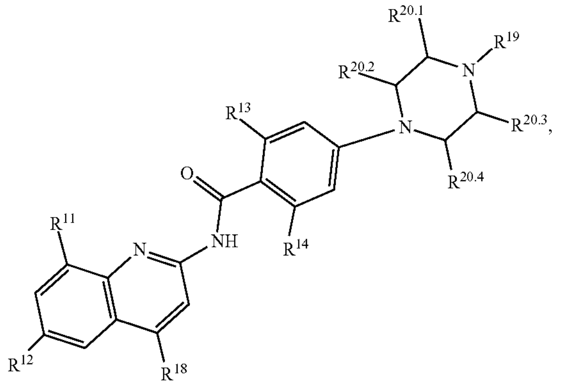

(II-B-1)

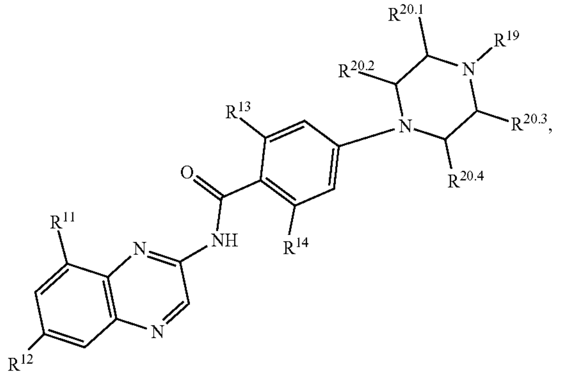

-continued (II-C-1)

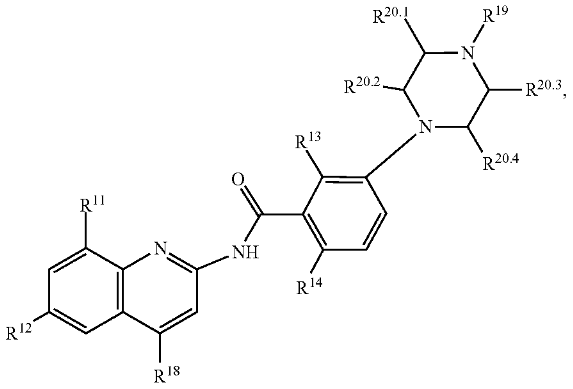

(II-D-1)

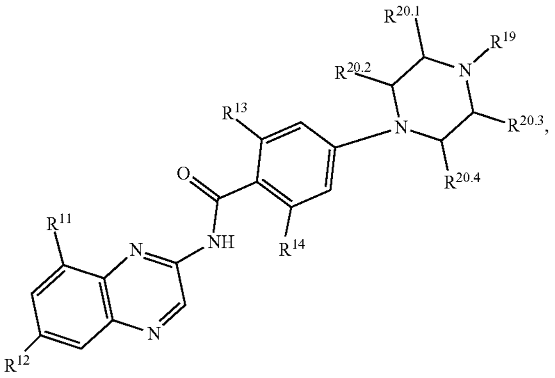

(II-C'-1)

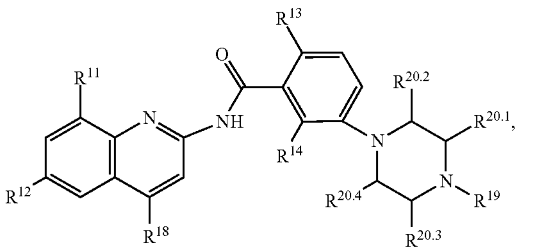

or (II-D'-1)

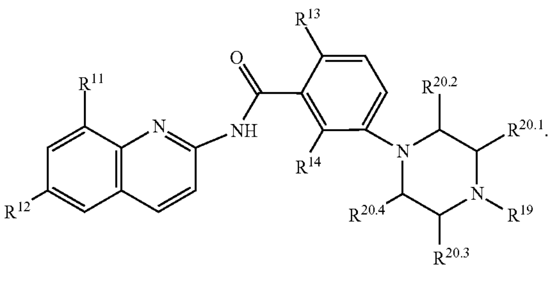

$R^{11}$, $R^{12}$, $R^{13}$, $R^{14}$, $R^{18}$, $R^{19}$, $R^{20.1}$, $R^{20.2}$, $R^{20.3}$, and $R^{20.4}$ are as described above.

In some embodiments, $R^{19}$ is hydrogen, or unsubstituted $C_1$-$C_4$ alkyl. In some embodiments, $R^{19}$ is hydrogen. In some embodiments, $R^{19}$ is methyl, or ethyl. In some embodiments, $R^{19}$ is methyl.

In some embodiments, $R^{11}$ is $—OCH^3$. In some embodiments, $R^{12}$ is hydrogen, —F or $—OCH_3$. In some embodiments, $R^{13}$ and $R^{14}$ are —F. In some embodiments, $R^{20.1}$, $R^{20.2}$, $R^{20.3}$, and $R^{20.4}$ are hydrogen. In some embodiments, $R^{19}$ is hydrogen or methyl. For example, the compound of Formula (II-A-1) is
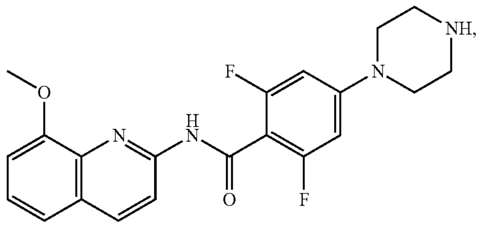
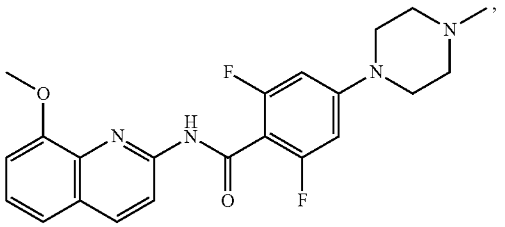
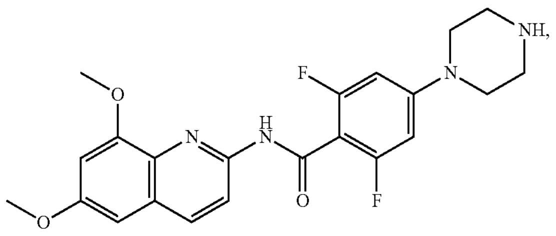
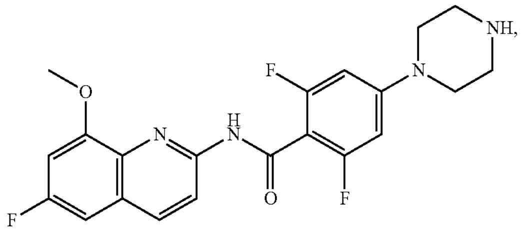
or
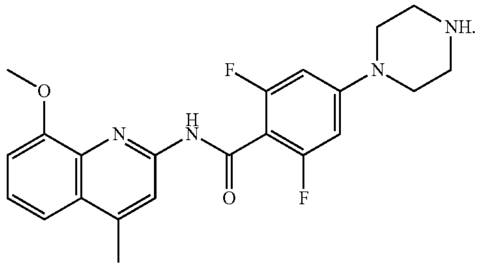
The compound of Formula (II-B-1) is
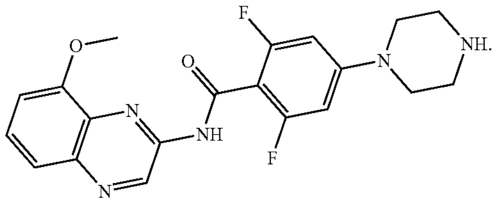 [SMILES: COc1cccc2ncc(NC(=O)c3c(F)cc(N4CCNCC4)cc3F)nc12]
The compound of Formula (II-C-1) is
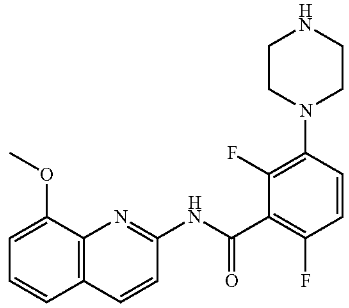 [SMILES: COc1cccc2ccc(NC(=O)c3c(F)ccc(N4CCNCC4)c3F)nc12]
In some embodiments, $L^{11}$ is methylene. In some embodiments, the compound has a structure of:
(II-A-2)
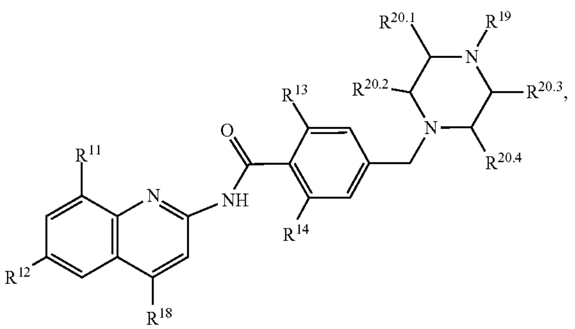
(II-B-2)
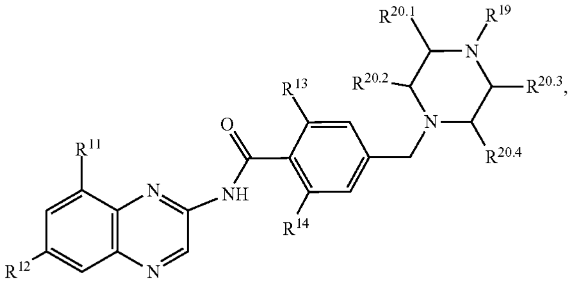
(II-C-2)
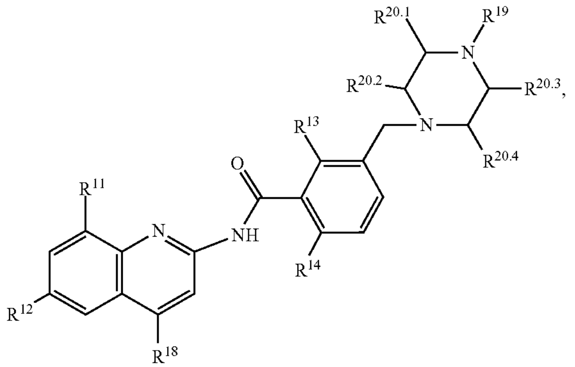

-continued (II-D-2)

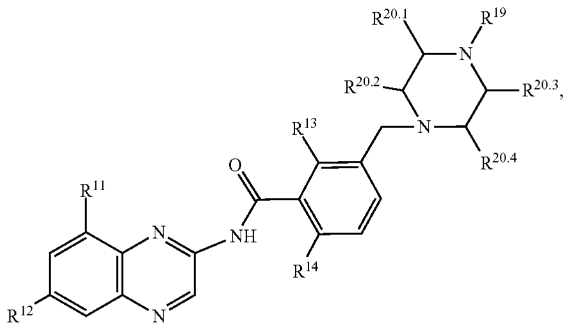

(II-C'-2)

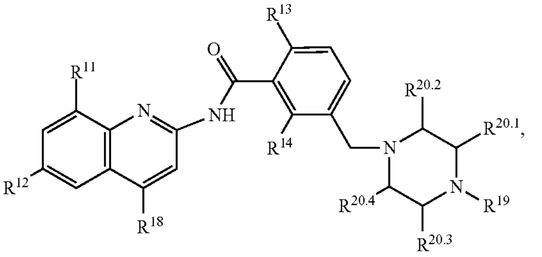

or (II-D'-2)

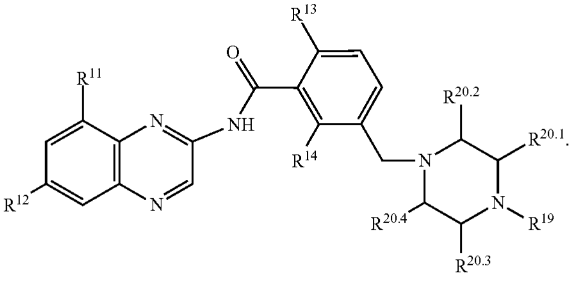

$R^{11}$, $R^{12}$, $R^{13}$, $R^{14}$, $R^{18}$, $R^{19}$, $R^{20.1}$, $R^{20.2}$, $R^{20.3}$, and $R^{20.4}$ are as described above.

In some embodiments, $R^{11}$ is —$OCH^3$. In some embodiments, $R^{12}$ is hydrogen. In some embodiments, $R^{13}$ and $R^{14}$ are —F. In some embodiments, $R^{20.1}$, $R^{20.2}$, $R^{20.3}$, and $R^{20.4}$ are hydrogen. In some embodiments, $R^{18}$ and $R^{19}$ are hydrogen. For example, the compound of Formula (II-C-2) is

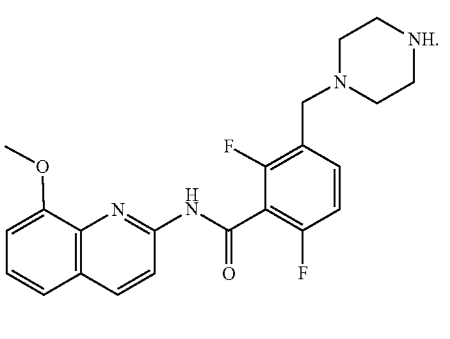 [SMILES: COc1cccc2ccc(NC(=O)c3c(F)ccc(CN4CCNCC4)c3F)nc12]

In some embodiments, $R^{20.1}$, $R^{20.2}$, $R^{20.3}$, and $R^{20.4}$ are hydrogen.

In some embodiments, $R^{16}$ and $R^{17}$ are hydrogen, and $R^{15}$ is substituted or unsubstituted heterocycloalkyl (e.g., piperidyl, pyrrolidinyl, or morpholinyl), or substituted or unsubstituted heteroaryl (e.g., pyridyl, or pyrimidinyl). In some embodiments, $R^{16}$ and $R^{17}$ are hydrogen, $R^{15}$ is —$NR^{15B}R^{15C}$ and $R^{15B}$ and $R^{15C}$ together with atoms attached thereto are joined to form a substituted or unsubstituted 5 to 6 membered heterocycloalkyl, or substituted or unsubstituted heteroaryl.

In some embodiments, the compound has structure of:

(II-E)

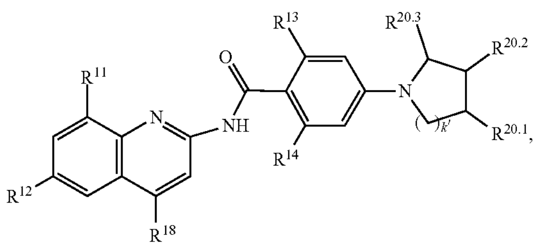

or (II-F)

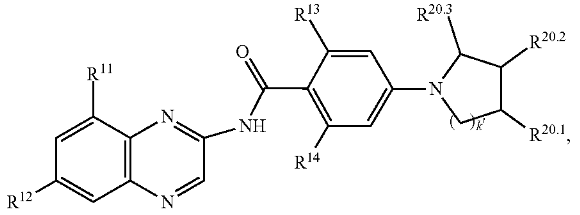

wherein:

k' is 1 or 2;

Each $R^{20.1}$, $R^{20.2}$, and $R^{20.3}$ is independently hydrogen, oxo, —$OR^{20A}$, —$C(O)OR^{20A}$, —$NR^{20B}R^{20C}$, —$(CH_2)_{m'}OH$, substituted or unsubstituted $C_1$-$C_6$ alkyl, substituted or unsubstituted 2 to 6 membered heteroalkyl, or substituted or unsubstituted $C_3$-$C_6$ cycloalkyl, or one or more of $R^{20.1}$, $R^{20.2}$, and $R^{20.3}$ are optionally joined to each other or to atoms of the heterocyclic ring to form a substituted or unsubstituted heterocycloalkyl;

Each m' is independently an integer of 1 to 4; and

Each $R^{20A}$, $R^{20B}$ and $R^{20C}$ is independently hydrogen, or unsubstituted $C_1$-$C_6$ alkyl.

In Formula (II-E) or (II-F), $R^{11}$, $R^{12}$, $R^{13}$, $R^{14}$, $R^{18}$, $R^{20.1}$, $R^{20.2}$, and $R^{20.3}$ are as described above.

In some embodiments, $R^{20.1}$, $R^{20.2}$, and $R^{20.3}$ is independently hydrogen, —C(O)OH, —$C(O)OCH_3$, —$NH_2$, —OH, or —$(CH_2)OH$. In some embodiments, $R^{20.1}$ is independently hydrogen, —C(O)OH, —$C(O)OCH_3$, —$NH_2$, —OH, or —$(CH_2)OH$. In some embodiments, $R^{20.2}$ is independently hydrogen, —C(O)OH, —$C(O)OCH_3$, —$NH_2$, —OH, or —$(CH_2)OH$. In some embodiments, $R^{20.3}$ is independently hydrogen, —C(O)OH, —$C(O)OCH_3$, —$NH_2$, —OH, or —$(CH_2)OH$. In some embodiments, $R^{20.1}$ is independently hydrogen, —C(O)OH, —$C(O)OCH_3$, —$NH_2$, —OH, or —$(CH_2)OH$, and $R^{20.2}$ and $R^{20.3}$ are hydrogen. In some embodiments, $R^{20.2}$ is independently hydrogen, —C(O)OH, —$C(O)OCH_3$, —$NH_2$, —OH, or —$(CH_2)OH$, and $R^{20.1}$ and $R^{20.3}$ are hydrogen. In some embodiments, $R^{20.3}$ is independently hydrogen, —C(O)OH, —$C(O)OCH_3$, —$NH_2$, —OH, or —$(CH_2)OH$, and $R^{20.1}$ and $R^{20.2}$ are hydrogen.

In some embodiments, $R^{20.1}$ is independently hydrogen, —C(O)OH, —$C(O)OCH_3$, —$NH_2$, —OH, or —$(CH_2)OH$, and $R^{20.2}$ and $R^{20.3}$ are hydrogen. In some embodiments, $R^{20.2}$ is independently hydrogen, —C(O)OH, —$C(O)OCH_3$, —$NH_2$, —OH, or —$(CH_2)OH$, and $R^{20.2}$ and $R^{20.3}$ are hydrogen.

In some embodiments, $R^{20.1}$ is independently hydrogen, —C(O)OH, —C(O)OCH$_3$, —NH$_2$, —OH, or —(CH$_2$)OH, and $R^{20.2}$ and $R^{20.3}$ are hydrogen.

In some embodiments, the compound has structure of:

(II-E-1)

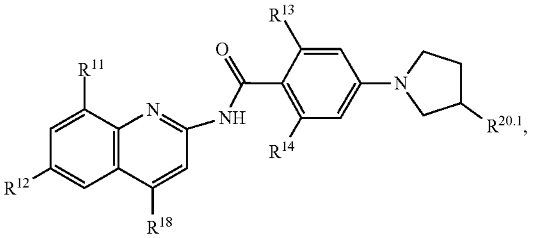

or (II-F-1)

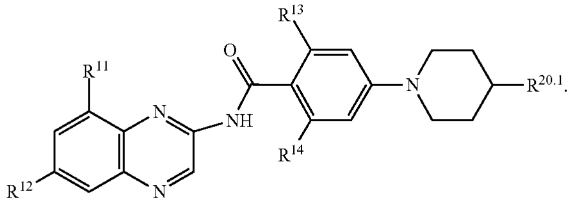

$R^{11}$, $R^{12}$, $R^{12}$, $R^{14}$, $R^{18}$, and $R^{20.1}$ are as described above.

In some embodiment, $R^1$ is —OCH$_3$ and $R^1$ is hydrogen. In some embodiments, $R^{20.1}$ is independently hydrogen, or —OH. For example, the compound of Formula (II-F-1) is

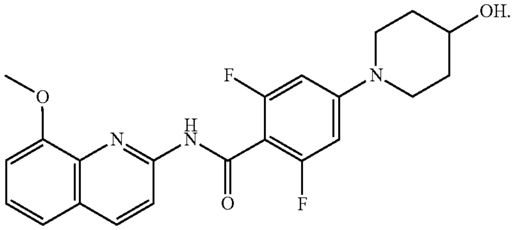 [SMILES: COc1cccc2ccc(NC(=O)c3c(F)cc(N4CCC(O)CC4)cc3F)nc12]

In some embodiments, the compound of Formula (II) or a subembodiment is:

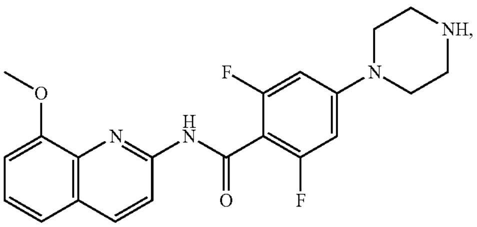

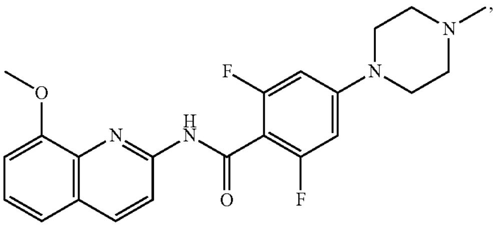

-continued

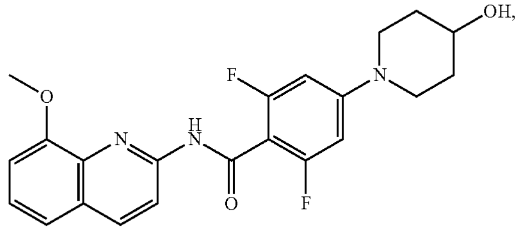

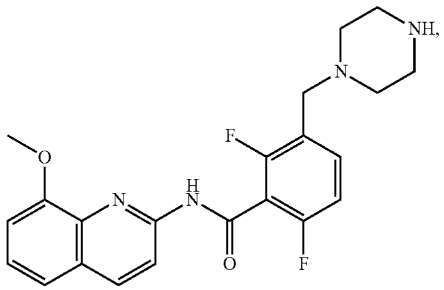

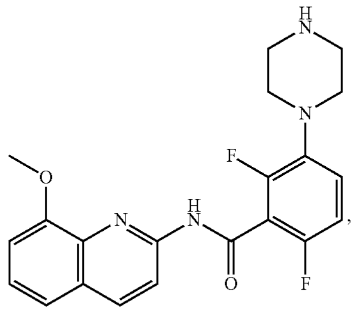

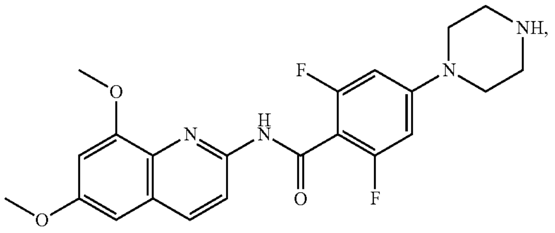

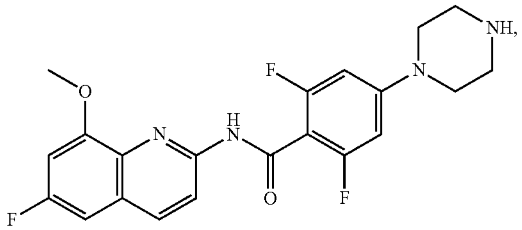

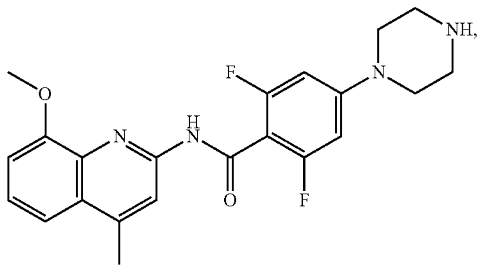

or

-continued

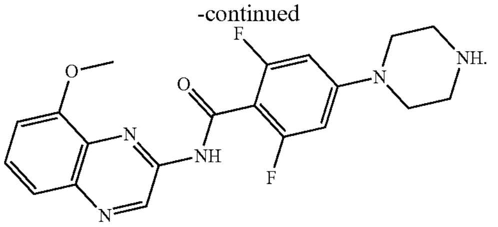

In some embodiments, the compound is selected from the examples provided herein.

Preparation of Compounds of Formula I and Exemplary Compounds

Analytical Details

NMR: Measurements were performed on a Bruker Ultrashield™ 400 (400 MHz) spectrometer using or not tetramethylsilane (TMS) as an internal standard. Chemical shifts (δ) are reported ppm downfield from TMS, spectra splitting pattern are designated as single (s), doublet (d), triplet (t), quartet (q), multiplet, unresolved or overlapping signals (m), broad signal (br). Deuterated solvent are given in parentheses and have a chemical shifts of dimethyl sulfoxide (δ 2.50 ppm), chloroform (δ 7.26 ppm), methanol (δ 3.31 ppm), or other solvent as indicated in NMR spectral data.

LC-MS: System: Shimadzu20A-2010MS
Detection: SPD-M20A
Column: MERCK, RP-18e 25-2 mm;
Wavelength: UV 220 nm, 254 nm;
Column temperature: 50° C.; MS ionization: ESI
Mobile Phase: 1.5 mL/4 LTFA in water (solvent A) and 0.75 mL/4 LTFA in acetonitrile (solvent B), using the elution gradient 5%-95% (solvent B) over 0.7 minutes and holding at 95% for 0.4 minutes at a flow rate of 1.5 mL/min;

Flash Column Chromatography System
System: CombiFlash Rf+
Column: Santai Technologies, Inc, SEPAFLASH®
Samples were typically adsorbed on isolute
Preparation on HPLC system
System: TRILUTION LC 4.0
Detection: Gilson 159 UV-VIS
Condition 1: Column: Phenomenex Gemini-NX 80*40 mm*3 um
Eluent A: water (0.05% $NH_3H_2O$+10 mM $NH_4HCO_3$)
Eluent B: $CH_3CN$
Begin B: 20-45%, End B: 80-20%, Gradient Time (min): 8
Condition 2: Column: Xtimate C18 10μ 250 mm*50 mm;
Eluent A: water (0.04% $NH_3H_2O$+10 mM $NH_4HCO_3$).
Eluent B: $CH_3CN$ 50%-80%; Gradient Time (min): 8

All starting materials, building blocks, reagents, acids, bases, dehydrating agents, solvents, and catalysts utilized to synthesis the compounds of the present disclosure are either commercially available or can be produced by organic synthesis methods known to one of ordinary skill in the art.

Below is the abbreviation table for chemistry:

| | |
|---|---|
| Ac | Acetyl |
| ACN | Acetonitrile |
| Cbz | Benzoxycarbonyl |
| CDI | N,N-Carbonyldiimidazole |
| Com. | Compound |
| DCM | Dichloromethane |
| DIEA | N,N-Diisopropylethylamine |
| DMAP | 4-Dimethylaminopyridine |
| DMF | N,N-Dimethylformamide |
| DMP | Dess-Martin Periodinane |
| DMSO | Dimethyl sulfoxide |
| EA | Ethyl Acetate |
| EDCI | 1-Ethyl-3-(3-dimethylaminopropyl)carbodiimide |
| ESI | Electron Spray Ionization |
| Et | Ethyl |
| HATU | 2-(7-Azabenzotriazol-1-yl)-N,N,N',N'-tetramethyluronium hexafluorophosphate |
| HBTU | O-Benzotriazole-N,N,N',N'-tetramethyl-uronium-hexafluorophosphate |
| HOBt | 1-Hydroxybenzotriazole |
| HPLC | High Performance Liquid Chromatography |
| Int | Intermediate |
| LCMS | Liquid Chromatography-Mass Spectrometry |
| LiHMDS | Bis(trimethylsilyl)amine lithium salt |
| Me | Methyl |
| MS | Mass Spectrometry |
| Ms | Methanesulfonyl |
| NMR | Nuclear Magnetic Resonance |
| $Pd_2(dba)_3$ | Tris(dibenzylideneacetone)dipalladium |
| PE | Petroleum Ether |
| PyBOP | Benzotriazol-1-yl-oxytripyrrolidinophosphonium hexafluorophosphate |
| RT | Room Temperature |
| TBAF | Tetrabutylammonium fluoride |
| TBDPS | t-butyldiphenylsilyl |
| TBME | tert-Butyl Methyl Ether |
| t-Bu | tert-butyl |
| TEA | Triethylamine |
| TFA | Trifluoroacetic Acid |
| THF | Tetrahydrofuran |
| TLC | Thin Layer Chromatography |
| TMS | Tetramethylsilane |
| Ts | p-Toluenesulfonyl |
| X-phos | (2-(2,4,6-triisopropylphenethyl)phenyl)dicyclohexylphosphine |

All starting materials, building blocks, reagents, acids, bases, dehydrating agents, solvents, and catalysts utilized to synthesis the compounds of the present disclosure are either commercially available or can be produced by organic synthesis methods known to one of ordinary skill in the art.

Synthesis

General Method A

To a solution of carboxylic acids (1 equiv) and amine (1-2 equiv) in DMF (0.1 M) were added HATU/HBTU/PyBOP (1.2-2 equiv), and TEA/DIEA (2-3 equiv) at RT. The mixture was stirred at RT~100° C. for 4~16 h under $N_2$. The resulting suspension was diluted with EtOAc and washed with brine and then dried ($Na_2SO_4$), filtered and evaporated to dryness. The resulting residue was purified by trituration/Prep-TLC/FCC/Prep-HPLC to give the product.

Example 1: tert-butyl 4-(3,5-difluoro-4-((8-methoxyquinolin-2-yl)carbamoyl)phenyl)piperazine-1-carboxylate

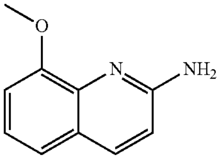

+

-continued

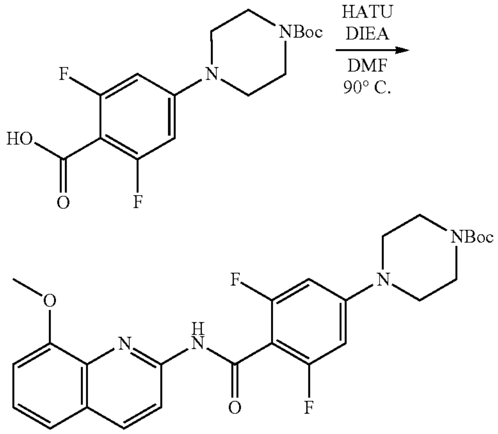

To a solution of compound 4-(4-(tert-butoxycarbonyl) piperazin-1-yl)-2,6-difluorobenzoic acid (3.34 g, 9.770 mmol) and 8-methoxyquinolin-2-amine (1.7 g, 9.770 mmol) in DMF (40 mL) was added HATU (4.46 g, 11.72 mmol), DIEA (2.52 g, 19.54 mmol, 3.2 mL). The mixture was stirred at 90° C. for overnight. The reaction mixture was washed with $H_2O$ (80 mL), the water layer was extracted with EA (80 mL×2), the combined organic layer was washed with brine (200 mL), dried over $Na_2SO_4$, filtered and concentrated to give a residue. The residue was purified by flash silica gel chromatography (PE:EA 3:1). The desired compound (1.79 g, yield: 36.79%) was obtained as a pale yellow solid. MS (ESI) m/z $(M+H)^+$=499.

General Method B

Carboxylic acids (1 equiv), EDCI (2-2.5 equiv), with or without HOBt (2 equiv) and DIEA/pyridine/DMAP (3 equiv) were dissolved in THF or DMF (0.1 M) and stirred for 15-30 min at RT~80° C. Amine (1 equiv) was then added in one portion and the reaction was stirred at RT to 70° C. for 2-16 h. Once the reaction was completed, the resulting suspension was diluted with organic solvent and washed with brine and then dried. After filtration and evaporation, the resulting residue was purified by trituration/Prep-TLC/FCC/Prep-HPLC to give the product.

Example 2: 2,6-difluoro-4-(4-hydroxypiperidin-1-yl)-N-(4-methoxybenzo[d]thiazol-2-yl)benzamide

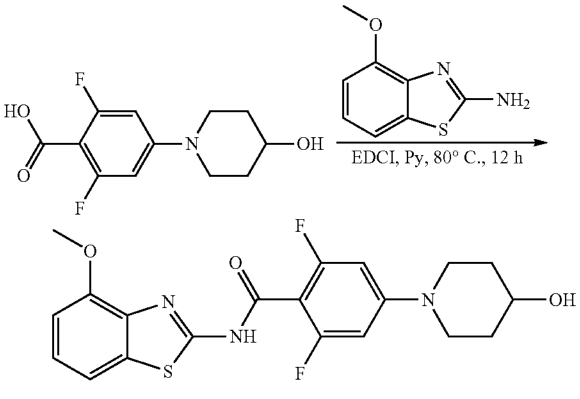

A mixture of 2,6-difluoro-4-(4-hydroxypiperidin-1-yl) benzoic acid (200.0 mg, 777.5 μmol), 4-methoxybenzo[d]

thiazol-2-amine (140.1 mg, 777.5 μmol) and EDCI (298.1 mg, 1.56 mmol) in Py (5 mL) was stirred at 80° C. for 12 h. The mixture was concentrated in vacuum directly. The crude product was purified by prep. HPLC (HCl). The desired compound (63 mg, yield: 19.32%) was obtained as a yellow solid.

$^1H$ NMR (400 MHz, DMSO-$d_6$) δ 12.77 (br s, 1H), 7.56 (d, J=8.0 Hz, 1H), 7.29 (t, J=8.0 Hz, 1H), 7.02 (d, J=7.6 Hz, 1H), 6.72 (d, J=12.8 Hz, 2H), 3.92 (s, 3H), 3.75-3.68 (m, 2H), 3.17 (s, 2H), 3.14-3.05 (m, 2H), 2.07 (s, 1H), 1.83-1.74 (m, 2H), 1.45-1.33 (m, 2H). MS (ESI) m/z $(M+H)^+$=420.1

General Method C

To a solution of carboxylic acids (1 equiv) in DCM (0.01-0.1 M) was added $SOCl_2$ (1 equiv) and DMF (3 equiv). The reaction was stirred at 0° C. for 0.5 h. Then Py (5 equiv) and amine (1 equiv) were added. The reaction mixture was stirred at 25° C. for 24 h. Once judged complete by LCMS analysis, the reaction was quenched with 1M HCl (aq.). The mixture was diluted with EtOAc and washed with brine and then dried ($Na_2SO_4$), filtered and evaporated. The resulting residue was purified by trituration/Prep-TLC/FCC/Prep-HPLC to give the product.

Example 3: Preparation of compound tert-butyl 4-(3,5-difluoro-4-((4-methoxybenzo[d]thiazol-2-yl) carbamoyl)phenyl)piperazine-1-carboxylate

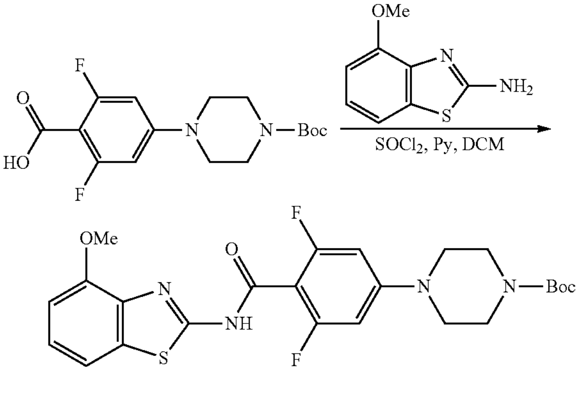

To the solution of 4-(4-tert-butoxycarbonylpiperazin-1-yl)-2,6-difluoro-benzoic acid (1.50 g, 4.38 mmol) in DCM (10 mL) was added $SOCl_2$ (521.0 mg, 4.38 mmol, 317.9 uL) at 0° C. dropwise and the reaction was stirred at 25° C. for 1 h. Py (1.64 g, 20.79 mmol, 1.68 mL) was added and stirred at 25° C. for 0.5 h. 4-methoxy-1,3-benzothiazol-2-amine (674.4 mg, 3.74 mmol) was added to the reaction and the reaction was stirred at 25° C. for 16 h. The reaction was quenched with $H_2O$ (10 mL) and the organic layer was separated. The organic layer was washed with HCl (10 mL×2), sat. $NaHCO_3$ (10 mL), brine (10 mL), dried over anhydrous $Na_2SO_4$, filtered and concentrated under reduced pressure. The obtained residue was purified by silica gel chromatography (Petroleum ether/Ethyl acetate=20/1, 1/1). The desired compound (1.2 g, yield: 57.20%) was obtained as a white solid.

De-BOC General Method

The Boc compounds were dissolved in HCl/MeOH, the reaction mixture was stirred for 1-2 h at RT. The solution was concentrated to dryness to give the final compound.

Example 4: Preparation of 2,6-difluoro-N-(4-methoxybenzo[d]thiazol-2-yl)-4-(piperazin-1-yl) benzamide

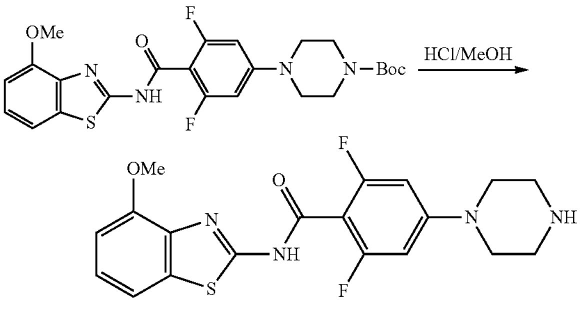

To a solution of tert-butyl 4-(3,5-difluoro-4-((4-methoxybenzo[d]thiazol-2-yl)carbamoyl)phenyl)piperazine-1-carboxylate (200.0 mg, 397 μmol) in DCM (2 mL) was added HCl/MeOH (4 M, 6 mL) at 15° C. The mixture was stirred for 1 h at 15° C. After concentrated in vacuum directly, the residue was purified by prep. HPLC (HCl). The desired compound (88.2 mg, yield: 55.2%) was obtained as a yellow solid.

$^1$H NMR (400 MHz, DMSO-$d_6$) δ 12.94 (br s, 1H), 9.40 (br s, 2H), 7.56 (d, J=7.94 Hz, 1H), 7.32-7.26 (m, 1H), 7.29 (t, J=8.05 Hz, 1H), 7.02 (d, J=8.16 Hz, 1H), 6.84 (br d, J=12.35 Hz, 2H), 3.92 (s, 3H), 3.67-3.55 (m, 4H), 3.18 (br s, 4H). MS (ESI) m z $(M+Na)^+$=427.0.

Example 5: Preparation of 2-fluoro-N-(4-methoxybenzo[d]thiazol-2-yl)-6-methyl-4-(piperazin-1-yl) benzamide

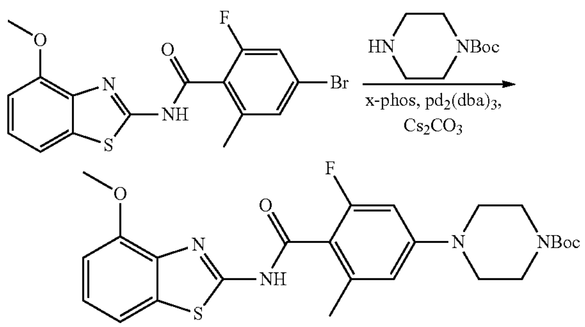

A solution of 4-bromo-2-fluoro-N-(4-methoxybenzo[d]thiazol-2-yl)-6-methylbenzamide (150.0 mg, 0.38 mmol), tert-butyl piperazine-1-carboxylate (71 mg, 0.38 mmol), x-phos (36.0 mg, 0.2 mmol), $Pd_2(dba)_3$ (39.0 mg, 0.1 mmol) and $Cs_2CO_3$ (247.0 mg, 0.76 mmol) in toluene (5 ml), the mixture was stirred at 110° C. overnight. Once judged complete by TLC analysis, the resulting suspension was diluted with EtOAc and washed with brine and then dried ($Na_2SO_4$), filtered and evaporated to dryness. The resulting residue was purified by trituration, FCC or Prep-TLC to give the product.

TABLE 1

Compounds of benzothiazole derivatives (Formula I) and assay results

| Com. ID | Structure Name | $^1$H NMR/ LCMS | Human HTRF $IC_{50}$ nM | NFκB Assay $IC_{50}$ μM |
|---|---|---|---|---|
| T001 | 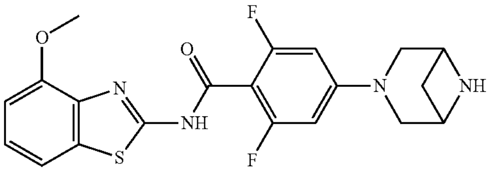 4-(3,6-diazabicyclo[3.1.1]heptan-3-yl)-2,6-difluoro-N-(4-methoxybenzo[d]thiazol-2-yl)benzamide | —/ $[M + H]^+$ = 417 | 95 | 1.31 |
| T002 | 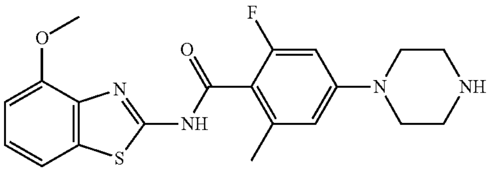 [SMILES: COc1cccc2sc(NC(=O)c3c(C)cc(N4CCNCC4)cc3F)nc12] 2-fluoro-N-(4-methoxybenzo[d]thiazol-2-yl)-6-methyl-4-(piperazin-1-yl)benzamide | —/ $[M + H]^+$ = 401 | 176 | 2.46 |

TABLE 1-continued

| Com. ID | Structure Name | $^1$H NMR/ LCMS | Human HTRF $IC_{50}$ nM | NFκB Assay $IC_{50}$ μM |
|---|---|---|---|---|
| | Compounds of benzothiazole derivatives (Formula I) and assay results | | | |
| T003 | 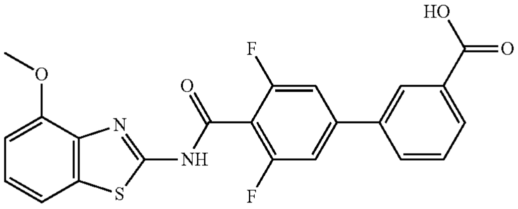 [SMILES: COc1cccc2sc(NC(=O)c3c(F)cc(-c4cccc(C(=O)O)c4)cc3F)nc12] 3',5'-difluoro-4'-((4-methoxybenzo[d]thiazol-2-yl)carbamoyl)-[1,1'-biphenyl]-3-carboxylic acid | —/ [M + H]$^+$ = 441 | 159 | 1.49 |
| T004 | 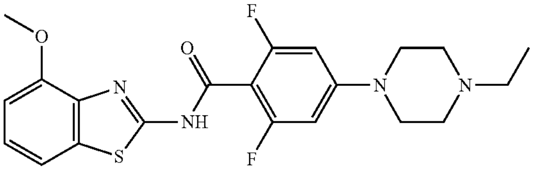 [SMILES: CCN1CCN(c2cc(F)c(C(=O)Nc3nc4c(OC)cccc4s3)c(F)c2)CC1] 4-(4-ethylpiperazin-1-yl)-2,6-difluoro-N-(4-methoxybenzo[d]thiazol-2-yl)benzamide | —/[M + H]$^+$ = 433 | 131 | 1.98 |
| T005 | 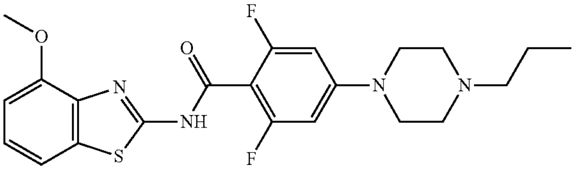 [SMILES: CCCN1CCN(c2cc(F)c(C(=O)Nc3nc4c(OC)cccc4s3)c(F)c2)CC1] 2,6-difluoro-N-(4-methoxybenzo[d]thiazol-2-yl)-4-(4-propylpiperazin-1-yl)benzamide | —/[M + H]$^+$ = 447 | 81 | 2.42 |
| T007 | 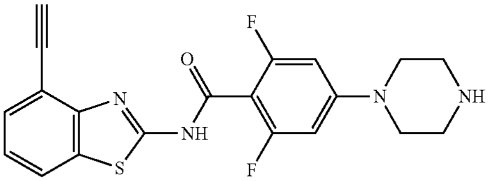 [SMILES: C#Cc1cccc2sc(NC(=O)c3c(F)cc(N4CCNCC4)cc3F)nc12] N-(4-ethynylbenzo[d]thiazol-2-yl)-2,6-difluoro-4-(piperazin-1-yl)benzamide | 1H NMR (400 MHz, DMSO-d6) δ 13.21 (br s, 1 H), 9.51 (br s, 2 H), 8.02-8.13 (m, 1 H), 7.54-7.63 (m, 1 H), 7.33 (t, J = 7.78 Hz, 1 H), 6.83 (d, J = 12.30 Hz, 2 H), 4.43 (s, 1 H), 3.57-3.70 (m, 4 H), 3.17 (br s, 4 H). [M + H]$^+$ = 399 | 4 | 0.47 |
| T008 | 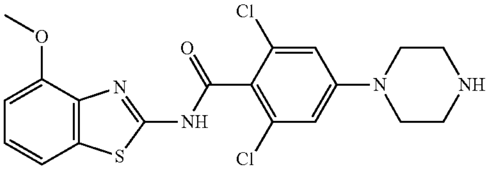 2,6-dichloro-N-(4-methoxybenzo[d]thiazol-2-yl)-4-(piperazin-1-yl)benzamide | —/ [M + H]$^+$ = 437 | 57 | 1.95 |
| T009 | 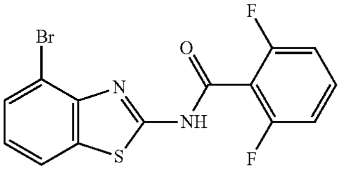 [SMILES: O=C(Nc1nc2c(Br)cccc2s1)c1c(F)cccc1F] N-(4-bromobenzo[d]thiazol-2-yl)-2,6- | —/ [M + H]$^+$ = 371 | 415 | 5.86 |

TABLE 1-continued

Compounds of benzothiazole derivatives (Formula I) and assay results

| Com. ID | Structure Name | $^1$H NMR/ LCMS | Human HTRF $IC_{50}$ nM | NFκB Assay $IC_{50}$ μM |
|---|---|---|---|---|
| | difluorobenzamide | | | |
| T010 | 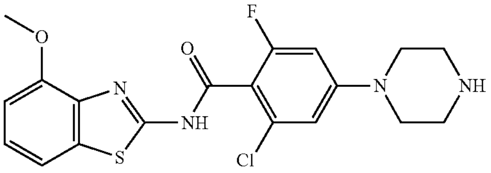 [SMILES: COc1cccc2sc(NC(=O)c3c(F)cc(N4CCNCC4)cc3Cl)nc12] 2-chloro-6-fluoro-N-(4-methoxybenzo[d]thiazol-2-yl)-4-(piperazin-1-yl)benzamide | —/[M + H]$^+$ = 421 | 49 | 1.64 |
| T011 | 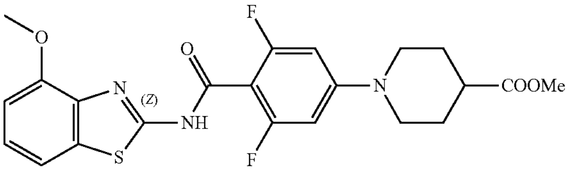 methyl 1-(3,5-difluoro-4-((4-methoxybenzo[d]thiazol-2-yl)carbamoyl)phenyl)piperidine-4-carboxylate | —/[M + H]$^+$ = 462 | 420 | 6.65 |
| T012 | 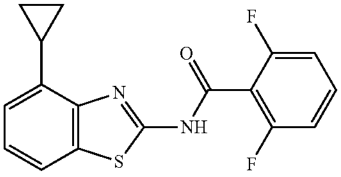 [SMILES: O=C(Nc1nc2c(C3CC3)cccc2s1)c1c(F)cccc1F] N-(4-cyclopropylbenzo[d]thiazol-2-yl)-2,6-difluorobenzamide | —/[M + H]$^+$ = 331 | 970 | 5.95 |
| T013 | 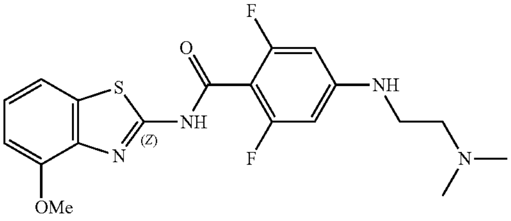 4-((2-(dimethylamino)ethyl)amino)-2,6-difluoro-N-(4-methoxybenzo[d]thiazol-2-yl)benzamide | —/ [M + H]$^+$ = 407 | 507 | 5.22 |
| T014 | 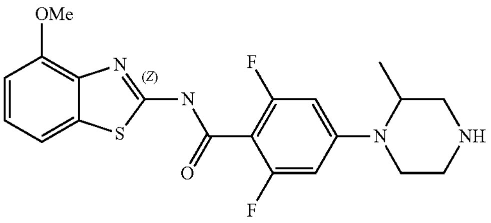 2,6-difluoro-N-(4-methoxybenzo[d]thiazol-2-yl)-4-(2-methylpiperazin-1-yl)benzamide | —/ [M + H]$^+$ = 419 | 92 | 1.31 |

TABLE 1-continued

Compounds of benzothiazole derivatives (Formula I) and assay results

| Com. ID | Structure Name | $^1H$ NMR/ LCMS | Human HTRF $IC_{50}$ nM | NFκB Assay $IC_{50}$ μM |
|---|---|---|---|---|
| T015 | 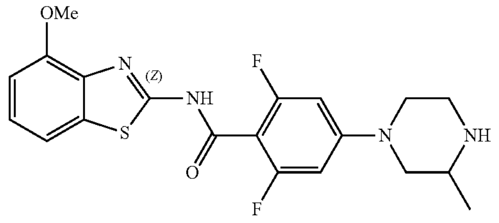 2,6-difluoro-N-(4-methoxybenzo[d]thiazol-2-yl)-4-(3-methylpiperazin-1-yl)benzamide | —/ $[M + H]^+ = 419$ | 349 | 4.47 |
| T016 | 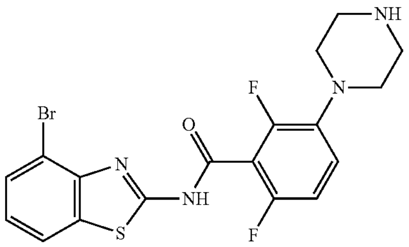 [SMILES: O=C(Nc1nc2c(Br)cccc2s1)c1c(F)ccc(N2CCNCC2)c1F] N-(4-bromobenzo[d]thiazol-2-yl)-2,6-difluoro-3-(piperazin-1-yl)benzamide | $[M + H]^+ = 453$ | 47 | 2.22 |
| T017 | 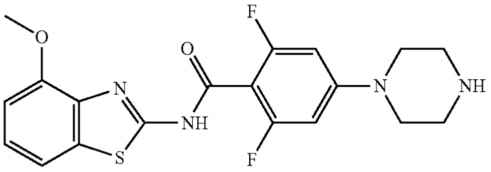 2,6-difluoro-N-(4-methoxybenzo[d]thiazol-2-yl)-4-(piperazin-1-yl)benzamide hydrochloride | (400 MHz, DMSO-$d_6$) δ 12.94 (br s, 1 H), 9.40 (br s, 2 H), 7.56 (d, J = 7.94 Hz, 1 H), 7.29 (t, J = 8.05 Hz, 1 H), 7.02 (d, J = 8.16 Hz, 1 H), 6.84 (br d, J = 12.35 Hz, 2 H), 3.92 (s, 3 H), 3.67-3.55(m, 4 H), 3.18 (br s, 4 H)/ $[M + Na]^+ = 427.0$ | 14 | 0.69 |
| T018 | 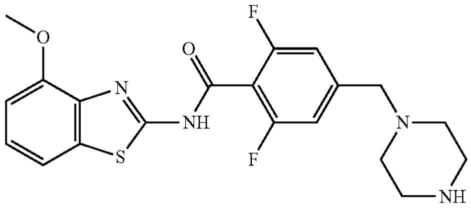 2,6-difluoro-N-(4-methoxybenzo[d]thiazol-2-yl)-4-(piperazin-1-ylmethyl)benzamide | (400 MHz, Methanol-$d_4$) δ 7.43-7.52 (m, 3 H) 7.32 (t, J = 7.95 Hz, 1 H) 7.02 (d, J = 7.83 Hz, 1 H) 4.40 (s, 2H) 3.99 (s, 3 H) 3.53-3.64 (m, 4 H) 3.45 (br s, 4 H)/ $[M + H]^+ = 419.2$ | 148 | 2.46 |
| T019 | 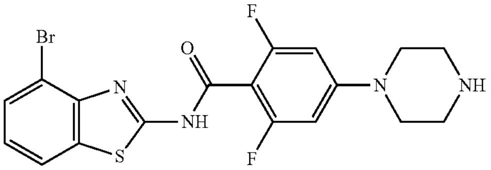 N-(4-bromobenzo[d]thiazol-2-yl)-2,6-difluoro-4-(piperazin-1-yl)benzamide hydrochloride | (400 MHz, DMSO-$d_6$) δ 13.24 (s, 1 H), 9.31 (br s, 2 H), 8.05 (d, J = 7.94 Hz, 1 H), 7.71 (d, J = 7.72 Hz, 1 H), 7.27 (t, J = 7.94 Hz, 1 H), 6.84 (br d, J = 12.35 Hz, 2 H), 3.60-3.63 (m, 4 H), 3.19 (br s, 4 H)/ $[M + H]^+ = 453.0$ | 11 | 0.76 |

TABLE 1-continued

Compounds of benzothiazole derivatives (Formula I) and assay results

| Com. ID | Structure Name | $^1$H NMR/ LCMS | Human HTRF $IC_{50}$ nM | NFκB Assay $IC_{50}$ μM |
|---|---|---|---|---|
| T020 | 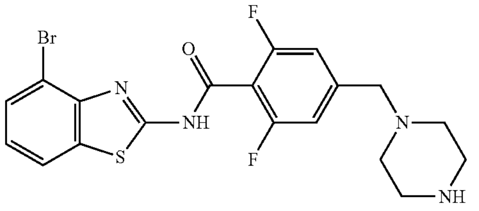 [SMILES: O=C(Nc1nc2c(Br)cccc2s1)c1c(F)cc(CN2CCNCC2)cc1F] N-(4-bromobenzo[d]thiazol-2-yl)-2,6-difluoro-4-(piperazin-1-ylmethyl)benzamide | (400 MHz, DMSO-$d_6$) δ 7.79 (d, J = 7.50 Hz, 1 H) 7.51 (d, J = 7.72 Hz, 1 H) 6.96-7.09 (m, 3 H) 3.51 (s, 2 H) 2.96 (br s, 4 H) 2.43 (br s, 4 H)/ $[M + H]^+$ = 467.1 | 100 | 1.57 |
| T021 | 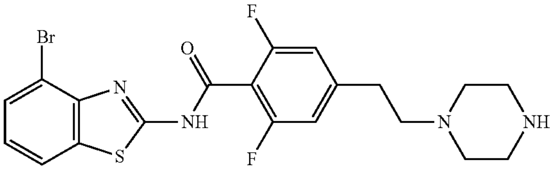 [SMILES: O=C(Nc1nc2c(Br)cccc2s1)c1c(F)cc(CCN2CCNCC2)cc1F] N-(4-bromobenzo[d]thiazol-2-yl)-2,6-difluoro-4-(2-(piperazin-1-yl)ethyl)benzamide | (400 MHz, Methanol-$d_4$) δ 7.94(d, J = 8.00, 1H), 7.69(d, J = 7.60, 1H), 7.29-7.23(m, 3H), 3.71-3.58(m, 10H), 3.30-3.28(m, 2H)/ $[M + H]^+$ = 481.0 | 148 | 1.20 |
| T022 | 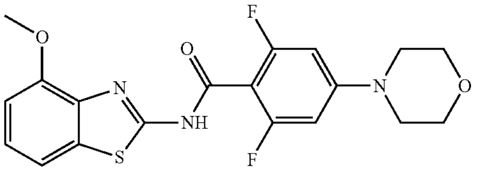 [SMILES: COc1cccc2sc(NC(=O)c3c(F)cc(N4CCOCC4)cc3F)nc12] 2,6-difluoro-N-(4-methoxybenzo[d]thiazol-2-yl)-4-morpholinobenzamide | (400 MHz, DMSO-$d_6$) δ 12.89 (s, 1H), 7.56 (d, J = 7.3 Hz, 1H), 7.29 (t, J = 7.9 Hz, 1H), 7.02 (d, J = 7.7 Hz, 1H), 6.77 (br d, J = 12.6 Hz, 2H), 3.92 (s, 3H), 3.76-3.63 (m, 4H), 3.32-3.29 (m, 4H)/ $[M + H]^+$ = 406.0 | 295 | 2.01 |
| T023 | 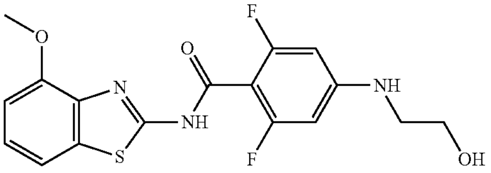 [SMILES: COc1cccc2sc(NC(=O)c3c(F)cc(NCCO)cc3F)nc12] 2,6-difluoro-4-((2-hydroxyethyl)amino)-N-(4-methoxybenzo[d]thiazol-2-yl)benzamide | (400 MHz, DMSO-$d_6$) δ 12.67 (br s, 1H), 7.54 (d, J = 7.94 Hz, 1H), 7.27 (t, J = 7.94 Hz, 1H), 7.01 (d, J = 7.94 Hz, 1H), 6.35 (br d, J = 12.57 Hz, 2H), 3.91 (s, 3H), 3.15 (br t, J = 5.40 Hz, 2H), 2.54 (br s, 2H)/ $[M + H]^+$ = 380.1 | 289 | 4.30 |
| T024 | 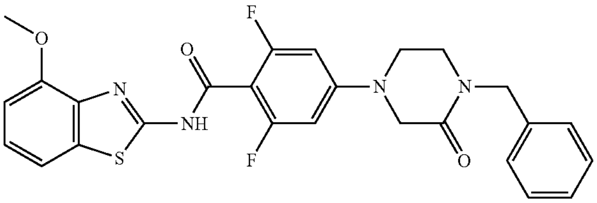 [SMILES: COc1cccc2sc(NC(=O)c3c(F)cc(N4CCN(Cc5ccccc5)C(=O)C4)cc3F)nc12] 4-(4-benzyl-3-oxopiperazin-1-yl)-2,6-difluoro-N-(4-methoxybenzo[d]thiazol-2-yl)benzamide | (400 MHz, DMSO-$d_6$) δ 7.53 (s, 1 H), 7.22-7.40 (m, 6 H), 7.18-7.42 (m, 1 H), 7.01 (br d, J = 7.72 Hz, 1 H), 6.73 (br d, J = 12.35 Hz, 2 H), 4.61 (s, 2 H), 4.07 (s, 2 H), 3.91 (s, 3 H), 3.62 (br t, J = 5.07 Hz, 2 H), 3.43-3.48 (m, 2 H)/ $[M + H]^+$ = 509 | 321 | 1.15 |

TABLE 1-continued

Compounds of benzothiazole derivatives (Formula I) and assay results

| Com. ID | Structure Name | $^1$H NMR/ LCMS | Human HTRF $IC_{50}$ nM | NFκB Assay $IC_{50}$ μM |
|---|---|---|---|---|
| T025 | 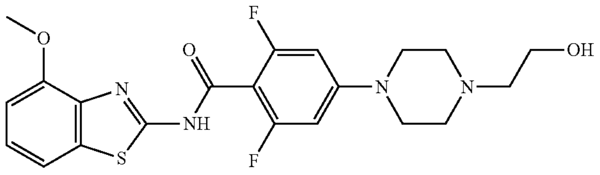 [SMILES: COc1cccc2sc(NC(=O)c3c(F)cc(N4CCN(CCO)CC4)cc3F)nc12] 2,6-difluoro-4-(4-(2-hydroxyethyl)piperazin-1-yl)-N-(4-methoxybenzo[d]thiazol-2-yl)benzamide | (400 MHz, DMSO-$d_6$)12.84 (br s, 1H), 7.55 (d, J = 7.8 Hz, 1H), 7.28 (t, J = 8.0 Hz, 1H), 7.01 (d, J = 8.0 Hz, 1H), 6.73 (br d, J = 12.5 Hz, 2H), 4.53 (br s, 1H), 3.91 (s, 3H), 3.53 (q, J = 5.7 Hz, 2H), 3.33 (br s, 8H), 2.44 ppm (br d, J = 6.0 Hz, 2H)/ $[M + H]^+$ = 449.2 | 148 | 2.92 |
| T026 | 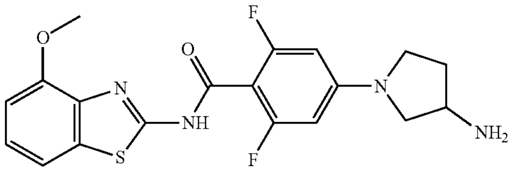 [SMILES: COc1cccc2sc(NC(=O)c3c(F)cc(N4CCC(N)C4)cc3F)nc12] 4-(3-aminopyrrolidin-1-yl)-2,6-difluoro-N-(4-methoxybenzo[d]thiazol-2-yl)benzamide | (400 MHz, DMSO-$d_6$) δ 12.84 (s, 1H), 8.27 (br s, 2H), 7.53 (br d, J = 8.2 Hz, 1H), 7.26 (br t, J = 8.0 Hz, 1H), 6.99 (br d, J = 7.9 Hz, 1H), 6.36 (br d, J = 11.7 Hz, 2H), 3.89 (s, 3H), 3.64-3.43 (m, 4H), 2.10 (br s, 2H)/ $[M + H]^+$ = 405.1 | 125 | 2.38 |
| T027 | 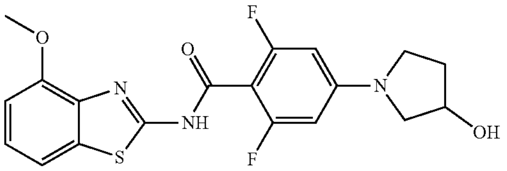 [SMILES: COc1cccc2sc(NC(=O)c3c(F)cc(N4CCC(O)C4)cc3F)nc12] 2,6-difluoro-4-(3-hydroxypyrrolidin-1-yl)-N-(4-methoxybenzo[d]thiazol-2-yl)benzamide | (400 MHz, DMSO-$d_6$) δ 12.73 (br s, 1H), 7.55 (d, J = 7.8 Hz, 1H), 7.28 (t, J = 7.9 Hz, 1H), 7.01 (d, J = 7.8 Hz, 1H), 6.30 (br d, J = 12.2 Hz, 2H), 4.41 (br s, 1H), 3.92 (s, 3H), 3.38-3.35 (m, 6H) / $[M + H]^+$ = 406 | 1172 | 3.65 |
| T028 | 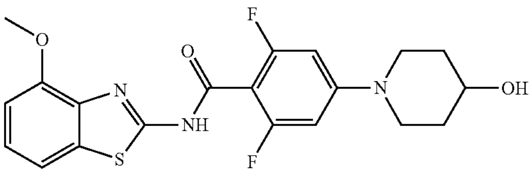 [SMILES: COc1cccc2sc(NC(=O)c3c(F)cc(N4CCC(O)CC4)cc3F)nc12] 2,6-difluoro-4-(4-hydroxypiperidin-1-yl)-N-(4-methoxybenzo[d]thiazol-2-yl)benzamide | (400 MHz, DMSO-$d_6$) δ 12.77 (br s, 1 H), 7.56 (d, J = 8.0 Hz, 1 H), 7.29 (t, J = 8.0 Hz, 1 H), 7.02 (d, J = 7.6 Hz, 1 H), 6.72 (d, J = 12.8 Hz, 2 H), 3.92 (s, 3 H), 3.75-3.68 (m, 2H), 3.17 (s, 2 H), 3.14-3.05 (m, 2 H), 2.07 (s, 1 H), 1.83-1.74 (m, 2 H), 1.45-1.33 (m, 2 H)/ $[M + H]^+$ = 420.1 | 248 | 1.49 |
| T029 | 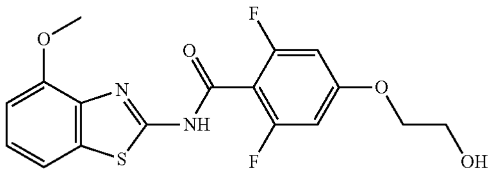 [SMILES: COc1cccc2sc(NC(=O)c3c(F)cc(OCCO)cc3F)nc12] 2,6-difluoro-4-(2-hydroxyethoxy)-N-(4-methoxybenzo[d]thiazol-2-yl)benzamide | (400 MHz, DMSO-$d_6$) δ13.13 (br s, 1 H) 7.58 (d, J = 7.6 Hz, 1 H), 7.31 (t, J = 7.6 Hz, 1 H), 7.03 (d, J = 8.0 Hz, 1 H), 6.91 (d, J = 10.0 Hz, 2 H), 4.10 (t, J = 4.8 Hz, 2 H), 3.92 (s, 3 H), 3.75-3.72(m, 3 H)/ $[M + H]^+$ = 381.1 | 560 | 2.99 |

TABLE 1-continued

| Compounds of benzothiazole derivatives (Formula I) and assay results | | | | |
|---|---|---|---|---|
| Com. ID | Structure Name | $^1H$ NMR/ LCMS | Human HTRF $IC_{50}$ nM | NFκB Assay $IC_{50}$ μM |
| T030 | 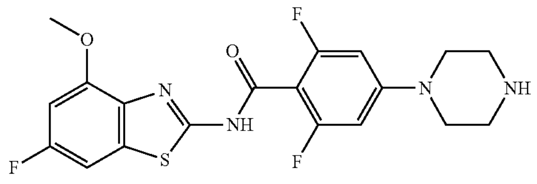 [SMILES: COc1cc(F)cc2sc(NC(=O)c3c(F)cc(N4CCNCC4)cc3F)nc12] 2,6-difluoro-N-(6-fluoro-4-methoxybenzo[d]thiazol-2-yl)-4-(piperazin-1-yl)benzamide | (400 MHz, DMSO-$d_6$) δ 12.97 (br s, 1H), 9.36 (br s, 2H), 7.47 (dd, J = 2.1, 8.4 Hz, 1H), 6.98 (dd, J = 2.0, 11.5 Hz, 1H), 6.85 (br d, J = 12.3 Hz, 2H), 3.93 (s, 3H), 3.62 (br d, J = 4.3 Hz, 4H), 3.18 (br s, 4H)/ $[M + H]^+$ = 423 | 318 | 2.22 |
| T033 | 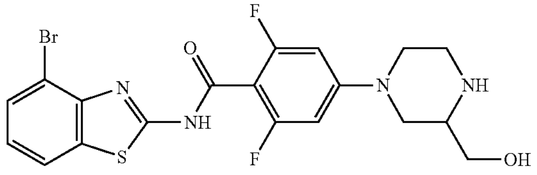 [SMILES: O=C(Nc1nc2c(Br)cccc2s1)c1c(F)cc(N2CCNC(CO)C2)cc1F] N-(4-bromobenzo[d]thiazol-2-yl)-2,6-difluoro-4-(3-(hydroxymethyl)piperazin-1-yl)benzamide | (400 MHz, DMSO-$d_6$) δ 13.25 (s, 1 H), 9.50 (br d, J = 8.70 Hz, 1 H), 9.26 (br d, J = 9.18 Hz, 1 H), 8.06 (dd, J = 7.99, 0.95 Hz, 1 H), 7.72 (dd, J = 7.75, 0.95 Hz, 1 H), 7.28 (t, J = 7.87 Hz, 1 H), 6.86 (d, J = 12.40 Hz, 2 H), 3.95-4.09 (m, 2 H), 3.71-3.67 (m, 4 H), 3.20-3.33 (m, 2 H), 3.11 (br dd, J = 13.59, 11.09 Hz, 1 H)/ $[M + H]^+$ = 483 | 38 | 1.33 |
| T035 | 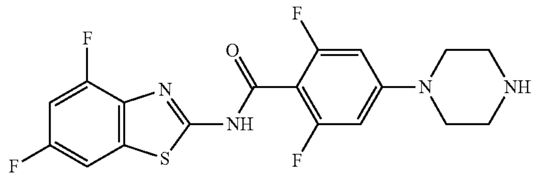 [SMILES: O=C(Nc1nc2c(F)cc(F)cc2s1)c1c(F)cc(N2CCNCC2)cc1F] N-(4,6-difluorobenzo[d]thiazol-2-yl)-2,6-difluoro-4-(piperazin-1-yl)benzamide | (400 MHz, DMSO-$d_6$)13.12 (s, 1H), 9.09 (br s, 1H), 7.83 (br d, J = 6.6 Hz, 1H), 7.34-7.47 (m, 1H), 6.84 (br d, J = 12.6 Hz, 2H), 3.58 (br s, 4H), 3.17 ppm (br s, 4H)/ $[M + H]^+$ = 411.0 | 1338 | 5.02 |
| T038 | 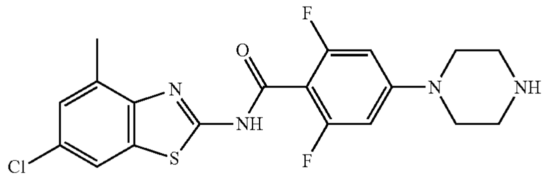 [SMILES: Cc1cc(Cl)cc2sc(NC(=O)c3c(F)cc(N4CCNCC4)cc3F)nc12] N-(6-chloro-4-methylbenzo[d]thiazol-2-yl)-2,6-difluoro-4-(piperazin-1-yl)benzamide | (400 MHz, DMSO-$d_6$) δ 13.04 (s, 1 H), 9.08 (br s, 2 H), 7.98 (d, J = 1.67 Hz, 1 H), 7.35 (s, 1 H), 6.84 (br d, J = 12.16 Hz, 2 H), 3.59 (br d, J = 4.77 Hz, 4 H), 3.19 (br s, 4 H), 2.58 (s, 3 H)/ $[M + H]^+$ = 423 | 255 | 9.98 |
| T040 | 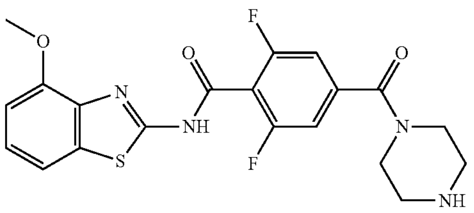 [SMILES: COc1cccc2sc(NC(=O)c3c(F)cc(C(=O)N4CCNCC4)cc3F)nc12] 2,6-difluoro-N-(4-methoxybenzo[d]thiazol-2-yl)-4-(piperazine-1-carbonyl)benzamide | (400 MHz, Methanol-$d_4$) δ 7.54-7.51 (m, 1 H), 7.40-7.33 (m, 3 H), 7.06 (d, J = 7.6 Hz, 1 H), 4.03 (s, 3 H), 4.01- 3.56 (m, 4 H), 3.42- 3.34 (m, 4 H) $[M + H]^+$ = 433.1 | 341 | 6.33 |

TABLE 1-continued

Compounds of benzothiazole derivatives (Formula I) and assay results

| Com. ID | Structure Name | $^1H$ NMR/ LCMS | Human HTRF $IC_{50}$ nM | NFκB Assay $IC_{50}$ μM |
|---|---|---|---|---|
| T041 | 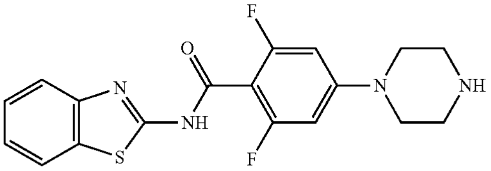 [SMILES: O=C(Nc1nc2ccccc2s1)c1c(F)cc(N2CCNCC2)cc1F] N-(benzo[d]thiazol-2-yl)-2,6-difluoro-4-(piperazin-1-yl)benzamide | (400 MHz, Methanol-$d_4$)7.93 (d, J = 7.4 Hz, 1H), 7.79 (d, J = 7.9 Hz, 1H), 7.43-7.53 (m, 1H), 7.33-7.41 (m, 1H), 6.79 (d, J = 11.8 Hz, 2H), 3.62-3.67 (m, 4H), 3.35-3.40 ppm (m, 4H) $[M + H]^+$ = 475.0 | 467 | 3.96 |
| T043 | 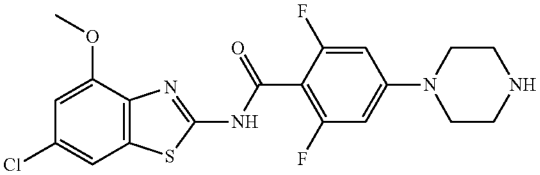 [SMILES: COc1cc(Cl)cc2sc(NC(=O)c3c(F)cc(N4CCNCC4)cc3F)nc12] N-(6-chloro-4-methoxybenzo[d]thiazol-2-yl)-2,6-difluoro-4-(piperazin-1-yl)benzamide | (400 MHz, DMSO-$d_6$) δ 13.04 (s, 1H), 9.17 (br s, 2H), 7.73 (d, J = 1.8 Hz, 1H), 7.09 (d, J = 1.8 Hz, 1H), 6.85 (d, J = 12.3 Hz, 2H), 3.94 (s, 3H), 3.65-3.57 (m, 4H), 3.19 (br s, 4H) $[M + H]^+$ = 439 | 401 | 3.98 |
| T044 | 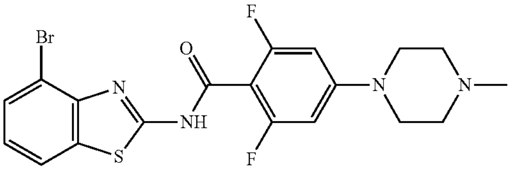 [SMILES: CN1CCN(c2cc(F)c(C(=O)Nc3nc4c(Br)cccc4s3)c(F)c2)CC1] N-(4-bromobenzo[d]thiazol-2-yl)-2,6-difluoro-4-(4-methylpiperazin-1-yl)benzamide | (400 MHz, DMSO-$d_6$) δ 13.24 (s, 1 H), 11.04 (br s, 1 H), 7.97-8.08 (m, 1H), 7.63-7.72 (m, 1 H), 7.24 (t, J = 7.83 Hz, 1 H), 6.84 (br d, J = 12.13 Hz, 2 H), 4.06 (br d, J = 13.45 Hz, 2 H), 3.43-3.49 (m, 2 H), 3.27 (br t, J = 12.35 Hz, 2 H), 3.00-3.12 (m, 2 H), δ 2.76 (br d, J = 3.97 Hz, 3 H). $[M + Na]^+$ = 491.1 | 13 | 1.09 |
| T045 | 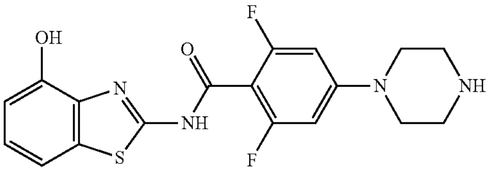 [SMILES: O=C(Nc1nc2c(O)cccc2s1)c1c(F)cc(N2CCNCC2)cc1F] 2,6-difluoro-N-(4-hydroxybenzo[d]thiazol-2-yl)-4-(piperazin-1-yl)benzamide | (400 MHz, DMSO-$d_6$) δ 9.52 (br s, 2 H), 8.19 (br s, 1 H), 7.66 (dd, J = 6.11, 2.93 Hz, 1 H), 7.02-7.18 (m, 2 H), 6.87 (d, J = 13.45 Hz, 2 H), 3.64-3.74 (m, 4 H), δ 3.17 (br s, 4 H). $[M + H]^+$ = 391.1 | 1650 | 4.15 |
| T046 | 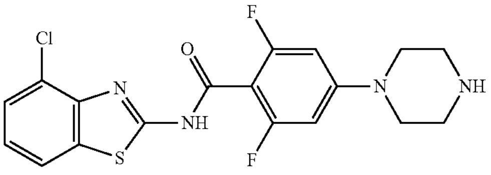 N-(4-chlorobenzo[d]thiazol-2-yl)-2,6-difluoro-4-(piperazin-1-yl)benzamide | (400 MHz, Methanol-$d_4$) δ 7.84 (dd, J = 7.94, 0.88 Hz, 1 H), 7.47 (dd, J = 7.72, 0.88 Hz, 1 H), 7.28 (t, J = 7.94 Hz, 1 H), 6.75 (d, J = 11.91 Hz, 2 H), 3.57-3.66 (m, 4 H) 3.33-3.38 (m, 4 H). $[M + H]^+$ = 409 | 56 | 1.32 |

TABLE 1-continued

Compounds of benzothiazole derivatives (Formula I) and assay results

| Com. ID | Structure Name | $^1$H NMR/ LCMS | Human HTRF $IC_{50}$ nM | NFκB Assay $IC_{50}$ μM |
|---|---|---|---|---|
| T047 | 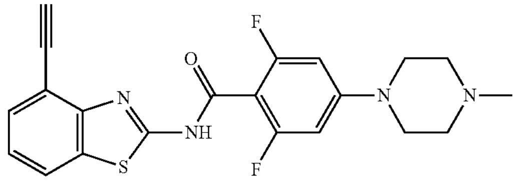 [SMILES: C#Cc1cccc2sc(NC(=O)c3c(F)cc(N4CCN(C)CC4)cc3F)nc12] N-(4-ethynylbenzo[d]thiazol-2-yl)-2,6-difluoro-4-(4-methylpiperazin-1-yl)benzamide | (400 MHz, $CDCl_3$) δ 10.45 (br. s, 1H), 7.88-7.80 (m, 1H), 7.60-7.48 (m, 1H), 7.30-7.23 (m, 1H), 6.36 (s, 1H), 6.32 (s, 1H), 3.46 (s, 1H), 3.38-3.27 (m, 4H), 2.58-2.50 (m, 4H), 2.36 (s, 3H)/ $[M + H]^+$ = 413.1; $[M + Na]^+$ = 435.0 | 13 | 0.81 |
| T048 | 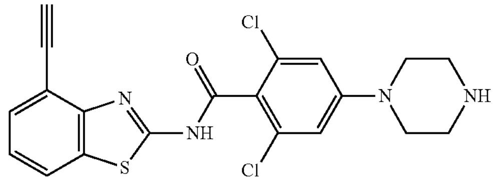 [SMILES: C#Cc1cccc2sc(NC(=O)c3c(Cl)cc(N4CCNCC4)cc3Cl)nc12] 2,6-dichloro-N-(4-ethynylbenzo[d]thiazol-2-yl)-4-(piperazin-1-yl)benzamide | (400 MHz, DMSO-$d_6$) δ 8.00 (d, 1 H), 7.71 (d, 1 H), 7.50 (t, 1 H), 7.01 (s, 2 H), 3.18 (t, 4 H), 2.76 (t, 4 H) $[M + H]^+$ = 431.0 | 9 | 7.13 |
| T049 | 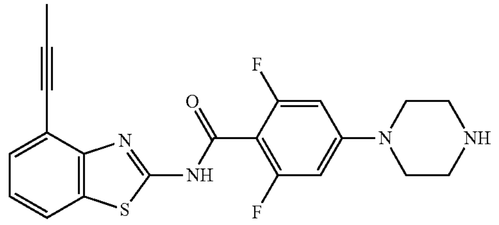 [SMILES: CC#Cc1cccc2sc(NC(=O)c3c(F)cc(N4CCNCC4)cc3F)nc12] 2,6-difluoro-4-(piperazin-1-yl)-N-(4-(prop-1-yn-1-yl)benzo[d]thiazol-2-yl)benzamide | 1H NMR (400 MHz, DMSO-d6) δ 7.94 (d, J = 8.0 Hz, 1H), 7.45 (d, J = 8.0 Hz, 1H), 7.26 (t, J = 16.0 Hz, 1H), 6.68 (d, J = 16.0 Hz, 2H), 3.21 (s, 4H), 2.77 (s, 4H), 2.08 (s, 3H). $[M + H]^+$ = 413.1 | 43 | 2.10 |
| T050 | 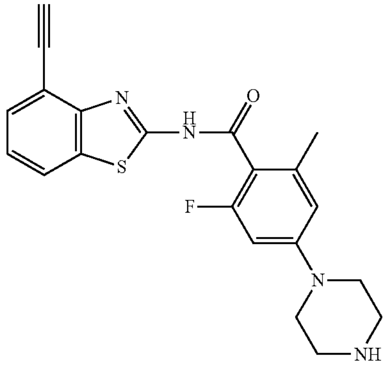 [SMILES: C#Cc1cccc2sc(NC(=O)c3c(C)cc(N4CCNCC4)cc3F)nc12] N-(4-ethynylbenzo[d]thiazol-2-yl)-2-fluoro-6-methyl-4-(piperazin-1-yl)benzamide | | 98 | 0.96 |

TABLE 1-continued

Compounds of benzothiazole derivatives (Formula I) and assay results

| Com. ID | Structure Name | $^1$H NMR/ LCMS | Human HTRF $IC_{50}$ nM | NFκB Assay $IC_{50}$ μM |
|---|---|---|---|---|
| T051 | 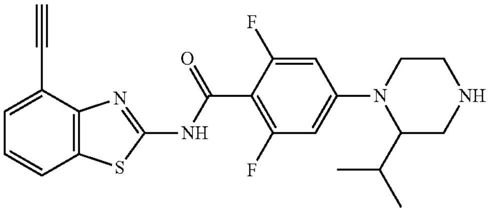 [SMILES: C#Cc1cccc2sc(NC(=O)c3c(F)cc(N4CCNCC4C(C)C)cc3F)nc12] N-(4-ethynylbenzo[d]thiazol-2-yl)-2,6-difluoro-4-(2-isopropylpiperazin-1-yl)benzamide | $[M + H]^+ = 441$ | 56 | 1.59 |
| T052 | 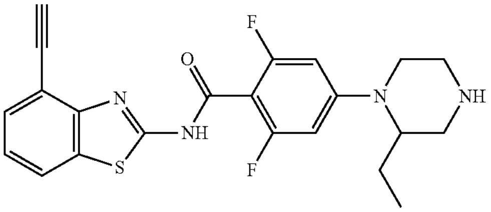 [SMILES: C#Cc1cccc2sc(NC(=O)c3c(F)cc(N4CCNCC4CC)cc3F)nc12] 4-(2-ethylpiperazin-1-yl)-N-(4-ethynylbenzo[d]thiazol-2-yl)-2,6-difluorobenzamide | $[M + H]^+ = 427$ | 58 | 1.32 |
| T053 | 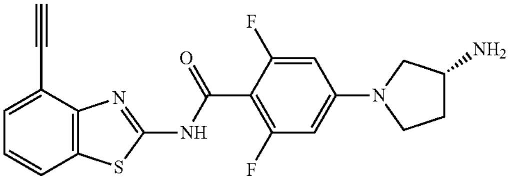 [SMILES: C#Cc1cccc2sc(NC(=O)c3c(F)cc(N4CC[C@@H](N)C4)cc3F)nc12] (R)-4-(3-aminopyrrolidin-1-yl)-N-(4-ethynylbenzo[d]thiazol-2-yl)-2,6-difluorobenzamide | $[M + H]^+ = 399$ | 83 | 0.89 |
| T054 | 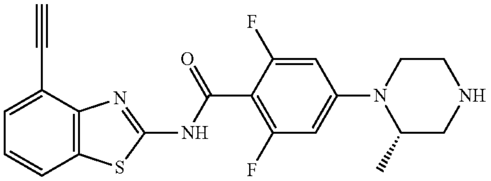 [SMILES: C#Cc1cccc2sc(NC(=O)c3c(F)cc(N4CCNC[C@@H]4C)cc3F)nc12] (S)-N-(4-ethynylbenzo[d]thiazol-2-yl)-2,6-difluoro-4-(2-methylpiperazin-1-yl)benzamide | $^1$H NMR (400 MHz, DMSO-$d_6$) δ 8.07 (d, J = 7.6 Hz, 1H), 7.58 (d, J = 6.6 Hz, 1H), 7.34 (d, J = 7.4 Hz, 1H), 6.71 (d, J = 13.1 Hz, 2H), 4.43 (s, 1H), 3.62 (d, J = 12.1 Hz, 2H), 3.11 (d, J = 11.6 Hz, 2H), 2.99 (s, 2H), 2.81 (d, J = 10.2 Hz, 1H), 1.14 (d, J = 5.2 Hz, 3H). $[M + H]^+ = 413$ | 36 | 0.27 |

TABLE 1-continued

| Compounds of benzothiazole derivatives (Formula I) and assay results | | | | |
|---|---|---|---|---|
| Com. ID | Structure Name | $^1$H NMR/ LCMS | Human HTRF $IC_{50}$ nM | NFκB Assay $IC_{50}$ μM |
| T055 | 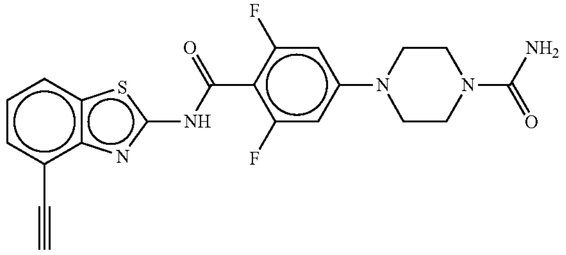 4-(4-((4-ethynylbenzo[d]thiazol-2-yl)carbamoyl)-3,5-difluorophenyl)piperazine-1-carboxamide | $[M + H]^+$ = 442 | 126 | 2.15 |
| T056 | 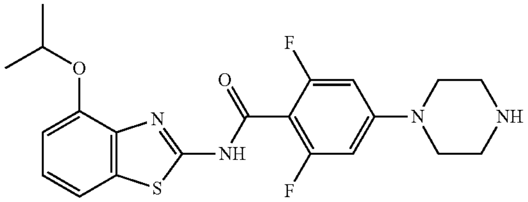 [SMILES: CC(C)Oc1cccc2sc(NC(=O)c3c(F)cc(N4CCNCC4)cc3F)nc12] 2,6-difluoro-N-(4-isopropoxybenzo[d]thiazol-2-yl)-4-(piperazin-1-yl)benzamide | $[M + H]^+$ = 433.1 | | 7.40 |
| T057 | 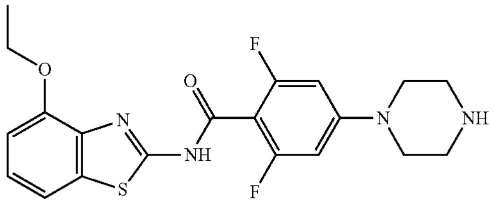 [SMILES: CCOc1cccc2sc(NC(=O)c3c(F)cc(N4CCNCC4)cc3F)nc12] N-(4-ethoxybenzo[d]thiazol-2-yl)-2,6-difluoro-4-(piperazin-1-yl)benzamide | $^1$H NMR (400 MHz, DMSO-$d_6$) δ 9.61 (s, 1H), 8.11 (s, 1H), 7.33 (s, 1H), 7.23 (d, J = 8.1 Hz, 1H), 6.79 (d, J = 12.6 Hz, 2H), 4.12 (d, J = 7.8 Hz, 2H), 3.53 (s, 4H), 3.16 (s, 4H), 1.33 (t, J = 6.9 Hz, 3H) $[M + H]^+$ = 419.1 | | 8.70 |
| T058 | 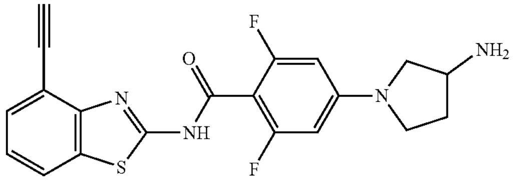 [SMILES: C#Cc1cccc2sc(NC(=O)c3c(F)cc(N4CCC(N)C4)cc3F)nc12] 4-(3-aminopyrrolidin-1-yl)-N-(4-ethynylbenzo[d]thiazol-2-yl)-2,6-difluorobenzamide | $^1$H NMR (400 MHz, DMSO-$d_6$) δ 8.15 (s, 2H), 8.08 (d, J = 7.9 Hz, 1H), 7.59 (d, J = 7.3 Hz, 1H), 7.37-7.30 (m, 1H), 6.40 (d, J = 11.8 Hz, 2H), 4.42 (s, 1H), 3.99 (s, 1H), 3.65-3.58 (m, 2H), 3.50 (dd, J = 13.1, 5.9 Hz, 2H), 2.15-2.08 (m, 1H). $[M + H]^+$ = 399.1 | 92 | 1.24 |
| T059 | 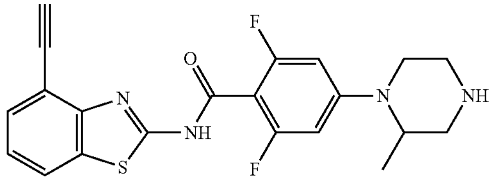 [SMILES: C#Cc1cccc2sc(NC(=O)c3c(F)cc(N4CCNCC4C)cc3F)nc12] N-(4-ethynylbenzo[d]thiazol-2-yl)-2,6-difluoro-4-(2-methylpiperazin-1-yl)benzamide | $[M + H]^+$ = 413.1 | 43 | 0.55 |

TABLE 1-continued

| Com. ID | Structure Name | $^1H$ NMR/ LCMS | Human HTRF $IC_{50}$ nM | NFκB Assay $IC_{50}$ μM |
|---|---|---|---|---|
| Compounds of benzothiazole derivatives (Formula I) and assay results | | | | |
| T060 | 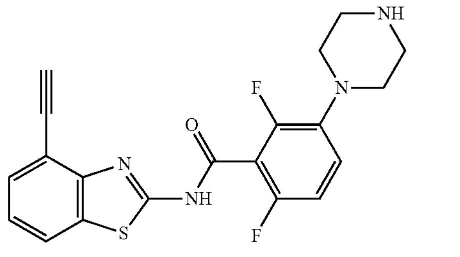 [SMILES: C#Cc1cccc2sc(NC(=O)c3c(F)ccc(N4CCNCC4)c3F)nc12] N-(4-ethynylbenzo[d]thiazol-2-yl)-2,6-difluoro-3-(piperazin-1-yl)benzamide | $[M + H]^+$ = 399.1 | 44 | 1.25 |
| T061 | 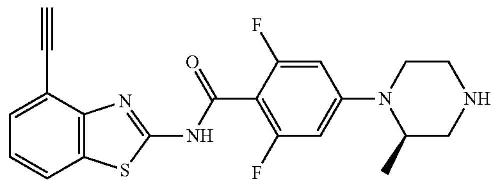 [SMILES: C#Cc1cccc2sc(NC(=O)c3c(F)cc(N4CCNC[C@H]4C)cc3F)nc12] (R)-N-(4-ethynylbenzo[d]thiazol-2-yl)-2,6-difluoro-4-(2-methylpiperazin-1-yl)benzamide | $^1H$ NMR (400 MHz, DMSO-$d_6$) δ 8.07 (d, J = 7.6 Hz, 1H), 7.58 (s, 1H), 7.33 (s, 1H), 6.70 (d, J = 13.0 Hz, 2H), 4.43 (s, 1H), 3.62-3.58 (m, 2H), 3.11-3.08 (d, J = 11.7 Hz, 2H), 3.03-2.93 (s, 4H), 2.77 (s, 1H), 1.13 (d, J = 5.2 Hz, 3H). $[M + H]^+$ = 413.1 | 30 | 0.30 |
| T062 | 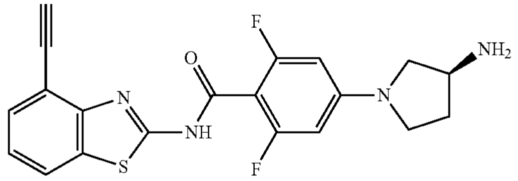 [SMILES: C#Cc1cccc2sc(NC(=O)c3c(F)cc(N4CC[C@H](N)C4)cc3F)nc12] (S)-4-(3-aminopyrrolidin-1-yl)-N-(4-ethynylbenzo[d]thiazol-2-yl)-2,6-difluorobenzamide | $^1H$ NMR (400 MHz, DMSO-$d_6$) δ 8.00 (d, J = 8.0 Hz, 1H), 7.53 (d, J = 7.3 Hz, 1H), 7.25 (d, J = 7.5 Hz, 1H), 6.23 (d, J = 12.5 Hz, 2H), 4.37 (s, 1H), 3.19 – 2.05 (m, 5H), 1.20 (s, 2H). $[M + H]^+$ = 399.1 | 89 | 0.88 |
| T063 | 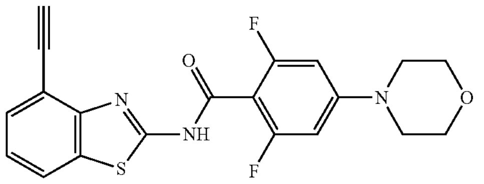 [SMILES: C#Cc1cccc2sc(NC(=O)c3c(F)cc(N4CCOCC4)cc3F)nc12] N-(4-ethynylbenzo[d]thiazol-2-yl)-2,6-difluoro-4-morpholinobenzamide | $^1H$ NMR (400 MHz, DMSO-$d_6$) δ 8.04 (d, J = 8.0 Hz, 1H), 7.56 (d, J = 8.1 Hz, 1H), 7.30 (d, J = 7.5 Hz, 1H), 6.71 (d, J = 13.2 Hz, 2H), 4.34 (s, 1H), 3.69 (s, 4H), 3.27 (s, 4H). $[M + H]^+$ = 400.0 | 165 | 1.28 |
| T064 | 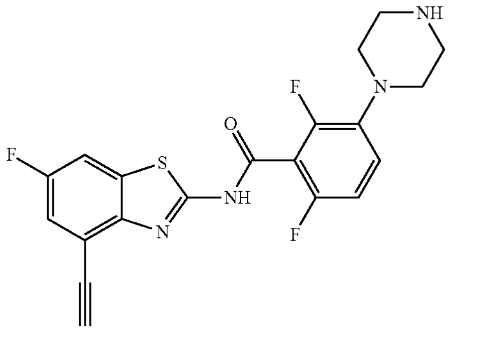 [SMILES: C#Cc1cc(F)cc2sc(NC(=O)c3c(F)ccc(N4CCNCC4)c3F)nc12] | [M + H]+ = 417 | 51 | 1.03 |

TABLE 1-continued

| Compounds of benzothiazole derivatives (Formula I) and assay results | | | | |
|---|---|---|---|---|
| Com. ID | Structure Name | $^{1}$H NMR/ LCMS | Human HTRF $IC_{50}$ nM | NFκB Assay $IC_{50}$ μM |
| | N-(4-ethynyl-6-fluorobenzo[d]thiazol-2-yl)-2,6-difluoro-3-(piperazin-1-yl)benzamide | | | |
| T065 | 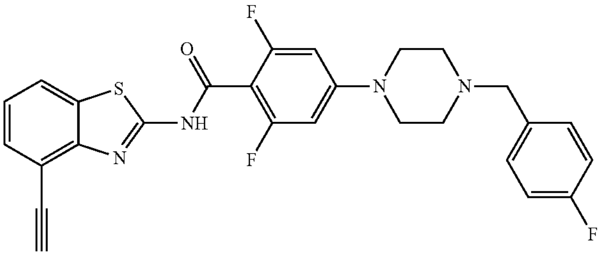 [SMILES: C#Cc1cccc2sc(NC(=O)c3c(F)cc(N4CCN(Cc5ccc(F)cc5)CC4)cc3F)nc12] N-(4-ethynylbenzo[d]thiazol-2-yl)-2,6-difluoro-4-(4-(4-fluorobenzyl)piperazin-1-yl)benzamide | [M + H]+ = 507.1 | 182 | 6.58 |
| T066 | 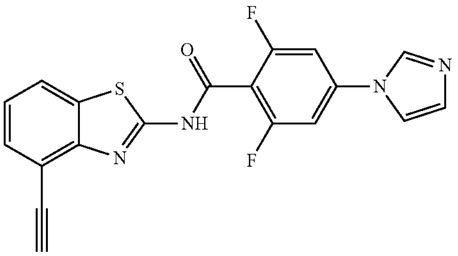 [SMILES: C#Cc1cccc2sc(NC(=O)c3c(F)cc(-n4ccnc4)cc3F)nc12] N-(4-ethynylbenzo[d]thiazol-2-yl)-2,6-difluoro-4-(1H-imidazol-1-yl)benzamide | [M + H]+ = 381.0 | 367 | 1.56 |

TABLE 2

| Compound of quinoline derivatives (Formula II) and assay results | | | | |
|---|---|---|---|---|
| Com. ID | Structure Name | $^{1}$H NMR LCMS | Human HTRF $IC_{50}$ nM | NFκB Assay $IC_{50}$ μM |
| Q001 | 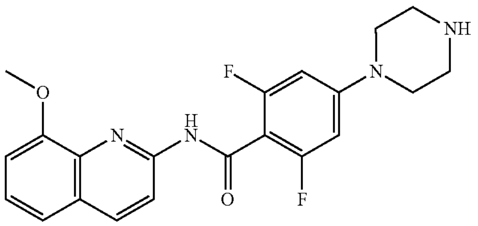 [SMILES: COc1cccc2ccc(NC(=O)c3c(F)cc(N4CCNCC4)cc3F)nc12] 2,6-difluoro-N-(8-methoxyquinolin-2-yl)-4-(piperazin-1-yl)benzamide | (400 MHz, DMSO-$d_6$) δ 11.83 (s, 1H), 9.51 (s, 1H), 8.45 (d, 1H), 8.26 (d, 1H), 7.48 (m, 2H), 7.24 (d, 1H), 6.77 (d, 2H), 3.94 (s, 3H), 3.57 (m, 4H), 3.14 (m, 4H). $[M + H]^+ = 399$ | 45 | 1.24 |
| Q002 | 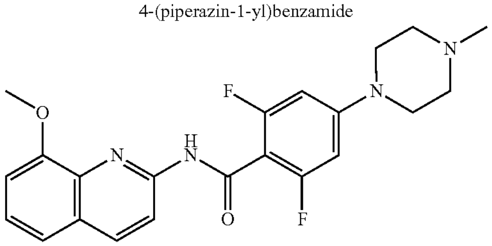 | —/ $[M + H]^+ = 413$ | 157 | 2.30 |

TABLE 2-continued

| Compound of quinoline derivatives (Formula II) and assay results | | | | |
|---|---|---|---|---|
| Com. ID | Structure Name | $^1$H NMR LCMS | Human HTRF $IC_{50}$ nM | NFκB Assay $IC_{50}$ μM |
| | 2,6-difluoro-N-(8-methoxyquinolin-2-yl)-4-(4-methylpiperazin-1-yl)benzamide | | | |
| Q003 | 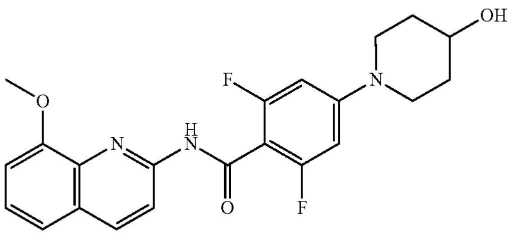 [SMILES: COc1cccc2ccc(NC(=O)c3c(F)cc(N4CCC(O)CC4)cc3F)nc12]<br>2,6-difluoro-4-(4-hydroxypiperidin-1-yl)-N-(8-methoxyquinolin-2-yl)benzamide | —/<br>[M + H]$^+$ = 414 | 369 | 2.97 |
| Q004 | 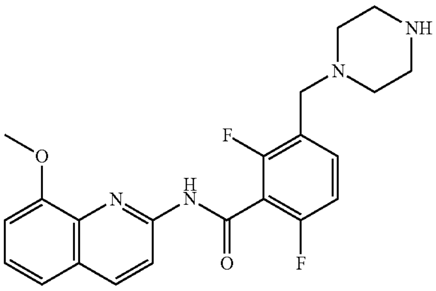 [SMILES: COc1cccc2ccc(NC(=O)c3c(F)ccc(CN4CCNCC4)c3F)nc12]<br>2,6-difluoro-N-(8-methoxyquinolin-2-yl)-3-(piperazin-1-ylmethyl)benzamide | —/<br>[M + H]$^+$ = 413 | 33 | 4.30 |
| Q005 | 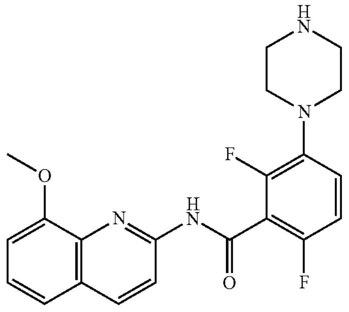 [SMILES: COc1cccc2ccc(NC(=O)c3c(F)ccc(N4CCNCC4)c3F)nc12]<br>2,6-difluoro-N-(8-methoxyquinolin-2-yl)-3-(piperazin-1-yl)benzamide | (400 MHz, Methanol-$d_4$) δ 8.87 (d, J = 9.0 Hz, 1H), 7.87-7.69 (m, 3H), 7.58 (dd, J = 1.3, 7.3 Hz, 1H), 7.43 (dt, J = 5.5, 9.3 Hz, 1H), 7.19 (dt, J = 1.7, 9.0 Hz, 1H), 4.21 (s, 3H), 3.40 (br dd, J = 6.1, 17.1 Hz, 8H)/<br>[M + H]$^+$ = 399.1 | 258 | 1.37 |
| Q006 | 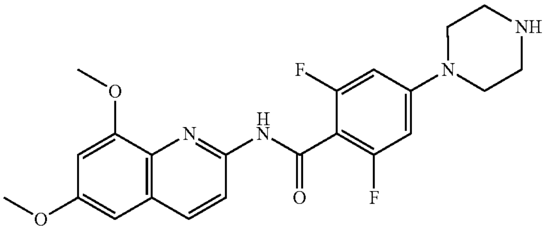 [SMILES: COc1cc(OC)c2nc(NC(=O)c3c(F)cc(N4CCNCC4)cc3F)ccc2c1]<br>N-(6,8-dimethoxyquinolin-2-yl)-2,6-difluoro-4-(piperazin-1-yl)benzamide | (400 MHz, DMSO-$d_6$) δ 11.38 (s, 1H), 9.11 (br s, 2H), 8.30-8.22 (m, 2H), 6.92 (d, J = 2.5 Hz, 1H), 6.82 (d, J = 2.5 Hz, 1H), 6.80 (s, 1H), 6.77 (s, 1H), 3.91 (s, 3H), 3.87 (s, 3H), 3.56 – 3.52 (m, 4H), 3.20 (br s, 4H)/<br>[M + H]$^+$ = 429 | 606 | 11.10 |

TABLE 2-continued

Compound of quinoline derivatives (Formula II) and assay results

| Com. ID | Structure Name | $^1$H NMR LCMS | Human HTRF $IC_{50}$ nM | NFκB Assay $IC_{50}$ μM |
|---|---|---|---|---|
| Q007 | 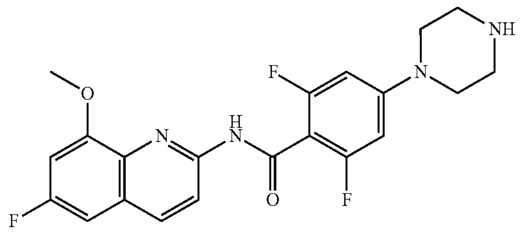 [SMILES: COc1cc(F)cc2ccc(NC(=O)c3c(F)cc(N4CCNCC4)cc3F)nc12] 2,6-difluoro-N-(6-fluoro-8-methoxyquinolin-2-yl)-4-(piperazin-1-yl)benzamide | (400 MHz, DMSO-$d_6$) δ 11.52 (s, 1H), 9.36 (br s, 2H), 8.36 (s, 2H), 7.35-7.23 (m, 1H), 7.16 (dd, J = 2.6, 11.2 Hz, 1H), 6.78 (br d, J = 11.7 Hz, 2H), 3.97 (s, 3H), 3.63-3.52 (m, 4H), 3.18 (br s, 4H)/ $[M + H]^+$ = 417 | 176 | 6.78 |
| Q008 | 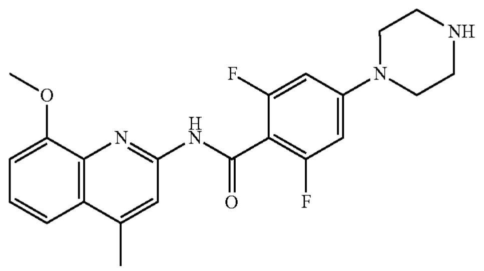 [SMILES: COc1cccc2c(C)cc(NC(=O)c3c(F)cc(N4CCNCC4)cc3F)nc12] 2,6-difluoro-N-(8-methoxy-4-methylquinolin-2-yl)-4-(piperazin-1-yl)benzamide | (400 MHz, Methonal-$d_4$) δ 7.86-7.85 (m, 1H), 7.81-7.77 (m, 1H), 7.62-7.60 (m, 1H), 7.51(s, 1H), 6.85 - 6.82 (m, 2H), 4.23 (s, 3H), 3.72-3.70 (m, 4H), 3.40-3.38 (m, 4H), 2.92 (s, 3H)/ $[M + H]^+$ = 413.1 | 149 | 2.92 |
| Q009 | 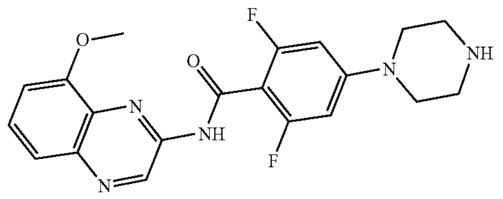 [SMILES: COc1cccc2ncc(NC(=O)c3c(F)cc(N4CCNCC4)cc3F)nc12] 2,6-difluoro-N-(8-methoxyquinoxalin-2-yl)-4-(piperazin-1-yl)benzamide | (400 MHz, Methonal-$d_4$) δ 9.74 (s, 1H), 7.70 - 7.61 (m, 2H), 7.26 - 7.24 (m, 1H), 6.66 - 6.64 (m, 2H), 4.05 (s, 3H), 3.60-3.57 (m, 4H), 3.38-3.35(m, 4H)/ $[M + H]^+$ = 400.1 | 178 | 3.72 |

Methods of Use

ALPK1 is an intracytoplasmic serine threonine protein kinase that plays an important role in activating the innate immune response. ALPK1 binds to the bacterial pathogen-associated molecular pattern metabolite (PAMP), ADP-D-glycero-beta-D-manno-heptose (ADP-heptose). ALPK1-ADP-heptose binding occurs through direct interaction at the ALPK1 N-terminal domain. This interaction stimulates the kinase activity of ALPK1 and its phosphorylation and activation of TRAF-interacting protein with forkhead-associated domain (TIFA). In turn, TIFA activation triggers proinflammatory NFkB signaling, including proinflammatory cytokine and chemokine expression and/or secretion. Accordingly, the compounds disclosed herein are generally useful as inhibitors of ALPK1 kinase activity and downstream activation of NFkB proinflammatory signaling.

The disclosure provides for the use of a compound of Formula (I) or (II), or a subembodiment thereof as described herein, for inhibiting ALPK1 kinase activity and reducing inflammation in a target tissue. The methods also encompass the use of a compound of Formula (I) or (II), or a subembodiment thereof as described herein, for treating a disease, disorder, or condition characterized by excessive or inappropriate ALPK1-dependent proinflammatory signaling. In embodiments, the disease, disorder, or condition is selected from systemic lupus erythematosus (SLE), sepsis, a cancer, spiroandenoma, spiroandenocarcinoma, "Retinal dystrophy, Optic nerve edema, Splenomegaly, Anhidrosis and migraine Headache" ("ROSAH") syndrome, and "Periodic Fever, Aphthous Stomatitis, Pharyngitis, and Adenitis" ("PFAPA") syndrome. In embodiments, the cancer is selected from lung cancer, colon cancer, and oral squamous cancer. In embodiments, the cancer is oral squamous cancer.

In embodiments, the disclosure provides methods for inhibiting ALPK1 kinase activity in a mammalian cell or target tissue by contacting the cell or target tissue with a compound of Formula (I) or (II), or a subembodiment described herein. In embodiments, the methods comprise administering a pharmaceutical composition comprising a compound of Formula (I) or (II), or a subembodiment described herein, to a subject in an amount effective to inhibit ALPK1 kinase activity in a target cell or tissue of the subject. In embodiments, the methods comprise reducing inflammation in a target tissue of a subject in need of such therapy by administering to the subject a compound of Formula (I) or (II), or a subembodiment described herein, or a pharmaceutical composition comprising same.

In embodiments, the disclosure provides methods of treating a subject having a disease or disorder characterized by excessive or inappropriate activation of ALPK1 kinase activity, the methods comprising administering to the subject a compound of Formula (I) or (II), or a subembodiment described herein. In embodiments, the disease or disorder is selected from systemic lupus erythematosus (SLE), sepsis, cancer, spiroandenoma, spiroandenocarcinoma, ROSAH syndrome, and PFAPA syndrome.

In embodiments, the disease or disorder is spiradenoma or spiroandenocarcinoma, and the methods comprise administering a compound of Formula (I) or (II), or a subembodiment described herein, to a subject in need of such treatment. In embodiments, the subject in need of treatment is one diagnosed with spiradenoma or spiroandenocarcinoma and carrying one or more genetic mutations in ALPK1. In embodiments, at least one of the genetic mutations is an activating mutation. In embodiments, the genetic mutation in ALPK1 is p.V1092A, as described in Rashid et al., *Nature Communications* (2019).

In embodiments, the disease or disorder is ROSAH, and the methods comprise administering a compound of Formula (I) or (II), or a subembodiment described herein, to a subject in need of such treatment. In embodiments, the subject in need of treatment is one diagnosed with ROSAH and carrying one or more genetic mutations in ALPK1. In embodiments, at least one of the genetic mutations is an activating mutation. In embodiments, the genetic mutation in the ALPK1 gene is c.710C>T, p.T237M, as described in Williams et al., *Genetics in Medicine* 21:2103-2115 (2019).

In embodiments, the disease or disorder is PFAPA, and the methods comprise administering a compound of Formula (I) or (II), or a subembodiment described herein, to a subject in need of such treatment. In embodiments, the subject in need of treatment is one diagnosed with or having clinical symptoms of PFAPA and carrying one or more genetic mutations in ALPK1. In embodiments, at least one of the genetic mutations is an activating mutation. In embodiments, the genetic mutation in the ALPK1 gene is 2770T>C, p.(S924P), as described in Sangiorgi et al. *Eur. J. Human Genetics* (2019).

In embodiments, the disease or disorder is a cancer selected from lung cancer, colon cancer, and oral squamous cancer. In embodiments, the cancer is oral squamous cancer. In embodiments, the subject in need of treatment is one diagnosed with a cancer, wherein the cancer cells carry at least one activating mutation in ALPK1, or wherein the cancer cells express ALPK1 mRNA or protein at elevated levels compared to non-cancer cells of the subject.

In embodiments, the disclosure further provides methods of identifying a disease, disorder, or condition for treatment with a compound of Formula (I) or (II), or a subembodiment described herein, the methods comprising assaying a biological sample from a subject diagnosed with the disease, disorder, or condition for one or more of an activating mutation in ALPK1, and overexpression of ALPK1 mRNA or protein in cells or tissues involved in the disease, disorder, or condition, as compared to cells or tissues of a reference not involved in the disease, disorder, or condition. In embodiments, the activating mutation in ALPK1 is 2770T>C, p.(S924P).

In the context of the methods described here, the term "treating" may refer to the amelioration or stabilization of one or more symptoms associated with the disease, disorder or condition being treated. The term "treating" may also encompass the management of disease, disorder or condition, referring to the beneficial effects that a subject derives from a therapy but which does not result in a cure of the underlying disease, disorder, or condition.

In embodiments where a therapeutically effective amount of a composition is administered to a subject, the therapeutically effective amount is the amount sufficient to achieve a desired therapeutic outcome, for example the amelioration or stabilization of one or more symptoms of the disease, disorder or condition being treated, or in the context of prevention, the amount sufficient to achieve prevention of the recurrence, development, progression or onset of one or more symptoms of the disease, disorder, or condition.

In embodiments, a therapeutically effective amount is the amount required to achieve at least an equivalent therapeutic effect compared to a standard therapy. An example of a standard therapy is an FDA-approved drug indicated for treating the same disease, disorder or condition.

In the context of any of the methods described here, the subject is preferably a human but may be a non-human mammal, preferably a non-human primate. In other embodiments, the non-human mammal may be, for example, a dog, cat, a rodent (e.g., a mouse, a rat, a rabbit), a horse, a cow, a sheep, a goat, or any other non-human mammal.

In embodiments, the human subject is selected from an adult human, a pediatric human, or a geriatric human, as those terms are understood by the medical practitioner, for example as defined by the U.S. Food and Drug Administration.

Pharmaceutical Compositions

In embodiments, the disclosure also provides a pharmaceutical composition comprising a compound of Formula (I) or (II), or a subembodiment described herein, and a carrier or excipient, for use in the methods described herein. In embodiments, the pharmaceutical composition is formulated for delivery by an oral or rectal route. In embodiments, the pharmaceutical composition is formulated as an oral dosage form in the form of a tablet or capsule. In embodiments, the pharmaceutical composition is formulated as a rectal dosage form in the form of an ointment, suppository, or enema. In embodiments, the pharmaceutical composition is formulated as a parenteral dosage form. In embodiments, the parenteral dosage form is suitable for administration by an intravenous, intra-arterial, or intramuscular route, e.g., by injection of an aqueous liquid.

In embodiments, the disclosure provides a composition comprising a compound of Formula (I) or (II), or a subembodiment described herein, and one or more excipients or carriers, preferably pharmaceutically acceptable excipients or carriers. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Excipients for preparing a pharmaceutical composition are generally those that are known to be safe and non-toxic when administered to a human or animal body. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, and suitable mixtures of any of the foregoing. The particular excipients utilized in a composition will depend upon various factors, including chemical stability and solubility of the compound being formulated and the intended route of administration.

A pharmaceutical composition can be provided in bulk or unit dosage form. It is especially advantageous to formulate pharmaceutical compositions in unit dosage form for ease of administration and uniformity of dosage. The term "unit dosage form" refers to physically discrete units suited as unitary dosages for the subject to be treated; each unit containing a predetermined quantity of an active compound calculated to produce the desired therapeutic effect in association with the required pharmaceutical carrier. A unit dosage form can be an ampoule, a vial, a suppository, a dragee, a tablet, a capsule, an IV bag, or a single pump on an aerosol inhaler.

In therapeutic applications, dose may vary depending on the chemical and physical properties of the active compound as well as clinical characteristics of the subject, including e.g., age, weight, and co-morbidities. Generally, the dose should be a therapeutically effective amount. An effective amount of a pharmaceutical composition is that which provides an objectively identifiable improvement as noted by the clinician or other qualified observer. For example, alleviating a symptom of a disorder, disease or condition.

A pharmaceutical compositions may take any suitable form (e.g. liquids, aerosols, solutions, inhalants, mists, sprays; or solids, powders, ointments, pastes, creams, lotions, gels, patches and the like) for administration by any desired route (e.g. pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). In embodiments, the pharmaceutical composition is in the form of an orally acceptable dosage form including, but not limited to, capsules, tablets, buccal forms, troches, lozenges, and oral liquids in the form of emulsions, aqueous suspensions, dispersions or solutions. Capsules may contain excipients such as inert fillers and/or diluents including starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added.

In embodiments, the pharmaceutical composition is in the form of a tablet. The tablet can comprise a unit dose of a compound described here together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. butylated hydroxytoluene), buffering agents (e.g. phosphate or citrate buffers), and effervescent agents such as citrate/bicarbonate mixtures. The tablet may be a coated tablet. The coating can be a protective film coating (e.g. a wax or varnish) or a coating designed to control the release of the active compound, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecyl sulfate, magnesium aluminum silicate, and triethanolamine.

In embodiments, the pharmaceutical composition is in the form of a hard or soft gelatin capsule. In accordance with this formulation, the compound of the present disclosure may be in a solid, semi-solid, or liquid form.

In embodiments, the pharmaceutical composition is in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

In embodiments, the pharmaceutical composition is in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions can be prepared in water with the aid of co-solvent or a surfactant. Examples of suitable surfactants include polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides. Dispersions can also be prepared, for example, in glycerol, liquid polyethylene glycols and mixtures of the same in oils.

The present disclosure also provides packaging and kits comprising pharmaceutical compositions for use in the methods described here. The kit can comprise one or more containers selected from the group consisting of a bottle, a vial, an ampoule, a blister pack, and a syringe. The kit can further include one or more of instructions for use, one or more syringes, one or more applicators, or a sterile solution suitable for reconstituting a compound or composition described here.

All percentages and ratios used herein, unless otherwise indicated, are by weight.

The invention is further described and exemplified by the following non-limiting examples.

EXAMPLES

In embodiments, a compound of Formula (I) or (II), or a subembodiment described herein, is an inhibitor of ALPK1 as measured, for example, in an in vitro ALPK1 kinase assay, or an assay designed to measure ALPK1 pathway activation, for example NFkB transcriptional activation or IL-8 secretion. In general, the computer program XL fit was used for data analysis, including non-linear regression analysis. The half maximal inhibitory concentration (IC50) was used as the measure of a compound's effectiveness in the assays. IC50 values were determined using following logistic equation $Y=min+(max-min)/(1+(X/IC_{50}\hat{}-hill\text{-}slope)$, where Y is the value at the compound concentration, X. The concentration response curve fitting was conducted using GraphPad Prism version 6.00 software.

Biological Assays and Data

In embodiments, a compound of Formula (I) or (II) is an inhibitor of ALPK1 as measured, for example, in an in vitro ALPK1 kinase assay, or an assay designed to measure ALPK1 kinase activity indirectly, such as through ALPK1 pathway activation by assaying for downstream targets in the pathway, for example, NFkB transcriptional activation or IL-8 secretion. In general, the computer program XL fit was used for data analysis, including non-linear regression analysis. The half maximal inhibitory concentration (IC50) was used as the measure of a compound's effectiveness in the assays. IC50 values were determined using following logistic equation Y=min+(max−min)/(1+(X/IC50^-hill-slope), where Y is the value at the compound concentration, X. The concentration response curve fitting was conducted using GraphPad Prism version 6.00 software.

ALPK1 In Vitro Kinase Assay

ALPK1 kinase activity was measured in an in vitro assay using ADP-Heptose as the ALPK1 ligand and activator of its kinase activity and TIFA protein as the ALPK1 phosphorylation substrate. Since phosphorylated TIFA proteins oligomerize, Homogeneous Time-Resolved Fluorescence (HTRF) was used to measure protein:protein interaction between HA-tagged TIFA proteins as an indicator of TIFA phosphorylation.

In brief, dose-response studies were performed with HEK293 cells cultured in Dulbecco's Modified Eagle Medium (DMEM) supplemented 10% fetal bovine serum (FBS, Hyclone™) containing antibiotics (pen/strep, G418) in 384-well assay plates. Each well contained 0.1 mg TIFA, ALPK1 (2 nM final concentration in reaction mixture) and kinase buffer (100 mM of HEPES pH 7.4, 4 mM DTT, 40 mM $MgCl_2$, 20 mM of β-Glycerol phosphate disodium salt, 0.4 mM of $Na_3VO_4$, 0.16 mg/mL). Titrations of the test compounds were prepared in dimethylsulphoxide (DMSO). The reaction was initiated by addition of ATP and ADP-Heptose.

For HTRF, samples were incubated with a Tb cryptate-labeled anti-HA antibody for capturing HA-tagged proteins according to the manufacturer's instructions (PerkinElmer™, CisBio™) and the fluorescence signal was quantified (Tecan Infinite F NANO+). HTRF signals were calculated as the HTRF ratio (ratio of fluorescence measured at 665 nm and 620 nm)×104 (thereby using the signal at 620 nm as an internal standard).

All compounds exhibited a dose-dependent decrease in TIFA phosphorylation in this assay. IC50 values were determined using 3- or 4-parameter logistic equation using GraphPad Prism version 6.00. The reference compound, A027, was used as a positive control for each plate. This compound has an IC50 of ~50 nanomolar (nM) in this assay. IC50 values for the test compounds ranged from 1 to 2000 nM and are shown in Table 1 (Formula I compounds) and Table 2 (Formula II compounds).

NFκB Gene Reporter Alkaline Phosphatase Assay

An alkaline phosphatase reporter assay system was used to measure inhibition of ALPK1-dependent NFκB reporter gene activation. Briefly, HEK293 cells stably expressing an NF-kB reporter (referred to herein as "G9 cells") were maintained in DMEM as described above. For the assay, cells were seeded into 96-well plates at a density of 10,000 cells/well in Freestyle™ 293 Expression Medium (ThermoFisher), and allowed to attach overnight. Cells were pretreated with serially diluted compounds for 30 min and then stimulated with D-glycero-D-manno-6-fluoro-heptose-1β-S-ADP. This compound is an analog of ADP-heptose that shows increased stability in vitro along with a similar ability to activate ALPK1 kinase activity. NFkB gene activation was detected using the chromogenic substrate, para-nitrophenyl phosphate (pNPP) according to the manufacturer's protocols (pNPP Phosphatase Assay, Beyotime Biotechnology). All compounds exhibited a dose-dependent decrease in NFkB promoter-driven gene expression in this assay. IC50 values ranged from 0.5-15 micromolar (uM) and are shown in Table 1 (Formula I compounds) and Table 2 (Formula II compounds).

Inhibition of Activated ALPK1

Activating mutations in ALPK1 are associated with diseases and disorders such as cancer, spiroandenoma, spiroandenocarcinoma, ROSAH syndrome, and PFAPA syndrome. We conducted further experiments to evaluate the ability of representative compounds to inhibit ALPK1 in the context of two activating mutations, T237M and V1092A. In preliminary experiments we determined that IL-8 protein secretion was elevated in cells transiently transfected with human ALPK1 expression vectors containing each of these activating mutations. Accordingly, we used IL-8 secretion as an indicator of activated ALPK1 inhibition in cells expressing these mutations.

First, in preliminary experiments, we established that IL-8 secretion was significantly increased in cells transiently expressing either of the two activating mutations, T237M or V1092A. HEK293 cells were cultured as described above prior to transient transfection with either empty vector or an expression vector encoding (i) human ALPK1 (hALPK1), (ii) hALPK1 with the T237M activating mutation (hALPK1-T237M) (iii) hALPK1 with the V1092A activating mutation (hALPK1-V1092A), or (iv) a kinase dead ALPK1 mutant (hALPK1-T237M-D1194S). Transfection was performed according to manufacturer's protocols (Lipofectamine™ 3000, ThermoFisher). Transfected cells were selected, seeded onto 96-well plates and treated with serial dilutions of the test compounds for 6.5 hr. Following treatment, cell viability was determined using a luminescent cell viability assay (Cell Counting-Lite Assay or "CCL Assay" from Vazyme Biotech Co., Ltd.) and cell free supernatants were collected and analyzed for IL-8 protein by IL-8 ELISA as described above. FIG. 1 shows IL-8 secretion for each of the test groups. As shown in the figure, very little IL-8 was detectable in cells transfected with any of the empty vector, hALPK1, or the kinase dead hALPK1 mutant. In contrast, both of the activating mutations in hALPK1 induced significant IL-8 secretion.

Next, we tested a representative set of compounds for inhibition of IL-8 secretion in cells expressing each of the activating ALPK1 mutants, T237M and V1092A. Table 3 shows inhibition of IL-8 secretion in cells transfected with the T237M and Table 4 shows inhibition of IL-8 secretion in cells transfected with the V1092A mutant. For the T237M mutant study, we produced an HEK293 cell line ("A2") stably expressing the T237M hALPK1 mutant. A2 cells were cultured in the presence of test compound for 40 hours total. Fresh medium and compound were added at 24 hours. Cell viability and IL-8 secretion were determined 16 hours after the second addition of compound, using the CCL assay and IL-8 ELISA as described above. Table 3 shows half maximal inhibitory concentration (IC50) of IL-8 secretion in A2 cells, relative to IL-8 secretion from wild-type HEK293 cells, such that knockdown to the level of IL-8 from wild-type cells was considered to be 100% inhibition.

TABLE 3

Half maximal inhibitory concentration (IC50) of IL-8 secretion in cells expressing T237M mutant

| Compd. ID | IC50 (uM) |
|---|---|
| T007 | 0.06831 |
| T017 | 1.474 |
| T019 | 0.6676 |
| T047 | 0.6349 |
| T054 | 0.2254 |
| T060 | 2.1400 |
| T064 | 1.6890 |

For the V1092A mutant study shown in Table 4, HEK293 cells were transiently transfected with hALPK1-V1092A or hALPK1 (wildtype) expression vectors and then treated with test compounds for 24 hours. Fresh medium and compound were added at 18 hours. Cell viability and IL-8 secretion were determined 6 hours after the second addition of compound, using the CCL assay and IL-8 ELISA as described above. the table 4 shows half maximal inhibitory concentration (IC50) of IL-8 secretion relative to wild-type HEK293 cells.

TABLE 4

Half maximal inhibitory concentration (IC50) of IL-8 secretion in cells expressing V1092A mutant

| Compd. ID | IC50 (uM) |
|---|---|
| T007 | 0.4093 |
| T017 | 5.034 |
| T019 | 3.167 |
| T047 | 1.806 |
| T054 | 0.226 |
| T060 | 5.385 |

Efficacy Study in SLE Animal Model

Figure 2:
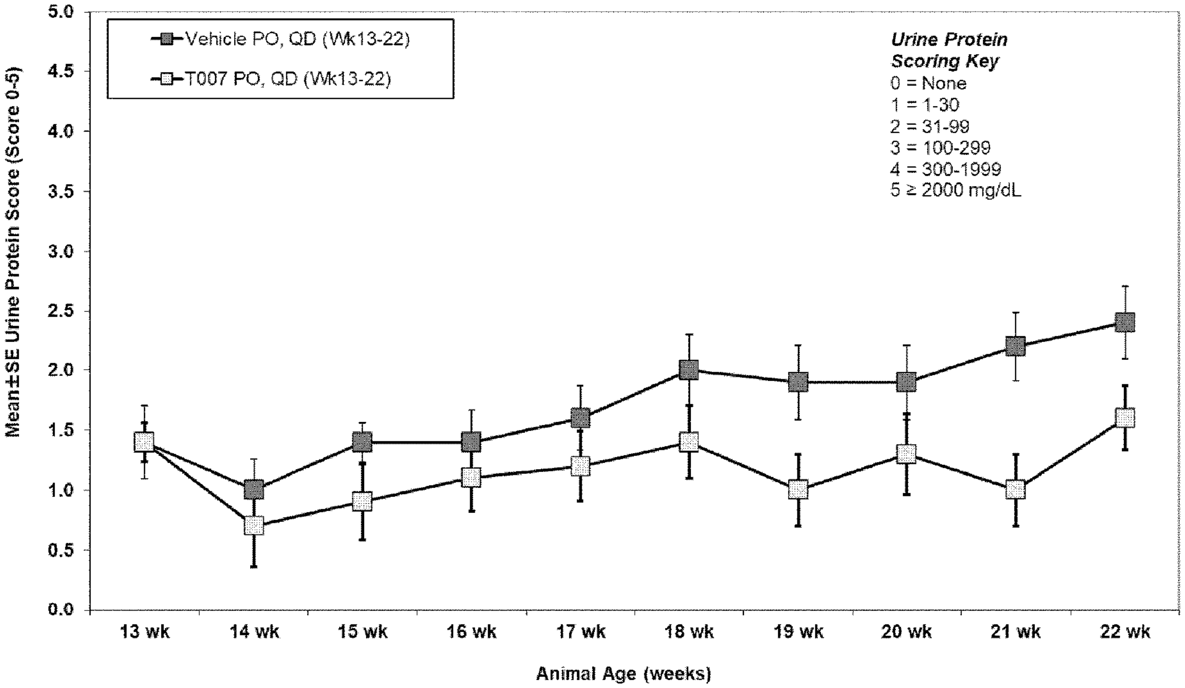
FIG. 2: In the lupus animal model, PO treatment with T007 (50 mg/kg) administered QD from mouse age 13 to 22 weeks showed statistically significant beneficial effects on SLE in female MRL/MpJ-faslpr/J mice as determined by evaluation of proteinuria, serum anti-dsDNA antibody levels, and kidney histopathology. Urine protein scores were significantly (55%) reduced at mouse age 21 weeks in mice treated with T007 as compared to the vehicle disease control group (34% reduction in AUC, p=0.100).
Figure 3A:
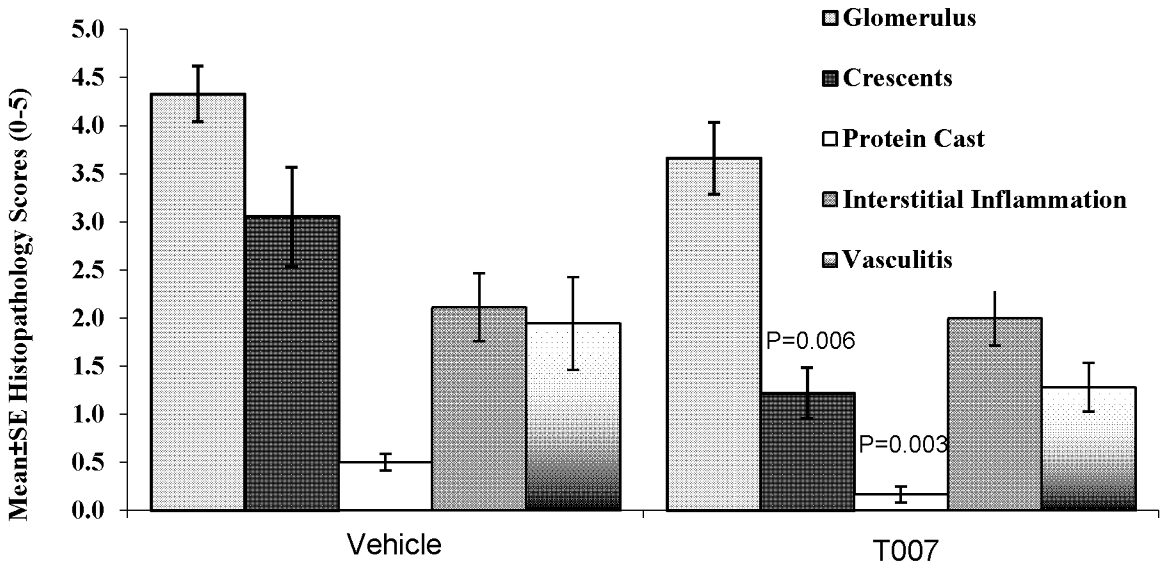
FIG. 3A: In the lupus animal model, the evaluation of kidney histopathology (right kidneys) showed that treatment with T007 significantly reduced glomerulus diameters (38% reduction), crescent scores (62%), protein cast scores (70%).
Figure 3B:
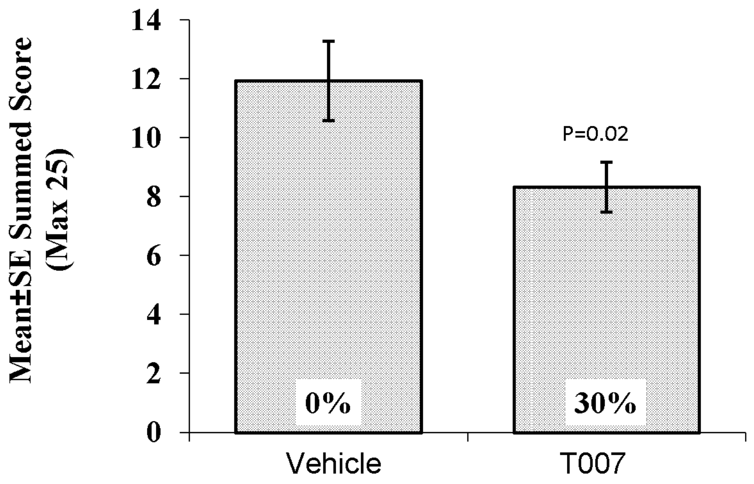
FIG. 3B: In the lupus animal model, summed kidney scores (34%) as compared to the vehicle disease control group.

A mouse model of systemic lupus erythematosus (SLE) was used to evaluate the ability of ALPK1 inhibitors to treat this condition. Female MRL/MpJ-faslpr/J mice were treated with test compound (T007) for 9 weeks. At about 13 weeks of age (study day 0), female mice were randomized into two treatment groups of 10 mice per group, and daily (QD) oral (PO) treatment with vehicle (5% PEG400, 95% methylcellulose [MC]) or the test compound, T007 (50 mg/kg) was initiated. The animals were euthanized for necropsy and tissue collection at age 22 weeks. As shown in FIG. 2, T007 showed statistically significant beneficial effects on SLE as determined by evaluation of proteinuria, serum anti-dsDNA antibody levels, and kidney histopathology. Urine protein scores were significantly (55%) reduced at age 21 weeks in the treatment group compared to the untreated (vehicle) group (34% reduction in AUC, p=0.100). As shown in FIG. 3A, kidney histopathology (right kidneys) indicated that treatment with T007 significantly reduced glomerulus diameters (38% reduction), crescent scores (62%), protein cast scores (70%). FIG. 3B shows the summed kidney scores (34%) in the treatment group compared to the untreated (vehicle) group.

Efficacy Study in Sepsis Induced Acute Kidney Injury Animal Model

Figure 4:
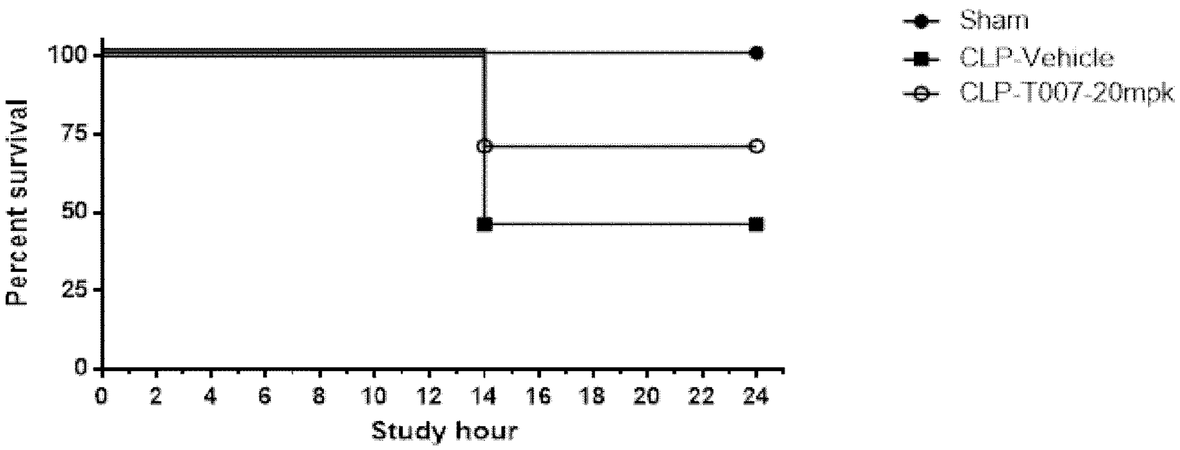
FIG. 4: In the sepsis induced acute kidney injury animal model, the compound T007 (20 mg/kg) was given 2 hours prior to the surgery. 24 hours post-surgery, survival proportion was recorded over the following 24 hours. The data show that the ALPK1 inhibitor improved the survival rate of the animals.
Figure 5:
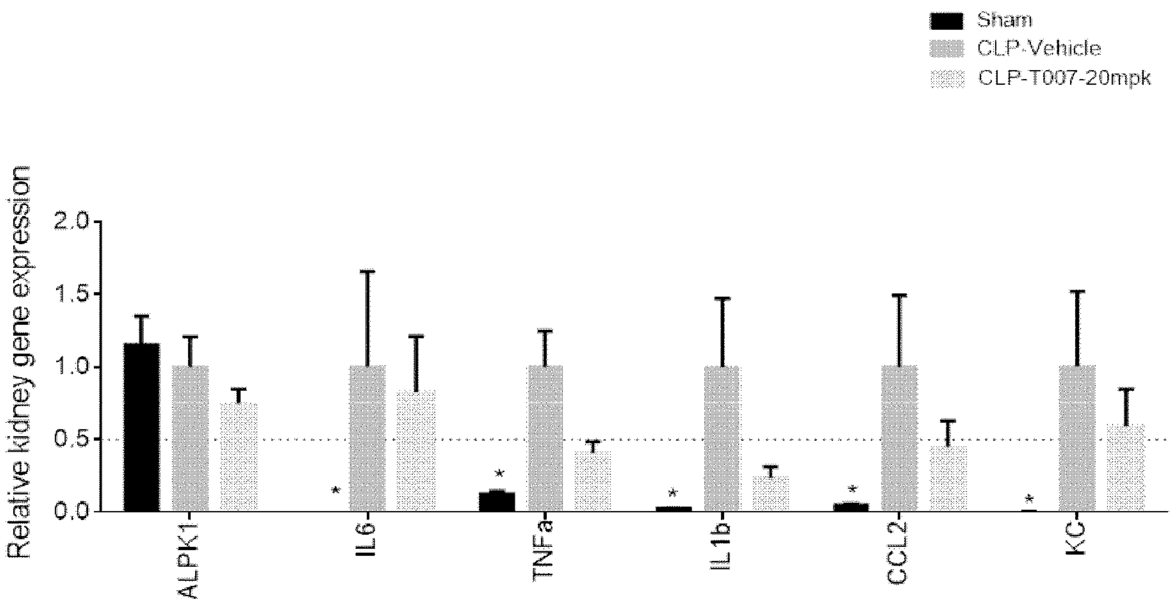
FIG. 5: In the sepsis induced acute kidney injury animal model, at 24 hours post-surgery, the kidneys were collected for gene expression analysis by Q-PCR. The results show that the ALPK1 inhibitorT007 inhibited kidney proinflammatory gene expression, including IL6, TNFa, IL-1b, CCl2 and Keratinocyte chemoattractant (KC) chemokine. $*p<0.05$, vs. CLP-Vehicle
Figure 6:
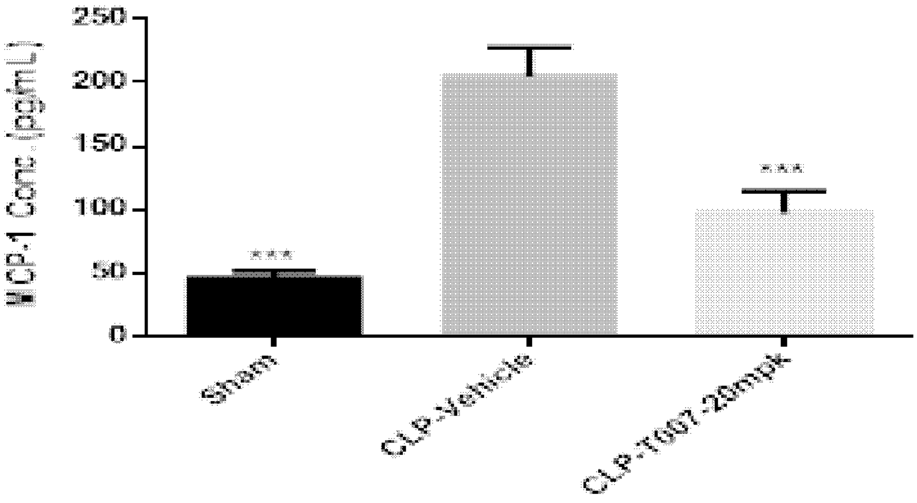
FIG. 6: In the sepsis induced acute kidney injury animal model, the compound T007 (20 mg/kg) was given 2 hours prior to the surgery. And 24 hours post-surgery, plasma MCP-1 concentration was measured by ELISA. The results show that the ALPK1 inhibitor improved plasma MCP-1 levels. $***p<0.001$ vs. CLP-Vehicle by one-way ANOVA

Polymicrobial sepsis induced by cecal ligation and puncture (CLP) is the most frequently used model because it closely resembles the progression and characteristics of human sepsis. We used this model system to evaluate the effects of the compound T007 in sepsis. Briefly, the SD rat cecum was ligated with sterile silk thread, and then cecum was punctured twice with a needle, gently squeezed to express a small amount of fecal material, then the abdominal incision was closed. The test compound, T007 (20 mg/kg) was administered 2 hours prior to the surgery. 24 hours post-surgery, survival was recorded, plasma was collected for MCP-1 analysis, and kidneys were collected for gene expression analysis by Q-PCR. FIG. 4 shows that the test compound improved the survival rate of the mice. FIG. 5 shows that the test compound inhibited kidney proinflammatory gene expression. Specifically, inhibition of gene expression was observed for IL6, TNFa, IL-1b, CCl2 and KC. FIG. 6 shows that plasma MCP-1 plasma concentrations as measured by ELISA were also improved in the treatment group.

EQUIVALENTS

Those skilled in the art will recognize or be able to ascertain using no more than routine experimentation, many equivalents to the specific embodiments of the invention as described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A compound having a structure of:

(I)

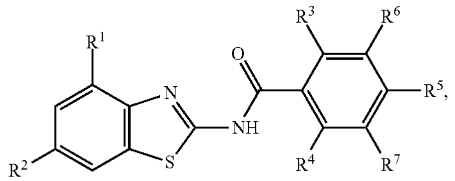

wherein:

$R^1$ is hydrogen, halogen, —C≡CH, —C≡CH—$CH_3$, —$CX_3$, —$CHX_2$, —$CH_2X$, —$OCX_3$, —$OCH_2X$, —$OCHX_2$, —$OR^{1A}$, substituted or unsubstituted $C_1$-$C_6$ alkyl, substituted or unsubstituted 2 to 6 membered heteroalkyl, or substituted or unsubstituted $C_3$-$C_6$ cycloalkyl;

$R^2$ is hydrogen or halogen;

Each $R^3$ and $R^4$ is independently halogen, —$OR^{3A}$, or unsubstituted $C_1$-$C_6$ alkyl;

$R^5$ is —$NR^{5B}R^{5C}$, —$(CH_2)_{n5}NR^{5B}R^{5C}$, —C(O)$NR^{5B}R^{5C}$, —$O(CH_2)_{m5}OR^{5A}$, substituted or unsubstituted 5 to 6 membered heterocycloalkyl or substituted or unsubstituted $C_6$-$C_{12}$ aryl; $R^6$ and $R^7$ are hydrogen;

or, $R^6$ is —$NR^{6B}R^{6C}$, —$(CH_2)_{n6}NR^{6B}R^{6C}$, —C(O)$NR^{6B}R^{6C}$, —$O(CH_2)_{m6}OR^{6A}$, substituted or unsubstituted 5 to 6 membered heterocycloalkyl or substituted or unsubstituted $C_6$-$C_{12}$ aryl; $R^5$ and $R^7$ are hydrogen;

or, $R^7$ is —$NR^{7B}R^{7C}$, —$(CH_2)_{n7}NR^{7B}R^{7C}$, —C(O)$NR^{7B}R^{7C}$, —$O(CH_2)_{m7}OR^{7A}$, substituted or unsubstituted 5 to 6 membered heterocycloalkyl or substituted or unsubstituted $C_6$-$C_{12}$ aryl; $R^5$ and $R^6$ are hydrogen;

X is independently —F, —Cl, —Br or —I;

Each n5, n6, and n7 is independently an integer of 1 to 4;

Each m5, m6, and m7 is independently an integer of 1 to 4;

Each $R^{1A}$, $R^{3A}$, $R^{5A}$, $R^{5B}$, $R^{5C}$, $R^{6A}$, $R^{6C}$, $R^{7A}$, and $R^{7C}$ are independently hydrogen, substituted or unsubstituted $C_1$-$C_4$ alkyl, or substituted or unsubstituted 2 to 4 membered heteroalkyl, each $R^{6B}$ and $R^{7B}$ is independently substituted or unsubstituted $C_1$-$C_4$ alkyl, or substituted or unsubstituted 2 to 4 membered heteroalkyl, or, $R^{5B}$ and $R^{5C}$ together with atoms attached thereto are optionally joined to form a substituted or unsubstituted 5 to 6 membered heterocycloalkyl, or substituted or unsubstituted heteroaryl; $R^{6B}$ and $R^{6C}$ together with atoms attached thereto are optionally joined to form a substituted or unsubstituted 5 to 6 membered heterocycloalkyl, or substituted or unsubstituted heteroaryl; or $R^{7B}$ and $R^{7C}$ together with atoms attached thereto are optionally joined to form a substituted or unsubstituted 5 to 6 membered heterocycloalkyl or substituted or unsubstituted heteroaryl;

or a salt thereof.

2. The compound of claim 1, wherein:

i) $R^6$ and $R^7$ are hydrogen, and $R^{5B}$ and $R^{5C}$ together with atoms attached thereto are joined to form a substituted or unsubstituted piperazinyl;

ii) $R^5$ and $R^7$ are hydrogen, and $R^{6B}$ and $R^{6C}$ together with atoms attached thereto are joined to form a substituted or unsubstituted piperazinyl;

iii) $R^6$ and $R^7$ are hydrogen, and $R^5$ is substituted or unsubstituted heterocycloalkyl;

iv) $R^6$ and $R^7$ are hydrogen, and $R^5$ is substituted or unsubstituted morpholinyl;

v) $R^6$ and $R^7$ are hydrogen, and $R^5$ is —$O(CH_2)_mOH$, $NHR^{5C}$, morpholinyl, or substituted or unsubstituted phenyl, $R^{5C}$ is —$(CH_2)_mOH$, —$(CH_2)_mNH_2$, —$(CH_2)_mNHCH_3$, and —$(CH_2)_mN(CH_3)_2$, and Each m is independently an integer of 1 to 4; and/or vi) the compound is

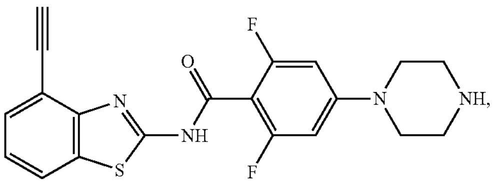

,

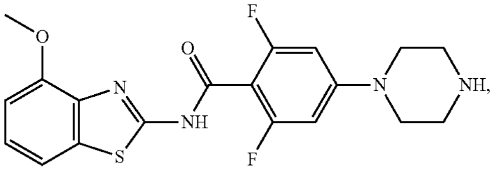

,

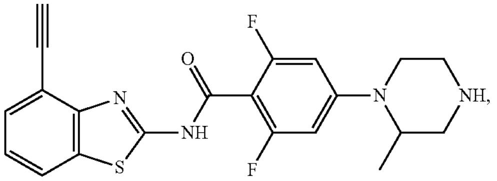

,

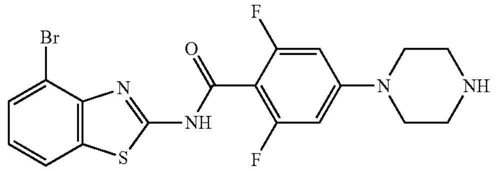

or

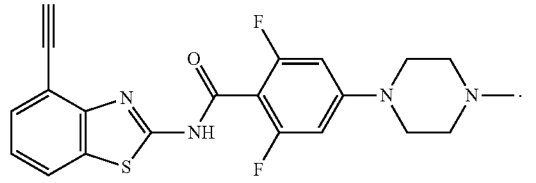

.

3. The compound of claim 2, wherein:

i) the compound has a structure of (I-A)

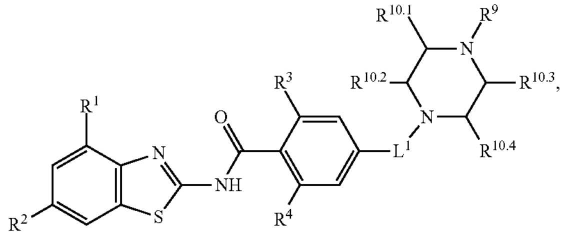

wherein:

$L^1$ is a bond, —C(O)—, or —$(CH_2)_{n5}$;

$R^9$ is hydrogen, —$(CH_2)_mOH$, —$(CH_2)_m(C_6H_5)$, substituted or unsubstituted $C_1$-$C_6$ alkyl, or substituted or unsubstituted 2 to 6 membered heteroalkyl;

Each $R^{10.1}$, $R^{10.2}$, $R^{10.3}$ and $R^{10.4}$ is independently hydrogen, —$OR^{10A}$, —C(O) $OR^{10A}$, —$NR^{10B}R^{10C}$, —$(CH_2)_m$ OH, substituted or unsubstituted $C_1$-$C_6$ alkyl, substituted or unsubstituted 2 to 6 membered heteroalkyl, or substituted or unsubstituted $C_3$-$C_6$ cycloalkyl, or one or more of $R^{10.1}$, $R^{10.2}$, $R^{10.3}$, and $R^{10.4}$ are optionally joined to each other or to atoms of the piperazinyl ring to form a substituted or unsubstituted heterocycloalkyl;

Each m is independently an integer of 1 to 4; and

Each $R^{10A}$, $R^{10B}$ and $R^{10C}$ are independently hydrogen, substituted or unsubstituted $C_1$-$C_4$ alkyl, substituted or unsubstituted 2 to 4 membered heteroalkyl, substituted or unsubstituted 5 to 6 membered heterocycloalkyl, or substituted or unsubstituted 5 to 6 membered heteroaryl;

ii) the compound has a structure of (I-B)

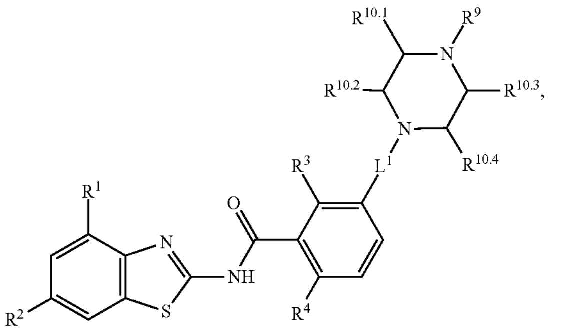

wherein:

$L^1$ is a bond, —C(O)—, or $-(CH_2)_{n6}$;

$R^9$ is hydrogen, $-(CH_2)_mOH$, $-(CH_2)_m(C_6H_5)$, $-C(O)NR^{9B}R^{9C}$, substituted or unsubstituted $C_1$-$C_6$ alkyl, substituted or unsubstituted 2 to 6 membered heteroalkyl;

Each $R^{10.1}$, $R^{10.2}$, $R^{10.3}$ and $R^{10.4}$ is independently hydrogen, $-OR^{10A}$, $-C(O)OR^{10A}$, $-NR^{10B}R^{10C}$, $-(CH_2)_mOH$, substituted or unsubstituted $C_1$-$C_6$ alkyl, substituted or unsubstituted 2 to 6 membered heteroalkyl, or substituted or unsubstituted $C_3$-$C_6$ cycloalkyl, or one or more of $R^{10.1}$, $R^{10.2}$, $R^{10.3}$, and $R^{10.4}$ are optionally joined to each other or to atoms of the piperazinyl ring to form a substituted or unsubstituted heterocycloalkyl;

Each m is independently an integer of 1 to 4; and

Each $R^{9B}$, $R^{9C}$, $R^{10A}$, $R^{10B}$ and $R^{10C}$ are independently hydrogen, substituted or unsubstituted $C_1$-$C_4$ alkyl, substituted or unsubstituted 2 to 4 membered heteroalkyl, substituted or unsubstituted 5 to 6 membered heterocycloalkyl, or substituted or unsubstituted 5 to 6 membered heteroaryl;

iii) the compound has a structure of (I-C)

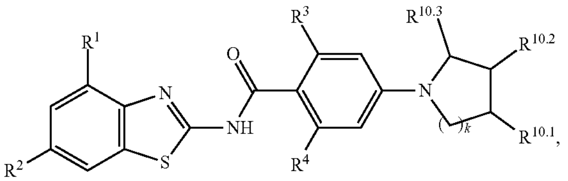

wherein:

k is 1 or 2;

Each $R^{10.1}$, $R^{10.2}$, and $R^{10.3}$ is independently hydrogen, $-OR^{10A}$, $-C(O)OR^{10A}$, $-NR^{10B}R^{10C}$, $-(CH_2)_mOH$, substituted or unsubstituted $C_1$-$C_6$ alkyl, substituted or unsubstituted 2 to 6 membered heteroalkyl, or substituted or unsubstituted $C_3$-$C_6$ cycloalkyl, or one or more of $R^{10.1}$, $R^{10.2}$, and $R^{10.3}$ are optionally joined to each other or to atoms of the heterocyclic ring to form a substituted or unsubstituted heterocycloalkyl;

m is an integer of 1 to 4; and

Each $R^{10A}$, $R^{10B}$ and $R^{10C}$ are independently hydrogen, or unsubstituted $C_1$-$C_6$ alkyl; or the compound has a structure of (I-D)

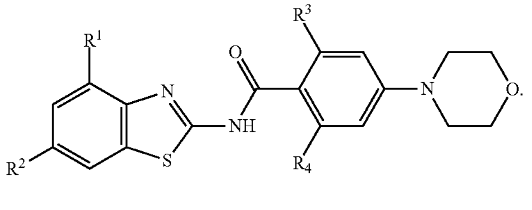

4. The compound of claim 3, wherein:

i) in the compound I-A, each $R^{10.1}$, $R^{10.2}$, $R^{10.3}$, and $R^{10.4}$ is independently hydrogen, oxo, or unsubstituted $C_1$-$C_4$ alkyl, —C(O)OH, or $-CH_2OH$;

ii) in the compound I-A, $R^5$ is

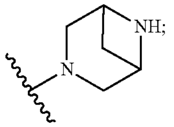 [SMILES: *N1CC2CC(C1)N2]

iii) the compound I-A has a structure of:

(I-A-1)

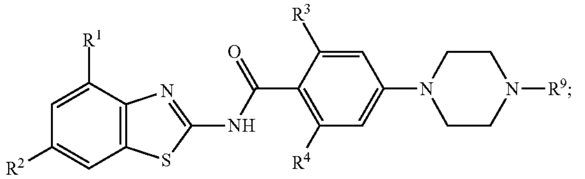

iv) in the compound I-B, $R^9$, $R^{10.1}$, $R^{10.2}$, $R^{10.3}$ and $R^{10.4}$ are hydrogen;

v) in the compound I-B, $R^9$ is methyl, ethyl, propyl, $-C(O)NH_2$,

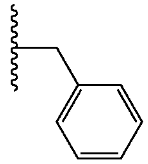, or 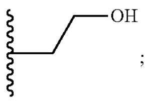;

vi) in the compound I-C, each $R^{10.1}$, $R^{10.2}$, and $R^{10.3}$ is independently hydrogen, —C(O)OH, $-C(O)OCH_3$, $-NH_2$, —OH, or $-(CH_2)OH$;

vii) in the compound I-C, $R^{10.1}$ is independently hydrogen, —C(O)OH, $-C(O)OCH_3$, $-NH_2$, —OH, or $-(CH_2)OH$, and $R^{10.2}$ and $R^{10.3}$ are hydrogen; and/or viii) the compound is
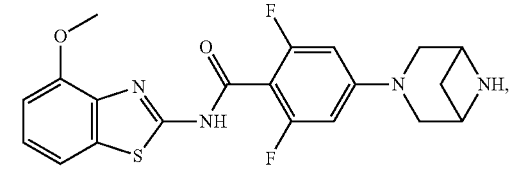
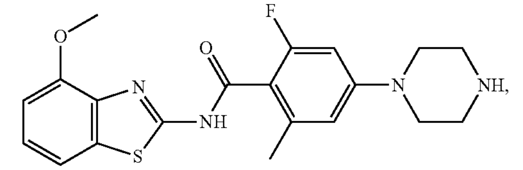
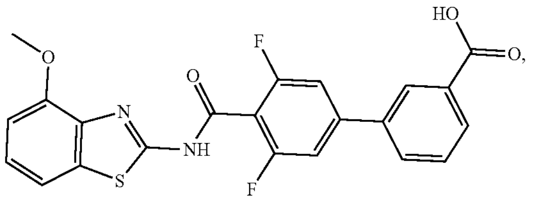
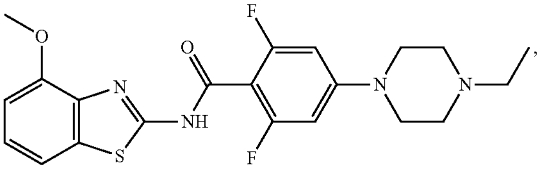
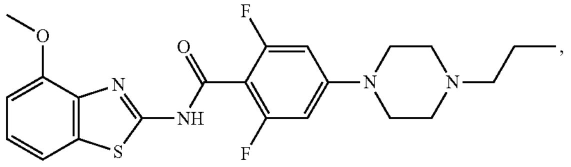
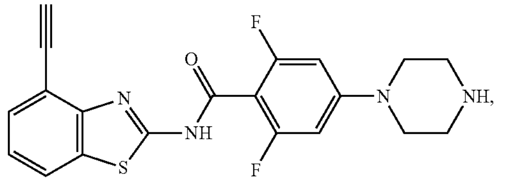
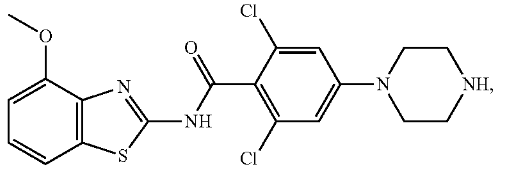
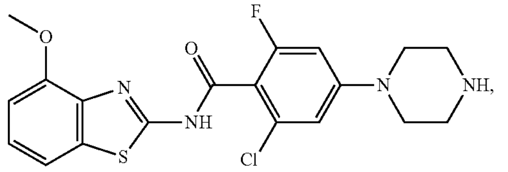
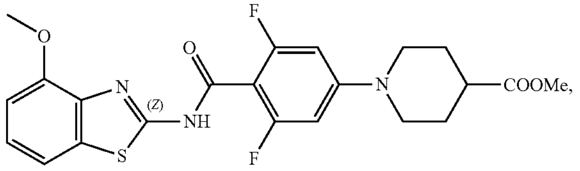
-continued
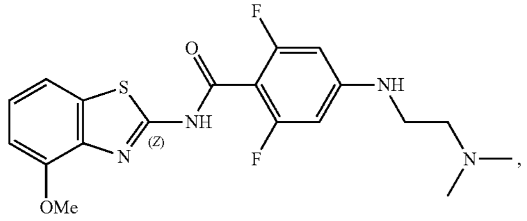
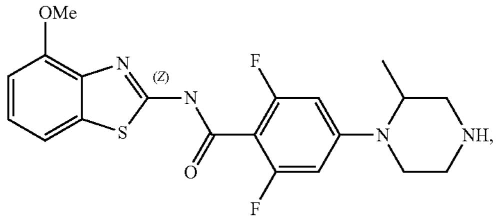
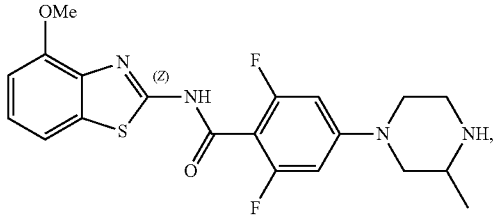
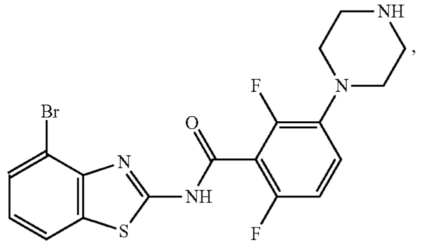
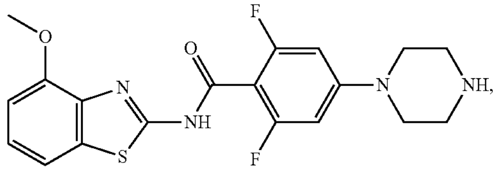
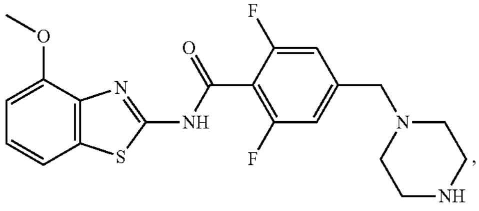
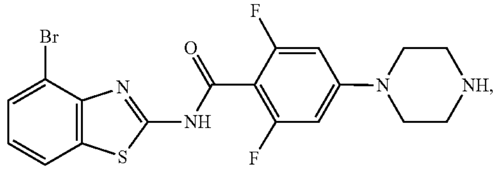
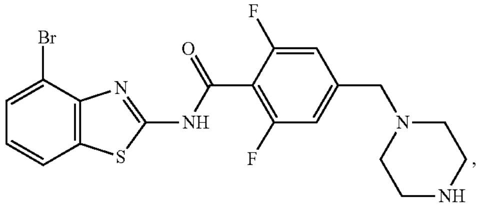

-continued
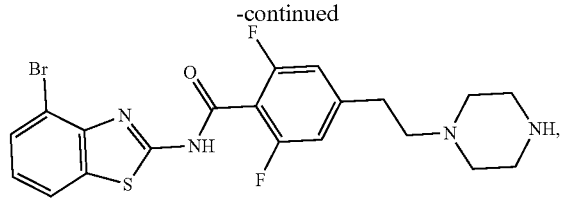
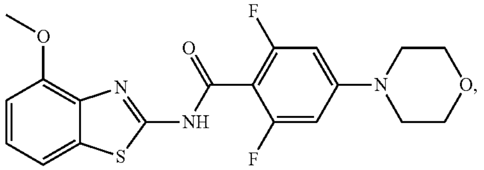
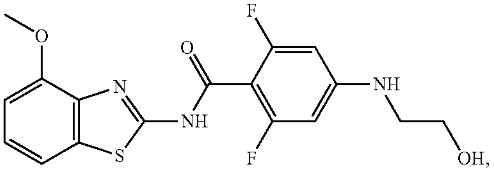
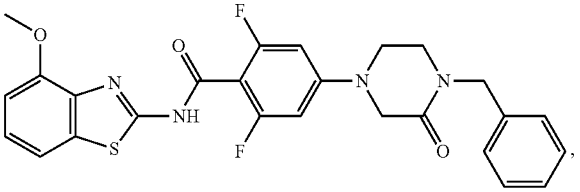
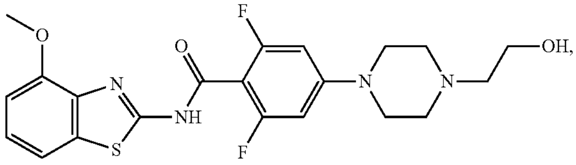
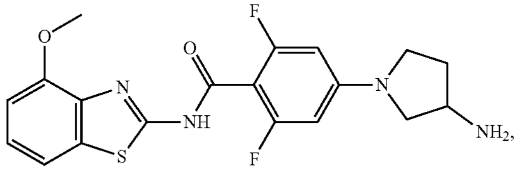
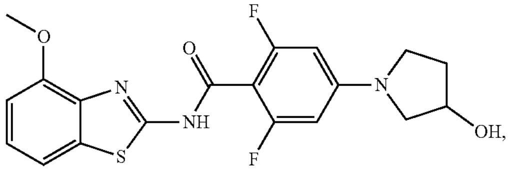
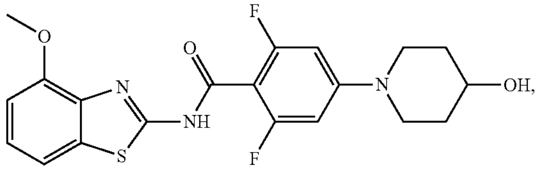
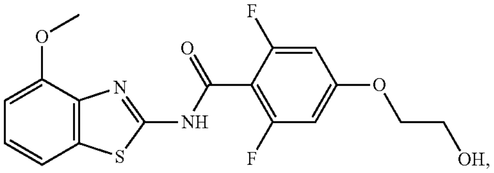
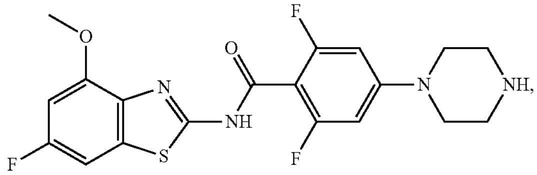
-continued
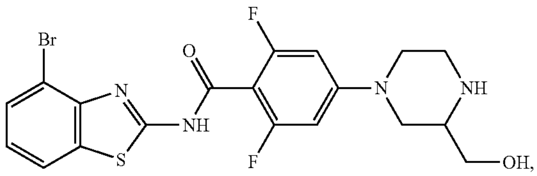
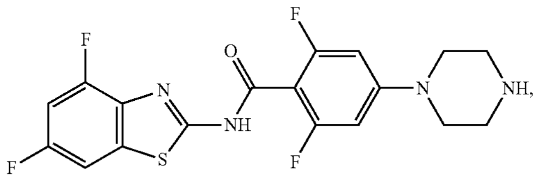
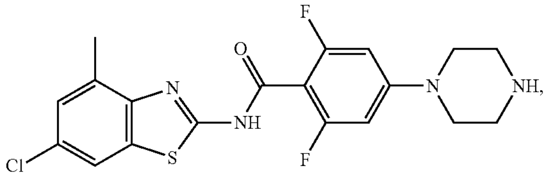
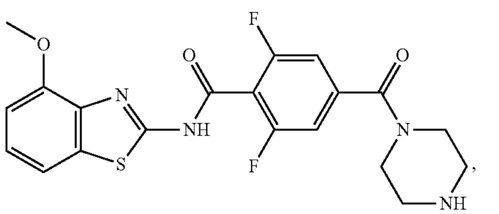
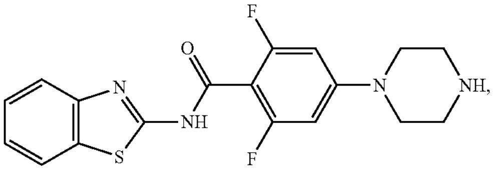
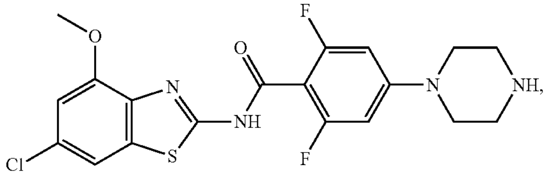
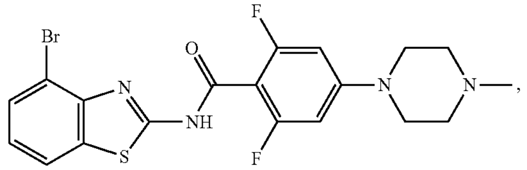
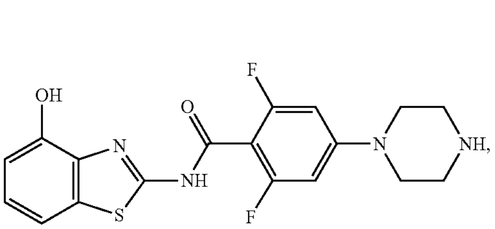
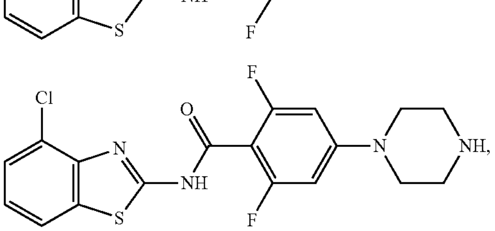

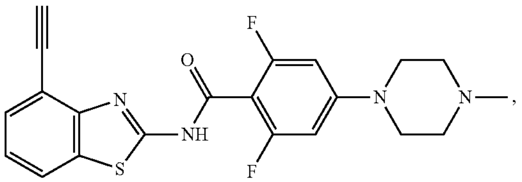
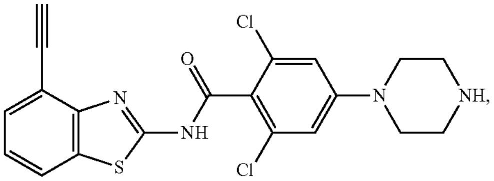
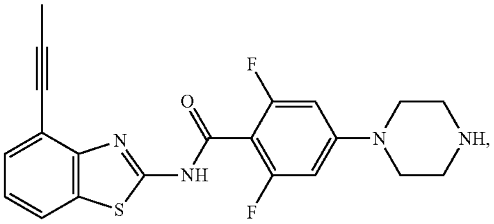
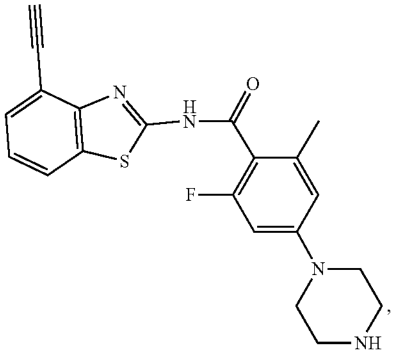
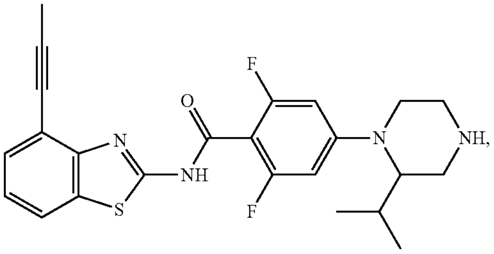
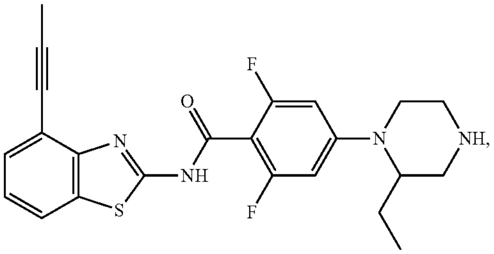
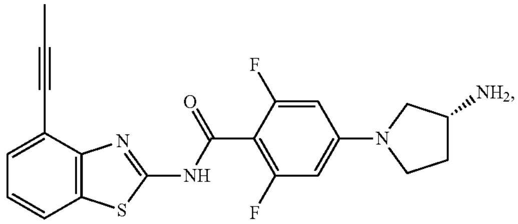
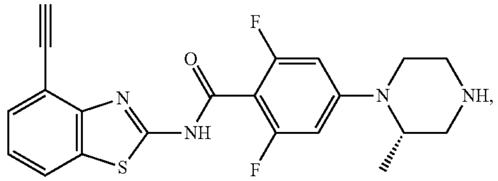
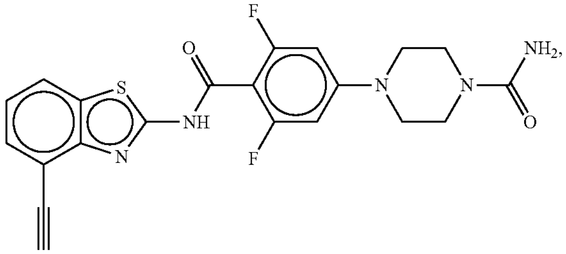
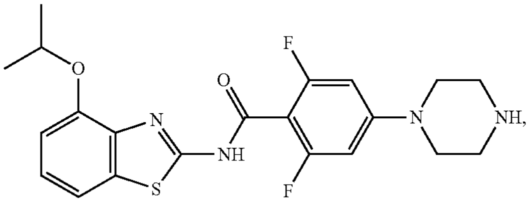
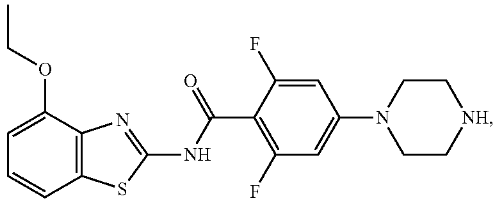
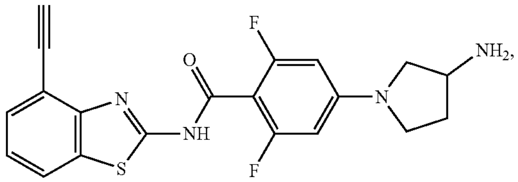
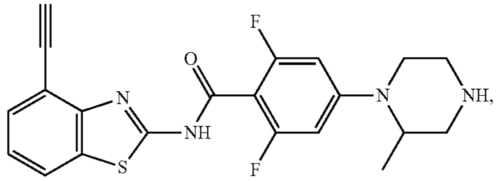
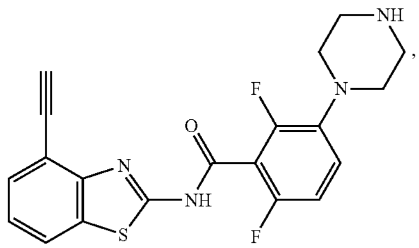
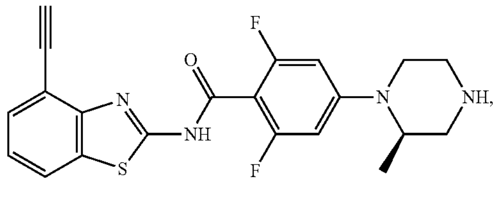

-continued
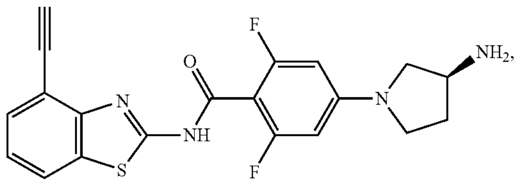
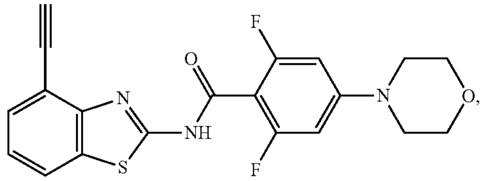
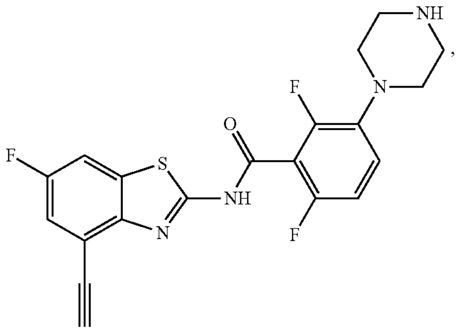
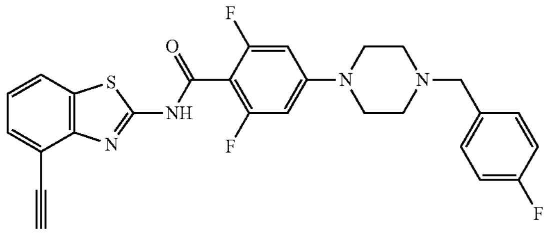
or
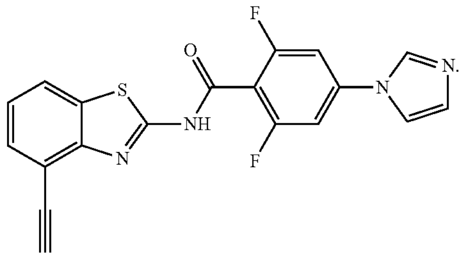
5. The compound of claim 4, wherein:
i) in the compound I-A-1, $R^1$ is hydrogen, halogen, unsubstituted $C_1$-$C_4$ alkyl, unsubstituted $C_3$-$C_6$ cycloalkyl, —$OCX_3$, —$OCH_2X$, —$OCHX_2$, or —$OR^{1A}$, and $R^{1A}$ is hydrogen or unsubstituted $C_1$-$C_4$ alkyl;
ii) in the compound I-A-1, $R^2$ is hydrogen, —F, —Cl, or —Br;
iii) the compound I-A-1 is
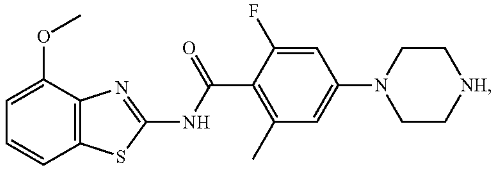
-continued
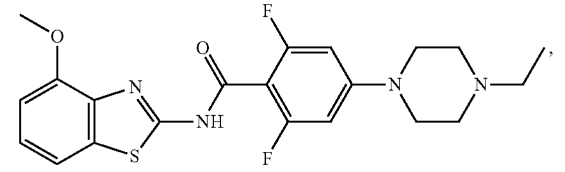
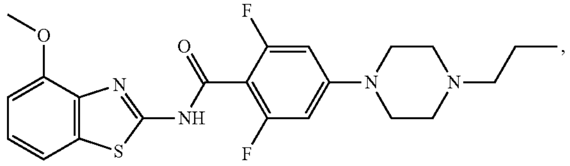
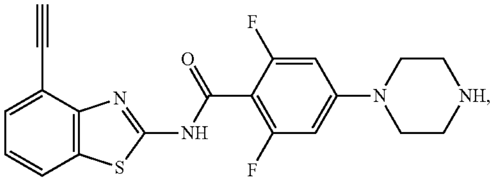
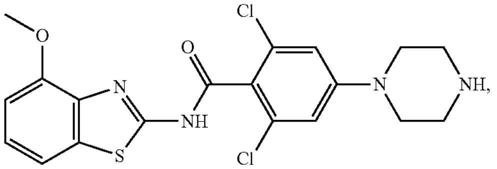
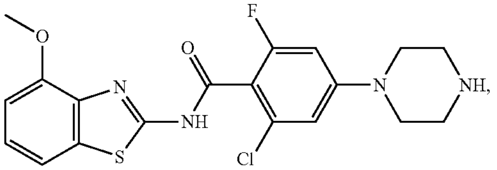
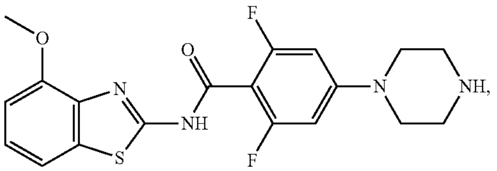
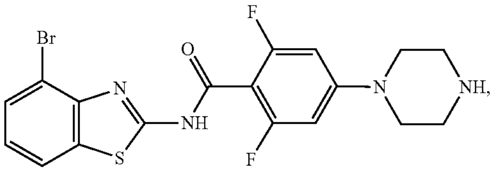
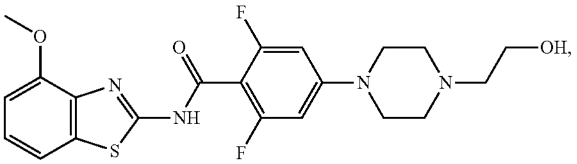
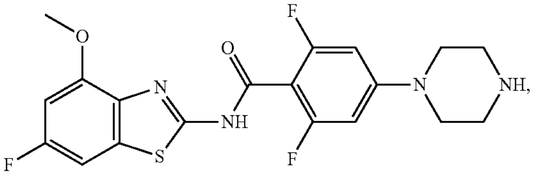
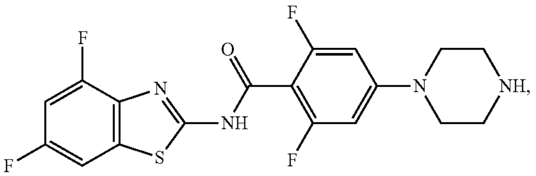

-continued
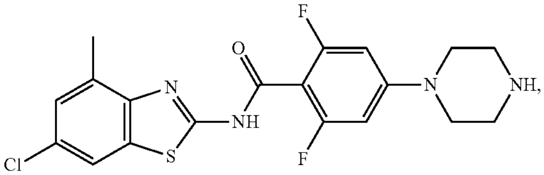
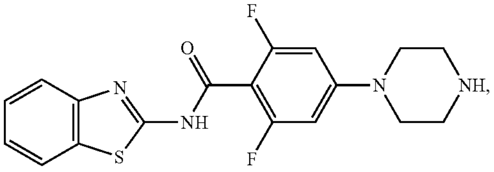
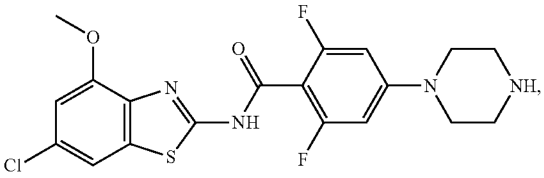
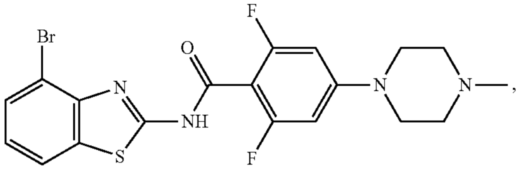
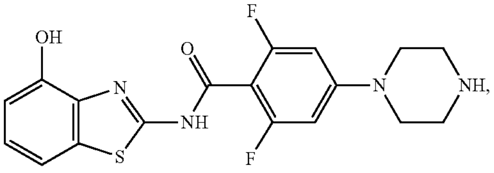
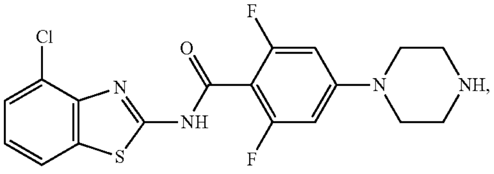
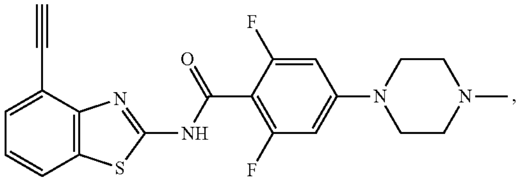
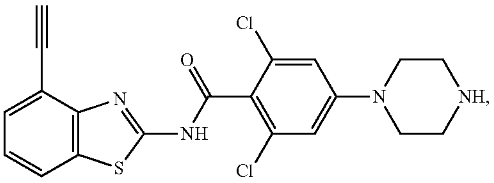
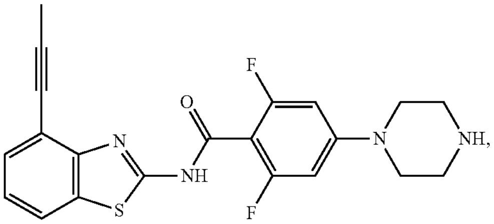
or
-continued
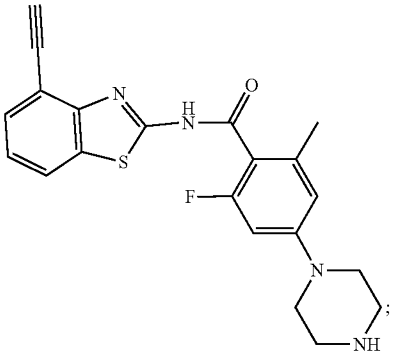
and/or
iv) the compound I-A-1 has a structure of
(I-A-1a)
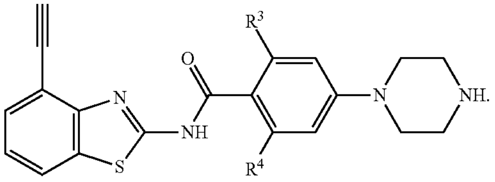
6. A pharmaceutical composition comprising a compound of claim 1, and a pharmaceutically acceptable carrier or excipient.
7. The compound of claim 2, wherein:
i) $R^5$ is
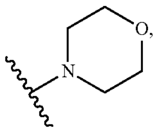
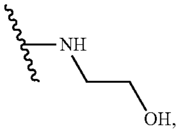
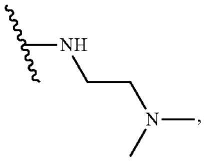
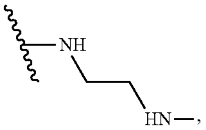
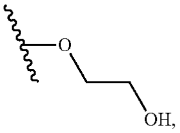
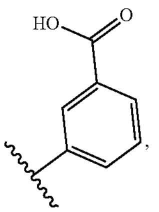

-continued

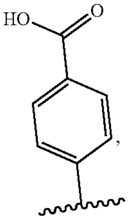,

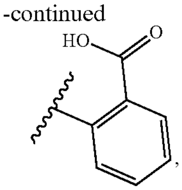, or

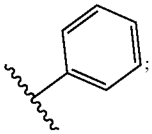;

ii) $R^1$ is hydrogen, halogen, unsubstituted $C_1$-$C_4$ alkyl, unsubstituted $C_3$-$C_6$ cycloalkyl, —$OCX_3$, —$OCH_2X$, —$OCHX_2$, or —$OR^{1A}$; and $R^{1A}$ is hydrogen or unsubstituted $C_1$-$C_4$ alkyl;

iii) $R^1$ is hydrogen, methyl, ethyl, —C≡CH, —C≡CH—$CH_3$, —OH, —$OCH_3$, —$OCHF_2$, —$OCH_2F$, —$OCF_3$, —F, —Cl, or —Br;

iv) $R^1$ is —$OCH_3$, v) $R^1$ is —$OCH_3$, cyclopropyl, or —Br;

vi) $R^2$ is hydrogen or halogen;

vii) each $R^3$ and $R^4$ is independently halogen, or unsubstituted $C_1$-$C_4$ alkyl; and/or viii) $R^3$ and $R^4$ is independently —F, —Cl, or methyl.

* * * * *